US012662668B2

(12) United States Patent 
Šikšnys et al.

(10) Patent No.: US 12,662,668 B2 
(45) Date of Patent: Jun. 23, 2026

(54) RNA-DIRECTED DNA CLEAVAGE BY THE CAS9-CRRNA COMPLEX

(71) Applicant: Vilnius University, Vilnius (LT)

(72) Inventors: Virginijus Šikšnys, Vilnius (LT); Giedrius Gasiūnas, Biržų r. (LT); Tautvydas Karvelis, Vilniaus r. (LT)

(73) Assignee: Vilnius University, Vilnius (LT)

( * ) Notice: Subject to any disclaimer, the term of this patent is extended or adjusted under 35 U.S.C. 154(b) by 702 days.

(21) Appl. No.: 17/857,480

(22) Filed: Jul. 5, 2022

(65) Prior Publication Data

US 2023/0123754 A1 Apr. 20, 2023

Related U.S. Application Data

(63) Continuation of application No. 14/743,764, filed on Jun. 18, 2015, now abandoned, which is a continuation of application No. 14/385,241, filed as application No. PCT/LT2013/000006 on Mar. 15, 2013, now Pat. No. 9,637,739.

(60) Provisional application No. 61/625,420, filed on Apr. 17, 2012, provisional application No. 61/613,373, filed on Mar. 20, 2012.

(51) Int. Cl.
|  |  |
| --- | --- |
| *C12N 9/22* | (2006.01) |
| *C12N 15/10* | (2006.01) |
| *C12N 15/113* | (2010.01) |
| *C12N 15/90* | (2006.01) |
| *C12P 19/34* | (2006.01) |
| *C12Q 1/6811* | (2018.01) |

(52) U.S. Cl.
CPC .............. *C12N 15/113* (2013.01); *C12N 9/22* (2013.01); *C12N 15/102* (2013.01); *C12N 15/902* (2013.01); *C12N 15/907* (2013.01); *C12P 19/34* (2013.01); *C12Q 1/6811* (2013.01); *C12N 2310/12* (2013.01); *C12N 2310/14* (2013.01); *C12N 2310/20* (2017.05); *C12N 2310/3513* (2013.01); *C12N 2310/531* (2013.01); *C12N 2320/00* (2013.01); *C12N 2800/80* (2013.01)

(58) Field of Classification Search
None
See application file for complete search history.

(56) References Cited

U.S. PATENT DOCUMENTS

| | | | |
| --- | --- | --- | --- |
| 3,862,002 A | 1/1975 | Sanders | |
| 8,697,359 B1 | 4/2014 | Zhang | |
| 9,637,739 B2 | 5/2017 | Siksynys et al. | |
| 10,844,378 B2 | 11/2020 | Siksynys et al. | |
| 11,555,187 B2 | 1/2023 | Siksnys et al. | |
| 2010/0076057 A1 | 3/2010 | Sontheimer | |
| 2014/0068797 A1 | 3/2014 | Doudna | |

| | | | |
| --- | --- | --- | --- |
| 2014/0242664 A1 | 8/2014 | Zhang et al. | |
| 2014/0342456 A1 | 11/2014 | Mali et al. | |
| 2014/0357530 A1 | 12/2014 | Zhang et al. | |
| 2015/0240261 A1 | 8/2015 | Siksynys et al. | |
| 2015/0275231 A1 | 10/2015 | West | |
| 2015/0284727 A1 | 10/2015 | Kim et al. | |
| 2015/0291961 A1 | 10/2015 | Siksynys et al. | |
| 2016/0046961 A1 | 2/2016 | Jinek et al. | |
| 2023/0131972 A1 | 4/2023 | Church et al. | |
| 2023/0272394 A1 | 8/2023 | Siksnys et al. | |

FOREIGN PATENT DOCUMENTS

| | | |
| --- | --- | --- |
| CN | 110312792 A | 10/2019 |
| CN | 111448313 A | 7/2020 |
| CN | 112424824 A | 2/2021 |
| CN | 116555254 A | 8/2023 |
| JP | 2015-510778 | 4/2015 |
| JP | 2015-523856 | 8/2015 |
| JP | 2016-504026 | 2/2016 |
| WO | WO 2007/025097 | 3/2007 |
| WO | WO 2008/108989 | 9/2008 |
| WO | WO 2011/146121 | 11/2011 |
| WO | WO 2011/159369 | 12/2011 |
| WO | WO 2012/012667 | 1/2012 |
| WO | 2013141680 | 9/2013 |
| WO | WO 2013/142578 | 9/2013 |
| WO | WO 2013/176772 | 11/2013 |
| WO | WO 2014/065596 | 5/2014 |

(Continued)

OTHER PUBLICATIONS

Amau et al., "Current strategies for the use of affinity tags and tag removal for the purification of recombinant proteins," *Protein Expression and Purification*, vo. 48, pp. 1-13 (2006).

Deveau et al., "CRISPR/Cas system and its role in phage-bacteria interactions," *The Annual Review of Microbiology*, vol. 64, pp. 475-493 (2010). (19 pages).

Deltcheva et al., "CRISPR RNA maturation by trans-encoded small RNA and host factor RNase III," *Nature*, vol. 471, pp. 602-607 (2011) (6 pages), Methods (2 pages). (8 total pages).

Deltcheva et al., "CRISPR RNA maturation by trans-encoded small RNA and host factor RNase III," Supplementary Tables, *Nature*, vol. 471 (2011). (22 pages).

(Continued)

*Primary Examiner* — Richard G Hutson

(74) *Attorney, Agent, or Firm* — Bookoff McAndrews, PLLC

(57) ABSTRACT

Isolation or in vitro assembly of the Cas9-crRNA complex of the *Streptococcus thermophilus* CRISPR3/Cas system and use for cleavage of DNA bearing a nucleotide sequence complementary to the crRNA and a proto-spacer adjacent motif. Methods for site-specific modification of a target DNA molecule using an RNA-guided DNA endonuclease comprising at least one RNA sequence and at least one of an RuvC active site motif and an HNH active site motif; for conversion of Cas9 polypeptide into a nickase cleaving one strand of double-stranded DNA by inactivating one of the active sites (RuvC or HNH) in the polypeptide by at least one point mutation; for assembly of active polypeptide-polyribonucleotides complex in vivo or in vitro; and for re-programming a Cas9-crRNA complex specificity in vitro or using a cassette containing a single repeat-spacer-repeat unit.

17 Claims, 15 Drawing Sheets

Specification includes a Sequence Listing.

(56)            References Cited

FOREIGN PATENT DOCUMENTS

| WO | 2014093595 A1 | 6/2014 |
|----|----|----|
| WO | WO 2014/089290 | 6/2014 |
| WO | WO 2014/093622 | 6/2014 |
| WO | WO 2014/099750 | 6/2014 |
| WO | WO 2014093712 | 6/2014 |
| WO | 2019217336 A2 | 11/2019 |
| WO | 2022261115 A1 | 12/2022 |
| WO | 2023025767 A1 | 3/2023 |

OTHER PUBLICATIONS

Deltcheva et al., "CRISPR RNA maturation by trans-encoded small RNA and host factor Rnase III," Supplementary Figures, *Nature*, vol. 471 (2011). (35 pages).

Makarova et al., "Evolution and classification of the CRISPR-Cas system," *Nature Reviews Microbiology*, vol. 9, pp. 467-477 (2011). (11 pages).

Sapranauskas et al., "The *Streptococcus thermophiles* CRISPR/Cas system provides immunity in *Escherichia coli*," *Nucleic Acids Research*, vol. 39, pp. 9275-9282 (2011) (8 pages), Supplementary Figures, Supplementary Materials and Methods, and Supplementary Tables (10 pages). (18 total pages).

Jinek et al., "RNA-programmed genome editing in human cells," *eLife*, vol. 2, at e00471 (2013). (9 pages).

Jinek et al., "A Programmable Dual-RNA-Guided DNA Endonuclease in Adaptive Bacterial Immunity," *Science*, vol. 337, pp. 816-821 (2012) (6 pages), Supplementary Materials and Methods (36 pages). (42 total pages).

Gasiunas et al., "Cas9-crRNA ribonucleoprotein complex mediates specific DNA cleavage for adaptive immunity in bacteria," *Proc. Nat. Acad. Sci.*, vol. 109, pp. E2579-E2586 (2012) (8 pages), Supporting Information (8 pages). (16 total pages).

Cong et al., "Multiplex Genome Engineering Using CRISPR/Cas Systems," *Science*, vol. 339, pp. 819-823 (2013) (5 pages), Supplementary Material (25 pages). (35 total pages).

Qi et al., "Repurposing CRISPR as an RNA-Guided Platform for Sequence-Specific Control of Gene Expression," *Cell*, vol. 152, pp. 1173-1183 (2013) (11 pages), Supplemental Information (7 pages). (18 total pages).

Jiang et al., "RNA-guided editing of bacterial genomes using CRISPR-Cas systems," *Nature Biotechnology*, vol. 31, pp. 233-239 (2013) (7 pages), Online Methods (2 pages), Supplementary Materials (21 pages). (30 total pages).

Cho et al., "Targeted genome engineering in human cells with the Cas9 RNA-guided endonuclease," *Nature Biotechnology*, vol. 31, pp. 230-232 (2013) (3 pages), Supplementary Information (11 pages).

Van Der Oost et al., "CRISPR-based adaptive and heritable immunity in prokaryotes," *Trends in Biochemical Sciences*, vol. 34, pp. 401-408 (2009). (8 pages).

Garneau et al., "The CRISPR/Cas bacterial immune system cleaves bacteriophage and plasmid DNA," *Nature*, vol. 468, pp. 67-71 (2010). (5 pages).

Shapiro et al., "A 21st century view of evolution: genome system architecture, repetitive DNA, and natural genetic engineering," *Gene*, vol. 345, issue 1, pp. 91-100 (2005). (10 pages).

Gaberc-Porekar et al., "Potential for Using Histidine Tags in Purification of Proteins at Large Scale," *Chem. Eng. Techno.*, vol. 28, issue 1, pp. 1306-1314 (2005). (9 pages).

Arnau et al., "Current strategies for the use of affinity tags and tag removal for the purification of recombinant proteins," *Protein Expression and Purification*, vol. 48 (2006). (13 pages).

Wiedenhelt et al. "Structures of the RNA-guided surveillance complex from a bacterial immune system," *Nature*, vol. 477, pp. 486-489 with Supplementary Information pp. 1-6 (2013). (11 pages).

Office Action in Chinese Application No. 201380023255.3, dated Aug. 1, 2017 (15 pages, including original and English translation).

Office Action in Chinese Application No. 201380023255.3, dated Nov. 29, 2016 (15 pages, including original and English translation).

Office Action in Chinese Application No. 201380023255.3, dated Jan. 26, 2016 (8 pages, including original and English translation).

Office Action in Japanese Application No. 2015-501880, dated Apr. 18, 2017 (25 pages, including original and English translation).

Office Action in Eurasian Patent Application No. 201491728, dated Nov. 23, 2016 (4 pages, including original and English translation).

Notice of Readiness to Grant Patent in Eurasian Patent Application No. 201491728, dated Apr. 28, 2017 (1 page).

Communication in European Application No. 13715080.1, dated Jul. 14, 2017 (7 pages).

Communication in European Application No. 13715080.1, dated Nov. 8, 2016 (9 pages).

Communication in European Application No. 13715080.1, dated Feb. 16, 2016 (13 pages).

Third Party Observation in International Application No. PCT/LT2013/000006, dated Jul. 18, 2014 (7 pages).

International Search Report in International Application No. PCT/LT2013/000006, dated Jul. 24, 2013 (7 pages).

Written Opinion in International Application No. PCT/LT2013/000006, dated Jul. 24, 2013 (10 pages).

International Preliminary Report on Patentability in International Application No. PCT/LT2013/000006, dated Sep. 23, 2014 (11 pages).

International Search Report in International Application No. PCT/US2013/033106, dated Jul. 24, 2013 (5 pages).

Written Opinion in International Application No. PCT/US2013/033106, dated Jul. 24, 2013 (11 pages).

International Preliminary Report on Patentability in International Application No. PCT/US2013/033106, dated Sep. 23, 2014 (11 pages).

Third Party Observation in International Application No. PCT/US2013/033106, dated Jul. 18, 2014 (8 pages).

CRISPR-associated endonuclease Cas9, UniProt Database Accession No. G3ECR1 (available online at http://www.uniprot.org/uniprot/G3ECR1.txt), updated May 23, 2018, accessed May 29, 2018 (3 pages).

Office Action in Japanese Application No. 2015-501880, dated Apr. 24, 2018 (27 pages, including original and English translation).

Office Action in Chinese Application No. 201380023255.3, dated Apr. 17, 2018 (11 pages, including original and English translation).

Communication in European Application No. 13715080.1, dated Mar. 29, 2018 (5 pages).

Third Party Observation in EP Application No. 13715080.1, mailed Jul. 3, 2018 (4 pages).

Communication pursuant to Article 94(3) EPC in EP Application No. 13715080.1, mailed Jul. 16, 2018 (6 pages).

Notice of Allowance in Japanese Patent Application No. 2015-501880, dated Sep. 18, 2018 (8 pages, including original and English translation).

Office Action in Mexican Patent Application No. MX/a/2014/011279, dated Sep. 5, 2018 (5 pages).

Communication pursuant to Article 71(3) EPC in European Application No. 13715080.1, dated Jan. 23, 2019 (7 pages).

Examination Report in Indian Application No. 7846/DELNP/2014, dated Feb. 14, 2019 (7 pages).

Office Action in Canadian Application No. 2,867,849, dated Jan. 17, 2019 (4 pages).

Office Action in Mexican Application No. MX/a/2014/011279, dated Feb. 20, 2019 (4 pages).

Non-final Office Action in U.S. Appl. No. 14/385,241, dated Jun. 18, 2015 (12 pages).

Final Office Action in U.S. Appl. No. 14/385.241, dated Oct. 22, 2015 (20 pages).

Non-final Office Action in U.S. Appl. No. 14/683,443, dated Apr. 7, 2016 (12 pages).

Non-final Office Action in U.S. Appl. No. 14/683,443, dated Jun. 29, 2017 (36 pages).

Final Office Action in U.S. Appl. No. 14/683,443, dated Nov. 18, 2016 (21 pages).

(56) References Cited

OTHER PUBLICATIONS

Final Office Action in U.S. Appl. No. 14/683,443, dated Mar. 29, 2018 (13 pages).
Non-final Office Action in U.S. Appl. No. 14/743,764, dated Jul. 24, 2015 (13 pages).
Non-final Office Action in U.S. Appl. No. 14/743,764, dated Jul. 29, 2016 (20 pages).
Non-final Office Action in U.S. Appl. No. 14/743,764, dated Jul. 6, 2017 (27 pages).
Final Office Action in U.S. Appl. No. 14/743,764, dated Nov. 20, 2015 (16 pages).
Final Office Action in U.S. Appl. No. 14/743,764, dated Dec. 15, 2016 (24 pages).
Final Office Action in U.S. Appl. No. 14/743,764, dated Apr. 3, 2018 (22 pages).
Final Office Action in U.S. Appl. No. 14/385,857, dated Jun. 16, 2016 (6 pages).
Final Office Action in U.S. Appl. No. 14/385,857, dated Jun. 8, 2017 (12 pages).
Non-final Office Action in U.S. Appl. No. 14/385,857, dated Oct. 26, 2015 (14 pages).
Non-final Office Action in U.S. Appl. No. 14/385,857, dated Dec. 6, 2016 (12 pages).
Non-final Office Action in U.S. Appl. No. 15/834,578, dated Apr. 4, 2019 (11 pages).
Notice of Allowance in U.S. Appl. No. 14/385,241, dated Mar. 9, 2017 (7 pages).
Hwang et al., Efficient genome editing in zebrafish using a CRISPR-Cas system, *Nature Biotech*, vol. 31, No. 3, pp. 227-229 (2013).
Mali et al., "RNA-guided human genome engineering via Cas9," *Science*, vol. 339, pp. 823-826 (2013).
Office Action in Brazilian Application No. BR112014023353-5, dated Aug. 14, 2019 (10 pages).
Office Action in Japanese Application No. 2018-196574, dated Sep. 17, 2019 (20 pages).
Office Action in U.S. Appl. No. 16/148,783, dated Jul. 12, 2019 (34 pages).
Science [online], vol. 337, pp. 816-821 and Supplementary Materials, Epub, Jun. 28, 2012, [retrieved on Oct. 27, 2016], retrieved from the internet <URL:http://science.sciencemag.org/content/337/6096/816.long>.
Science [online], vol. 339, pp. 819-823 and Supplementary Material, Epub, Jan. 3, 2013 [retrieved on Oct. 27, 2016], retrieved from the internet <URL:http://science.sciencemag.org/content/339/6121/819.long>.
Nat. Biotechnol. [online], vol. 31, pp. 233-239, Online Methods and Supplementary Materials, Epub, Jan. 29, 2013, [retrieved on Oct. 27, 2016], retrieved from the internet <URL: http://www.nature.com/nbt/journal/v31/n3/full/nbt.2508.html>.
Hsu et al., "Development and Applications of CRISPR-Cas9 for Genome Engineering," Cell 157, pp. 1262-1278 Jun. 5, 2014 (17 pages).
Marraffini et al., "Self versus non-self discrimination during CRISPR RNA-directed immunity," Nature Letters, vol. 463 l28, Jan. 2010, pp. 568-572 (5 pages).
Macrae et al., "Ribonuclease revisited: structural insights into ribonuclease III family enzymes," Current Opinion in Structural Biology 2007, 17:138-145 (8 pages).
Example 7—Nucleic Acids in the USPTO's Guidelines on Patent Eligibiltiy for Nature-Based Products, pp. 1-17, issued Dec. 16, 2014 (17 pages).
Notice of Allowance in Mexican Application No. MX/a/2014/011279, dated Oct. 3, 2019 (2 pages).
Extended European Search Report and Annex for European Application No. 19179124.3, dated Oct. 25, 2019 (14 pages).
Final Office Action in U.S. Appl. No. 15/834,578, dated Nov. 14, 2020 (18 pages).
Notice of Opposition in European Application No. 13715080.1, dated Nov. 27, 2019 (7 pages).

Final Office Action in U.S. Appl. No. 14/743,764, dated Dec. 20, 2019 (22 pages).
Final Office Action in U.S. Appl. No. 14/743,764 dated Jun. 15, 2020 (11 pages).
Advisory Action in U.S. Appl. No. 15/834,578, dated Jan. 16, 2020 (4 pages).
Non-Final Office Action in U.S. Appl. No. 15/834,578 dated May 27, 2020 (7 pages).
Office Action in Canadian Application No. 2,867,849 dated Feb. 6, 2020 (4 pages).
Hearing Notice in Indian Application No. 7846/DELNP/2014 dated Jul. 15, 2020 (2 pages).
Final Decision of Rejection in Japanese Application No. 2018-196574 dated Jun. 16, 2020, with English translation (12 pages).
Brief Communication with grounds of opposition by Vossius & Partner in European Patent No. 2828386, dated Apr. 16, 2020, including citation Nos. D1-D20 (746 pages).
Communication of a notice of opposition by Vossius & Partner in European Patent No. 2828386 dated Nov. 27, 2019 (7 pages).
Communication of a notice of opposition by Ms Sandra Pohlman with grounds therefore in European Patent No. 2828386 dated Apr. 16, 2020, including citation Nos. D1-D6 and D6b-D31 (507 pages).
Communication of a notice of opposition by HGF Limited with grounds therefore in European Patent No. 2828386 dated Apr. 17, 2020, including citation Nos. D1-D22 (2395 pages).
Consolidated list of opposition citations in European Patent No. 2828386, European Patent Office, Apr. 10, 2020 (3 pages).
Gaceta de la Propiedad Indstrial, Mexico, p. 211, December 2019 (Official Gazette of Mexican Institute of Industrial Property noting publication of Mexican Application No. MX/a/2019/009736) (2 pages).
Final Office Action in U.S. Appl. No. 15/834,578, dated Nov. 14, 2019 (18 pages).
Letter re: Request for Registration and Grant Under Hong Kong Application No. 15107124.7, dated Nov. 12, 2019 (1 page).
Non-Final Office Action in U.S. Appl. No. 16/148,783, dated Apr. 22, 2020 (19 pages).
Notification of European publication number and information on the application of Article 67(3) EPC in European Application No. 19179124.3, dated Dec. 18, 2019 (2 pages).
Submission Under 37 CFR 1.501 in U.S. Pat. No. 9,637,739, dated Mar. 20, 2020, including Exhibits A-F (101 pages).
Submission Under 37 CFR 1.501 in U.S. Pat. No. 9,637,739, dated Apr. 16, 2020, including Exhibits A-F (101 pages).
Communication Pursuant to Article 94(3) EPC in European Application No. 19179124.3, dated Feb. 18, 2021 (9 pages).
Final Office Action in U.S. Appl. No. 15/834,578, dated Dec. 4, 2020 (13 pages).
Hearing Notice in Indian Application No. 7846/DELNP/2014 dated Sep. 29, 2020 (2 pages).
Hong Kong Intellectual Property Journal bibliographic details for HK Application No. 42020010745.6 (1 page).
Notice of Allowance in Canadian Application No. 2,867,849 dated Mar. 16, 2021 (1 page).
Brief Communication in European Patent No. 2828386 dated Apr. 12, 2021, including citation Nos. D64-D67 (66 pages).
Communication Pursuant to Rule 114(2) in European Application No. 19179124.3, dated Apr. 22, 2021 (4 pages).
Karvelis, T. et al., "Programmable DNA cleavage in vitro by Cas9," Biochem. Soc. Trans, vol. 41, pp. 1401-1406 (2013).
Non-Final Office Action in U.S. Appl. No. 15/834,578, dated Jun. 11, 2021 (16 pages).
Office Action in Brazilian Application No. BR112014023353-5 dated Oct. 19, 2021 (17 pages).
Office Action in Chinese Application No. 201380023255.3, dated Jun. 9, 2021 (16 pages).
Reexamination Decision in Chinese Application No. 201380023255.3, dated Apr. 20, 2021 (11 pages).
Shimizu, Y. et al., "cell-free translation systems for protein engineering," FEBS Journal, vol. 273, pp. 4133-4140 (2006).
Non-Final Office Action in U.S. Appl. No. 14/743,764 dated Feb. 2, 2022 (16 pages).

(56) References Cited

OTHER PUBLICATIONS

Notice of Non-Responsive Amendment in U.S. Appl. No. 14/743,764 dated Sep. 30, 2021 (5 pages).

Non-Final Office Action in U.S. Appl. No. 14/743,764, dated May 31, 2019 (15 pages).

Office Action in Brazilian Application No. BR112014023353-5 dated Feb. 22, 2022 (13 pages).

Office Action in Japanese Application No. 2020-014526 dated Dec. 7, 2021 (39 pages).

Office Action in Japanese Application No. 2020-174803 dated Dec. 21, 2021 (25 pages).

Summons to attend oral proceedings pursuant to Rule 115(1) EPC in European Patent No. 2828386 dated Apr. 13, 2022 (18 pages).

Notice of Abandonment in U.S. Appl. No. 14/743,764 dated Sep. 2, 2022 (2 pages).

Office Action in Canadian Application No. 3,124,374 dated Sep. 16, 2022 (3 pages).

Notification of Publication and Entry into Examination Procedure in Chinese Application No. 202111462778.0, dated May 9, 2022 (2 pages, including original and English translation).

Notice of Publication of Appeal Against Rejection in Brazilian Application No. BR 11 2014 023353-5 A2, dated May 3, 2022 (1 page).

Appeal Decision in Japanese Application No. 2020-014526 dated Nov. 1, 2022 (3 pages).

Brief Communication of a letter from opponent Vossius & Partner in European Patent No. 2828386 dated Sep. 20, 2022 (3 pages).

Brief Communication of a letter from opponent Ms. Sandra Pohlman (dfmp) in European Patent No. 2828386 dated Sep. 19, 2022 (12 pages).

Brief Communication of a letter from opponent HGF in European Patent No. 2828386 dated Sep. 20, 2022 (5 pages).

Brief Communication in European Patent No. 2828386 dated Oct. 31, 2022 (1 page).

Summons to attend oral proceedings pursuant to Rule 115(1) EPC in European Patent No. 2828386 dated Nov. 8, 2022 (9 pages).

Brief Communication in European Patent No. 2828386 dated Nov. 28, 2022 (1 page).

ASU team Wiki (iGEM 2011 Regional Jamboree Americas Oct. 9-10, 2011) (Proof of publication at: http://2011.igem.org/Team:Arizona_State/Project/Introduction; https://2011.igem.org/Team:Arizona_State/Project/CRISPR; http://2011.igem.org/Team:Arizona_State/Project/L_innocua) (ASU—Exhibit A).

Arizona State University (ASU) team poster (iGEM 2011 Regional Jamboree Americas Oct. 9-10, 2011) (Proof of Publication at: https://web.archive.org/web/20160310042354/https:/2011.igem.org/Files/poster/Arizona_State.pdf; https://web.archive.org/web/20120401091350/https://igem.org/Results?year=2011) (ASU poster—Exhibit B).

U.S. Appl. No. 61/613,373, filed Mar. 20, 2012 (p. 1—Exhibit C).

GenBank Accession No. HQ712120, *Streptococcus thermophilus* strain DGCC 7710 SerB (serB) gene, partial cds; CRISPR3 gene locus, complete sequence; and predicted protein gene, partial 7 cds., first appearing Aug. 23, 2011; As cited in Sapranauskas at p. 9277, 2nd col. to p. 9278, 1st col. Exhibit G.

Deltcheva et al., CRISPR RNA maturation by trans-encoded small RNA and host factor RNase III, Nature, 471: 602-609 (Mar. 31, 2011) (Deltcheva—Exhibit B).

GenBank Accession No. HQ712120, *Streptococcus thermophilus* strain DGCC 7710 SerB (serB) gene, partial cds; CRISPR3 gene locus, complete sequence; and predicted protein gene, partial cds., first appearing Aug. 23, 2011; As cited in Sapranauskas at p. 9277, 2nd col. to p. 9278, 1st col. Exhibit G.

Office Action dated Jul. 5, 2017 in parent U.S. Appl. No. 14/743,764 Exhibit H.

U.S. Provisional U.S. Appl. No. 61/613,373, filed Mar. 20, 2012 (p. 1—Exhibit C).

Sapranauskas et al., The *Streptococcus thermophilus* CRISPR/Cas System provides immunity in *Escherichia coli,* Nucl. Acids Res. 39(21):9275-9282 (Aug. 3, 2011) (Sapranauskas—Exhibit A).

Office Action dated Feb. 2, 2022 in parent U.S. Appl. No. 14/743,764 Exhibit I.

U.S. Appl. No. 61/625,420, filed Apr. 17, 2012 (p. 2—Exhibit D).

Karvelis et al., crRNA and tracrRNA guide Cas9-mediated DNA interference in *Streptococcus thermophilus.* RNA Biol. 10(5): 841-51 (Mar. 27, 2013) (Karvelis et al.—Exhibit F).

Final Office Action in U.S. Appl. No. 15/834,578, dated Jan. 25, 2022 (18 pages).

Notice of Allowance in U.S. Appl. No. 15/834,578, dated Sep. 14, 2022 (12 pages).

Examination Report in Canadian Application No. 3124374 dated Sep. 16, 2022 (3 pages).

Notice of Allowance in Canadian Application No. 3124374 dated Sep. 1, 2023 (1 page).

Decision on the Approval of Patent Term Adjustment in Chinese Application No. 201380023255.32 dated Sep. 26, 2024 (2 pages).

First Office Action in Chinese Application No. 202111462778.0 dated Apr. 28, 2023 (12 pages).

Second Office Action in Chinese Application No. 202111462778.0 dated Nov. 22, 2023 (9 pages).

Notice of Allowance in Chinese Application No. 202111462778.0 dated Apr. 19, 2024 (5 pages).

Notice of Allowance in Japanese Application No. 2020-174803 dated Jun. 28, 2022 (8 pages).

Communication pursuant to Article 94(3) EPC in European Application No. 19179124.3 dated Dec. 16, 2022 (7 pages).

Communication pursuant to Article 94(3) EPC in European Application No. 19179124.3 dated Oct. 29, 2024 (10 pages).

Brief Communication in European Patent No. 2828386 dated Jan. 10, 2023 (6 pages).

Brief Communication in European Patent No. 2828386 dated Feb. 7, 2023 (2 pages).

Decision of Opposition Division in European Patent No. 2828386 dated Apr. 26, 2023 (25 pages).

Commencement of proceedings before the Board of Appeal in European Patent No. 2828386 dated May 23, 2023 (2 pages).

Reply filed by Opponent 2 in European Patent No. 2828386 dated Jan. 18, 2024 (58 pages).

Reply filed by Opponent 3 in European Patent No. 2828386 dated Jan. 10, 2024 (33 pages).

Summons to Oral Proceedings in European Patent No. 2828386 dated May 6, 2024 (4 pages).

EPO Communication forwarding letter of Opponent 3 in European Patent No. 2828386 dated Jun. 26, 2024 (5 pages).

Communication of the Board of Appeal in European Patent No. 2828386 dated Oct. 10, 2024 (6 pages).

EPO Communication forwarding letter of Opponent 2 in European Patent No. 2828386 dated Dec. 9, 2024 (5 pages).

EPO Communication forwarding letter of Opponent 3 in European Patent No. 2828386 dated Feb. 12, 2025 (4 pages).

Notification of Cancellation of Oral Proceedings in European Patent No. 2828386 dated Mar. 5, 2025 (1 page).

Closure of appeal proceedings in European Patent No. 2828386 dated Mar. 7, 2025 (1 page).

Gottesman, S., "Dicing defence in bacteria," Nature, vol. 471, pp. 588-589 (Mar. 2011).

Bhaya, D et al., "CRISPR-Cas Systems in Bacteria and Archaea: Versatile Small RNAs for Adaptive Defense and Regulation," Ann. Rev. Genet., vol. 45, pp. 273-297 (Dec. 2011).

Barrangou, R et al., "CRISPR: New Horizons in Phage Resistance and Strain Identification," Annu. Rev. Food Sci. Tehnol., vol. 13, pp. 143-162 (2012); first published online Dec. 20, 2011.

Young, J.C. et al., "Phage-Induced Expression of CRISPR-Associated Proteins is Revealed by Shotgun Proteomics in *Streptococcus thermophilus,*" PLoS One, vol. 7, e38077 (May 2012) (12 pages).

Le Rhun, A et al., "Small RNAs in streptococci," RNA Biology, vol. 9, pp. 414-426 (Apr. 2012).

Carroll, D., "Genome Engineering With Zinc-Finger Nucleases," Genetics, vol. 188, pp. 773-782 (Aug. 2011).

Transcript of minutes 8:00 to 13:00 of oral iGEM 2011 presentation of the ASU team, Oct. 9-10, 2011 (2 pages).

(56)        References Cited

OTHER PUBLICATIONS

Guglielmi, G., "Kavli prize recognizes scooped biochemist," Nature, vol. 558, pp. 17-18 (Jun. 2018).

Richardson, C.D. et al., "CRISPR-Cas9 genome editing in human cells occurs vis the Fanconi anemia pathway," Nature Genetics, vol. 50, pp. 1132-1139 (Aug. 2018).

IGEM2011 information archived, 2011 (33 pages).

ASU—Poster (iGEM 2011 Regional Jamboree Americas Oct. 9-10, 2011) (1 page).

ASU—Slide show of oral presentation at iGEM 2011 Regional Jamboree Americas Oct. 9-10, 2011 (46 pages).

IGEM2011 schedule information Oct. 9-10, 2011 (8 pages).

ASU Team Wiki—Home and Project webpages, 2011 (41 pages).

IGEM 2011—Requirements for Team Wikis, 2011 (1 page).

ASU Team Wiki—User Contributions, 2011 (4 pages).

ASU Team Wiki—Revision History Subproject L. innocua, plasmid map, applications, Sep. 2011 (25 pages).

Barrangou, R et al., "CRISPR Provides Acquired Resistance Against Viruses in Prokaryotes," Science, vol. 315, pp. 1709-1712 (Mar. 2007).

Leenay, R.T. et al., "Identifying and Visualizing Functional PAM Diversity across CRISPR-Cas Systems," Molecular Cell, pp. 137-147 (Apr. 2016).

Brouns, S.J.J., "A Swiss Army Knife of Immunity," Science, vol. 337, pp. 808-809 (Aug. 2012).

Carroll, D., "A CRISPR Approach to Gene Targeting," vol. 20, pp. 1658-1660 (Sep. 2012).

Richter, C. et al., "Function and Regulation of Clustered Regularly Interspaced Short Palindromic Repeats (CRISPR) / CRISPR Associated (Cas) Systems," Viruses, vol. 4, pp. 2291-2311 (Oct. 2012).

Sun, M. et al., "CRISPR-Cas9 and its application in medical field," J. Shenyang Pharm. Univ., vol. 12, pp. 1145-1154 (2019), abstract.

Wang, W. et al., "The Progress of CRISPR/Cas9 System and Its Application in Animal Genetic Engineering," Acta Veterinaria et Zootechnica Sinica, vol. 47, No. 7, pp. 1299-1305 (2016), abstract.

time

K1    M1    (+) strand    K2    M2    (-) strand 37 nt (-) strand
5'-GCTCGAATTG AAATTCTAAACGCTAAAGAGGAAGAGG ACA TGGTG AATTCGTAAT-3'
3'-CGAGCTTAAC TTTAAGATTTGCGATTTCTCCTTCTCC TGT ACCAC TTAAGCATTA-5'
            (+) strand 18 nt

SEQUENCE LISTING

Sequence total quantity: 69
SEQ ID NO: 1          moltype = AA  length = 1409
FEATURE               Location/Qualifiers

```
source                   1..1409
                         mol_type = protein
                         organism = Streptococcus thermophilus
SEQUENCE: 1
MLFNKCIIIS INLDFSNKEK CMTKPYSIGL DIGTNSVGWA VITDNYKVPS KKMKVLGNTS   60
KKYIKKNLLG VLLFDSGITA EGRRLKRTAR RRYTRRRNRI LYLQEIFSTE MATLDDAFFQ  120
RLDDSFLVPD DKRDSKYPIF GNLVEEKVYH DEFPTIYHLR KYLADSTKKA DLRLVYLALA  180
HMIKYRGHFL IEGEFNSKNN DIQKNFQDFL DTYNAIFESD LSLENSKQLE EIVKDKISKL  240
EKKDRILKLF PGEKNSGIFS EFLKLIVGNQ ADFRKCFNLD EKASLHFSKE SYDEDLETLL  300
GYIGDDYSDV FLKAKKLYDA ILLSGFLTVT DNETEAPLSS AMIKRYNEHK EDLALLKEYI  360
RNISLKTYNE VFKDDTKNGY AGYIDGKTNQ EDFYVYLKNL LAEFEGADYF LEKIDREDFL  420
RKQRTFDNGS IPYQIHLQEM RAILDKQAKF YPFLAKNKER IEKILTFRIP YYVGPLARGN  480
SDFAWSIRKR NEKITPWNFE DVIDKESSAE AFINRMTSFD LYLPEEKVLP KHSLLYETFN  540
VYNELTKVRF IAESMRDYQF LDSKQKKDIV RLYFKDKRKV TDKDIIEYLH AIYGYDGIEL  600
KGIEKQFNSS LSTYHDLLNI INDKEFLDDS SNEAIIEEII HTLTIFEDRE MIKQRLSKFE  660
NIFDKSVLKK LSRRHYTGWG KLSAKLINGI RDEKSGNTIL DYLIDDGISN RNFMQLIHDD  720
ALSFKKKIQK AQIIGDEDKG NIKEVVKSLP GSPAIKKGIL QSIKIVDELV KVMGGRKPES  780
IVVEMARENQ YTNQGKSNSQ QRLKRLEKSL KELGSKILKE NIPAKLSKID NNALQNDRLY  840
LYYLQNGKDM YTGDDLDIDR LSNYDIDHII PQAFLKDNSI DNKVLVSSAS NRGKSDDFPS  900
LEVVKKRKTF WYQLLSKLI SQRKFDNLTK AERGGLLPED KAGFIQRQLV ETRQITKHVA  960
RLLDEKFNNK KDENNRAVRT VKIITLKSTL VSQFRKDFEL YKVREINDFH HAHDAYLNAV 1020
IASALLKKYP KLEPEFVYGD YPKYNSFRER KSATEKVYFY SNIMNIFKKS ISLADGRVIE 1080
RPLIEVNEET GESVWNKESD LATVRRVLSY PQVNVVKKVE EQNHGLDRGK PKGLFNANLS 1140
SKPKPNSNEN LVGAKEYLDP KKYGGYAGIS NSFAVLVKGT IEKGAKKKIT NVLEFQGISI 1200
LDRINYRKDK LNFLLEKGYK DIELIIELPK YSLFELSDGS RRMLASILST NNKRGEIHKG 1260
NQIFLSQKFV KLLYHAKRIS NTINENHRKY VENHKKEFEE LFYYILEFNE NYVGAKKNGK 1320
LLNSAFQSWQ NHSIDELCSS FIGPTGSERK GLFELTSRGS AADFEFLGVK IPRYRDYTPS 1380
SLLKDATLIH QSVTGLYETR IDLAKLGEG                                  1409

SEQ ID NO: 2             moltype = AA  length = 1409
FEATURE                  Location/Qualifiers
source                   1..1409
                         mol_type = protein
                         organism = Streptococcus thermophilus
SEQUENCE: 2
MLFNKCIIIS INLDFSNKEK CMTKPYSIGL AIGTNSVGWA VITDNYKVPS KKMKVLGNTS   60
KKYIKKNLLG VLLFDSGITA EGRRLKRTAR RRYTRRRNRI LYLQEIFSTE MATLDDAFFQ  120
RLDDSFLVPD DKRDSKYPIF GNLVEEKVYH DEFPTIYHLR KYLADSTKKA DLRLVYLALA  180
HMIKYRGHFL IEGEFNSKNN DIQKNFQDFL DTYNAIFESD LSLENSKQLE EIVKDKISKL  240
EKKDRILKLF PGEKNSGIFS EFLKLIVGNQ ADFRKCFNLD EKASLHFSKE SYDEDLETLL  300
GYIGDDYSDV FLKAKKLYDA ILLSGFLTVT DNETEAPLSS AMIKRYNEHK EDLALLKEYI  360
RNISLKTYNE VFKDDTKNGY AGYIDGKTNQ EDFYVYLKNL LAEFEGADYF LEKIDREDFL  420
RKQRTFDNGS IPYQIHLQEM RAILDKQAKF YPFLAKNKER IEKILTFRIP YYVGPLARGN  480
SDFAWSIRKR NEKITPWNFE DVIDKESSAE AFINRMTSFD LYLPEEKVLP KHSLLYETFN  540
VYNELTKVRF IAESMRDYQF LDSKQKKDIV RLYFKDKRKV TDKDIIEYLH AIYGYDGIEL  600
KGIEKQFNSS LSTYHDLLNI INDKEFLDDS SNEAIIEEII HTLTIFEDRE MIKQRLSKFE  660
NIFDKSVLKK LSRRHYTGWG KLSAKLINGI RDEKSGNTIL DYLIDDGISN RNFMQLIHDD  720
ALSFKKKIQK AQIIGDEDKG NIKEVVKSLP GSPAIKKGIL QSIKIVDELV KVMGGRKPES  780
IVVEMARENQ YTNQGKSNSQ QRLKRLEKSL KELGSKILKE NIPAKLSKID NNALQNDRLY  840
LYYLQNGKDM YTGDDLDIDR LSNYDIDHII PQAFLKDNSI DNKVLVSSAS NRGKSDDFPS  900
LEVVKKRKTF WYQLLSKLI SQRKFDNLTK AERGGLLPED KAGFIQRQLV ETRQITKHVA  960
RLLDEKFNNK KDENNRAVRT VKIITLKSTL VSQFRKDFEL YKVREINDFH HAHDAYLNAV 1020
IASALLKKYP KLEPEFVYGD YPKYNSFRER KSATEKVYFY SNIMNIFKKS ISLADGRVIE 1080
RPLIEVNEET GESVWNKESD LATVRRVLSY PQVNVVKKVE EQNHGLDRGK PKGLFNANLS 1140
SKPKPNSNEN LVGAKEYLDP KKYGGYAGIS NSFAVLVKGT IEKGAKKKIT NVLEFQGISI 1200
LDRINYRKDK LNFLLEKGYK DIELIIELPK YSLFELSDGS RRMLASILST NNKRGEIHKG 1260
NQIFLSQKFV KLLYHAKRIS NTINENHRKY VENHKKEFEE LFYYILEFNE NYVGAKKNGK 1320
LLNSAFQSWQ NHSIDELCSS FIGPTGSERK GLFELTSRGS AADFEFLGVK IPRYRDYTPS 1380
SLLKDATLIH QSVTGLYETR IDLAKLGEG                                  1409

SEQ ID NO: 3             moltype = AA  length = 1409
FEATURE                  Location/Qualifiers
source                   1..1409
                         mol_type = protein
                         organism = Streptococcus thermophilus
SEQUENCE: 3
MLFNKCIIIS INLDFSNKEK CMTKPYSIGL DIGTNSVGWA VITDNYKVPS KKMKVLGNTS   60
KKYIKKNLLG VLLFDSGITA EGRRLKRTAR RRYTRRRNRI LYLQEIFSTE MATLDDAFFQ  120
RLDDSFLVPD DKRDSKYPIF GNLVEEKVYH DEFPTIYHLR KYLADSTKKA DLRLVYLALA  180
HMIKYRGHFL IEGEFNSKNN DIQKNFQDFL DTYNAIFESD LSLENSKQLE EIVKDKISKL  240
EKKDRILKLF PGEKNSGIFS EFLKLIVGNQ ADFRKCFNLD EKASLHFSKE SYDEDLETLL  300
GYIGDDYSDV FLKAKKLYDA ILLSGFLTVT DNETEAPLSS AMIKRYNEHK EDLALLKEYI  360
RNISLKTYNE VFKDDTKNGY AGYIDGKTNQ EDFYVYLKNL LAEFEGADYF LEKIDREDFL  420
RKQRTFDNGS IPYQIHLQEM RAILDKQAKF YPFLAKNKER IEKILTFRIP YYVGPLARGN  480
SDFAWSIRKR NEKITPWNFE DVIDKESSAE AFINRMTSFD LYLPEEKVLP KHSLLYETFN  540
VYNELTKVRF IAESMRDYQF LDSKQKKDIV RLYFKDKRKV TDKDIIEYLH AIYGYDGIEL  600
KGIEKQFNSS LSTYHDLLNI INDKEFLDDS SNEAIIEEII HTLTIFEDRE MIKQRLSKFE  660
NIFDKSVLKK LSRRHYTGWG KLSAKLINGI RDEKSGNTIL DYLIDDGISN RNFMQLIHDD  720
ALSFKKKIQK AQIIGDEDKG NIKEVVKSLP GSPAIKKGIL QSIKIVDELV KVMGGRKPES  780
```

```
IVVEMARENQ YTNQGKSNSQ QRLKRLEKSL KELGSKILKE NIPAKLSKID NNALQNDRLY   840
LYYLQNGKDM YTGDDLDIDR LSNYDIDHII PQAFLKDNSI DNKVLVSSAS ARGKSDDFPS   900
LEVVKKRKTF WYQLLKSKLI SQRKFDNLTK AERGGLLPED KAGFIQRQLV ETRQITKHVA   960
RLLDEKFNNK KDENNRAVRT VKIITLKSTL VSQFRKDFEL YKVREINDFH HAHDAYLNAV  1020
IASALLKKYP KLEPEFVYGD YPKYNSFRER KSATEKVYFY SNIMIFKKS  ISLADGRVIE  1080
RPLIEVNEET GESVWNKESD LATVRRVLSY PQVNVVKKVE EQNHGLDRGK PKGLFNANLS  1140
SKPKPNSNEN LVGAKEYLDP KKYGGYAGIS NSFAVLVKGT IEKGAKKKIT NVLEFQGISI  1200
LDRINYRKDK LNFLLEKGYK DIELIIELPK YSLFELSDGS RRMLASILST NNKRGEIHKG  1260
NQIFLSQKFV KLLYHAKRIS NTINENHRKY VENHKKEFEE LFYYILEFNE NYVGAKKNGK  1320
LLNSAFQSWQ NHSIDELCSS FIGPTGSERK GLFELTSRGS AADFEFLGVK IPRYRDYTPS  1380
SLLKDATLIH QSVTGLYETR IDLAKLGEG                                   1409

SEQ ID NO: 4            moltype = AA   length = 1409
FEATURE                 Location/Qualifiers
source                  1..1409
                        mol_type = protein
                        organism = Streptococcus thermophilus
SEQUENCE: 4
MLFNKCIIIS INLDFSNKEK CMTKPYSIGL DIGTNSVGWA VITDNYKVPS KKMKVLGNTS   60
KKYIKKNLLG VLLFDSGITA EGRRLKRTAR RRYTRRRNRI LYLQEIFSTE MATLDDAFFQ  120
RLDDSFLVPD DKRDSKYPIF GNLVEEKVYH DEFPTIYHLR KYLADSTKKA DLRLVYLALA  180
HMIKYRGHFL IEGEFNSKNN DIQKNFQDFL DTYNAIFESD LSLENSKQLE EIVKDKISKL  240
EKKDRILKLF PGEKNSGIFS EFLKLIVGNQ ADFRKCFNLD EKASLHFSKE SYDEDLETLL  300
GYIGDDYSDV FLKAKKLYDA ILLSGFLTVT DNETEAPLSS AMIKRYNEHK EDLALLKEYI  360
RNISLKTYNE VFKDDTKNGY AGYIDGKTNQ EDFYVYLKNL LAEFEGADYF LEKIDREDFL  420
RKQRTFDNGS IPYQIHLQEM RAILDKQAKF YPFLAKNKER IEKILTFRIP YYVGPLARGN  480
SDFAWSIRKR NEKITPWNFE DVIDKESSAE AFINRMTSFD LYLPEEKVLP KHSLLYETFN  540
VYNELTKVRF IAESMRDYQF LDSKQKKDIV RLYFKDKRKV TDKDIIEYLH AIYGYDGIEL  600
KGIEKQFNSS LSTYHDLLNI INDKEFLDDS SNEAIIEEII HTLTIFEDRE MIKQRLSKFE  660
NIFDKSVLKK LSRRHYTGWG KLSAKLINGI RDEKSGNTIL DYLIDDGISN RNFMQLIHDD  720
ALSFKKKIQK AQIIGDEDKG NIKEVVKSLP GSPAIKKGIL QSIKIVDELV KVMGGRKPES  780
IVVEMARENQ YTNQGKSNSQ QRLKRLEKSL KELGSKILKE NIPAKLSKID NNALQNDRLY   840
LYYLQNGKDM YTGDDLDIDR LSNYDIDAII PQAFLKDNSI DNKVLVSSAS NRGKSDDFPS   900
LEVVKKRKTF WYQLLKSKLI SQRKFDNLTK AERGGLLPED KAGFIQRQLV ETRQITKHVA   960
RLLDEKFNNK KDENNRAVRT VKIITLKSTL VSQFRKDFEL YKVREINDFH HAHDAYLNAV  1020
IASALLKKYP KLEPEFVYGD YPKYNSFRER KSATEKVYFY SNIMNIFKKS ISLADGRVIE  1080
RPLIEVNEET GESVWNKESD LATVRRVLSY PQVNVVKKVE EQNHGLDRGK PKGLFNANLS  1140
SKPKPNSNEN LVGAKEYLDP KKYGGYAGIS NSFAVLVKGT IEKGAKKKIT NVLEFQGISI  1200
LDRINYRKDK LNFLLEKGYK DIELIIELPK YSLFELSDGS RRMLASILST NNKRGEIHKG  1260
NQIFLSQKFV KLLYHAKRIS NTINENHRKY VENHKKEFEE LFYYILEFNE NYVGAKKNGK  1320
LLNSAFQSWQ NHSIDELCSS FIGPTGSERK GLFELTSRGS AADFEFLGVK IPRYRDYTPS  1380
SLLKDATLIH QSVTGLYETR IDLAKLGEG                                   1409

SEQ ID NO: 5            moltype = RNA   length = 102
FEATURE                 Location/Qualifiers
source                  1..102
                        mol_type = unassigned RNA
                        organism = Streptococcus thermophilus
SEQUENCE: 5
taataataat tgtggtttga aaccattcga aacaacacag cgagttaaaa taaggcttag   60
tccgtactca acttgaaaag gtggcaccga ttcggtgttt tt                     102

SEQ ID NO: 6            moltype = RNA   length = 78
FEATURE                 Location/Qualifiers
source                  1..78
                        mol_type = unassigned RNA
                        organism = Streptococcus thermophilus
SEQUENCE: 6
gggcgaaaca acacagcgag ttaaaataag gcttagtccg tactcaactt gaaaaggtgg   60
caccgattcg gtgtttt                                                 78

SEQ ID NO: 7            moltype = RNA   length = 42
FEATURE                 Location/Qualifiers
misc_feature            1..42
                        note = source = /note="Description of Artificial Sequence:
                         Synthetic oligonucleotide"
source                  1..42
                        mol_type = other RNA
                        organism = synthetic construct
SEQUENCE: 7
cgctaaagag gaagaggaca gttttagagc tgtgttgttt cg                     42

SEQ ID NO: 8            moltype = RNA   length = 150
FEATURE                 Location/Qualifiers
misc_feature            1..150
                        note = source = /note="Description of Artificial Sequence:
                         Synthetic polynucleotide"
source                  1..150
                        mol_type = other RNA
```

```
                    organism = synthetic construct
SEQUENCE: 8
gggtagaaaa gatatcctac gaggttttag agctgtgttg tttcgaatgg ttccaaaaca   60
aattctaaac gctaaagagg aagaggacag ttttagagct gtgttgtttc gaatggttcc   120
aaaactactg ctgtattagc ttggttgttg                                     150

SEQ ID NO: 9              moltype = DNA  length = 150
FEATURE                   Location/Qualifiers
misc_feature              60..89
                          note = source = /note="Description of Artificial Sequence:
                           Synthetic oligonucleotide"
                          note = DNA
misc_feature              1..59
                          note = source = /note="Description of Combined DNA/RNA
                           Molecule: Synthetic oligonucleotide"
                          note = RNA
source                    1..150
                          mol_type = other DNA
                          organism = synthetic construct
misc_feature              90..150
                          note = RNA
SEQUENCE: 9
gggtagaaaa gatatcctac gaggttttag agctgtgttg tttcgaatgg ttccaaaact   60
gtcatgataa taatggtttc ttagacgtcg ttttagagct gtgttgtttc gaatggttcc   120
aaaactactg ctgtattagc ttggttgttg                                     150

SEQ ID NO: 10             moltype = DNA  length = 150
FEATURE                   Location/Qualifiers
misc_feature              60..89
                          note = DNA
misc_feature              1..59
                          note = RNA
source                    1..150
                          mol_type = other DNA
                          organism = synthetic construct
misc_feature              90..150
                          note = RNA
SEQUENCE: 10
gggtagaaaa gatatcctac gaggttttag agctgtgttg tttcgaatgg ttccaaaaca   60
cgagccggaa gcataaagtg taaagcctgg ttttagagct gtgttgtttc gaatggttcc   120
aaaactactg ctgtattagc ttggttgttg                                     150

SEQ ID NO: 11             moltype = DNA  length = 150
FEATURE                   Location/Qualifiers
misc_feature              1..59
                          note = RNA
misc_feature              60..89
                          note = DNA
source                    1..150
                          mol_type = other DNA
                          organism = synthetic construct
misc_feature              90..150
                          note = RNA
SEQUENCE: 11
gggtagaaaa gatatcctac gaggttttag agctgtgttg tttcgaatgg ttccaaaact   60
caagggagaa tagaggctct cgttgcattg ttttagagct gtgttgtttc gaatggttcc   120
aaaactactg ctgtattagc ttggttgttg                                     150

SEQ ID NO: 12             moltype = DNA  length = 150
FEATURE                   Location/Qualifiers
misc_feature              60..89
                          note = DNA
misc_feature              1..59
                          note = RNA
source                    1..150
                          mol_type = other DNA
                          organism = synthetic construct
misc_feature              90..150
                          note = RNA
SEQUENCE: 12
gggtagaaaa gatatcctac gaggttttag agctgtgttg tttcgaatgg ttccaaaacc   60
gggagggaag ctgcatgatg cgatgttatg ttttagagct gtgttgtttc gaatggttcc   120
aaaactactg ctgtattagc ttggttgttg                                     150

SEQ ID NO: 13             moltype = RNA  length = 42
FEATURE                   Location/Qualifiers
misc_feature              1..42
                          note = source = /note="Description of Artificial Sequence:
                           Synthetic oligonucleotide"
```

-continued

```
source                   1..42
                         mol_type = other RNA
                         organism = synthetic construct
SEQUENCE: 13
gctcccgggg ctcgatgaag gttttagagc tgtgttgttt cg                          42

SEQ ID NO: 14            moltype = RNA   length = 42
FEATURE                  Location/Qualifiers
misc_feature             1..42
                         note = source = /note="Description of Artificial Sequence:
                          Synthetic oligonucleotide"
source                   1..42
                         mol_type = other RNA
                         organism = synthetic construct
SEQUENCE: 14
tgaatcgtga aatctgctca gttttagagc tgtgttgttt cg                          42

SEQ ID NO: 15            moltype = RNA   length = 42
FEATURE                  Location/Qualifiers
misc_difference          1..20
misc_feature             1..42
                         note = source = /note="Description of Artificial Sequence:
                          Synthetic oligonucleotide"
source                   1..42
                         mol_type = other RNA
                         organism = synthetic construct
SEQUENCE: 15
nnnnnnnnnn nnnnnnnnnn gttttagagc tgtgttgttt cg                          42

SEQ ID NO: 16            moltype = DNA   length = 29
FEATURE                  Location/Qualifiers
misc_feature             1..29
                         note = source = /note="Description of Artificial Sequence:
                          Synthetic oligonucleotide"
source                   1..29
                         mol_type = other DNA
                         organism = synthetic construct
SEQUENCE: 16
ccacccagca aaattcggtt ttctggctg                                         29

SEQ ID NO: 17            moltype = DNA   length = 36
FEATURE                  Location/Qualifiers
misc_feature             1..36
                         note = source = /note="Description of Artificial Sequence:
                          Synthetic primer"
source                   1..36
                         mol_type = other DNA
                         organism = synthetic construct
SEQUENCE: 17
taatacgact cactataggg taccgagctc gaattg                                 36

SEQ ID NO: 18            moltype = DNA   length = 31
FEATURE                  Location/Qualifiers
misc_feature             1..31
                         note = source = /note="Description of Artificial Sequence:
                          Synthetic primer"
source                   1..31
                         mol_type = other DNA
                         organism = synthetic construct
SEQUENCE: 18
gggaaacagc tatgaccatg attacgaatt c                                      31

SEQ ID NO: 19            moltype = DNA   length = 31
FEATURE                  Location/Qualifiers
misc_feature             1..31
                         note = source = /note="Description of Artificial Sequence:
                          Synthetic primer"
source                   1..31
                         mol_type = other DNA
                         organism = synthetic construct
SEQUENCE: 19
gggtaccgag ctcgaattga aattctaaac g                                      31

SEQ ID NO: 20            moltype = DNA   length = 43
FEATURE                  Location/Qualifiers
misc_feature             1..43
                         note = source = /note="Description of Artificial Sequence:
                          Synthetic primer"
source                   1..43
```

-continued

```
                          mol_type = other DNA
                          organism = synthetic construct
SEQUENCE: 20
taatacgact cactataggg aaacagctat gaccatgatt acg                              43

SEQ ID NO: 21           moltype = DNA   length = 38
FEATURE                 Location/Qualifiers
misc_feature            1..38
                        note = source = /note="Description of Artificial Sequence:
                         Synthetic primer"
source                  1..38
                        mol_type = other DNA
                        organism = synthetic construct
SEQUENCE: 21
acgtctcaaa tgttgtttaa taagtgtata ataatttc                                   38

SEQ ID NO: 22           moltype = DNA   length = 29
FEATURE                 Location/Qualifiers
misc_feature            1..29
                        note = source = /note="Description of Artificial Sequence:
                         Synthetic primer"
source                  1..29
                        mol_type = other DNA
                        organism = synthetic construct
SEQUENCE: 22
acgtctccgc gctaccctct cctagtttg                                             29

SEQ ID NO: 23           moltype = AA   length = 6
FEATURE                 Location/Qualifiers
REGION                  1..6
                        note = source = /note="Description of Artificial Sequence:
                         Synthetic 6xHis tag"
source                  1..6
                        mol_type = protein
                        organism = synthetic construct
SEQUENCE: 23
HHHHHH                                                                       6

SEQ ID NO: 24           moltype = DNA   length = 34
FEATURE                 Location/Qualifiers
misc_feature            1..34
                        note = source = /note="Description of Artificial Sequence:
                         Synthetic primer"
source                  1..34
                        mol_type = other DNA
                        organism = synthetic construct
SEQUENCE: 24
acgtctcaca tgactaagcc atactcaatt ggac                                       34

SEQ ID NO: 25           moltype = DNA   length = 27
FEATURE                 Location/Qualifiers
misc_feature            1..27
                        note = source = /note="Description of Artificial Sequence:
                         Synthetic primer"
source                  1..27
                        mol_type = other DNA
                        organism = synthetic construct
SEQUENCE: 25
actcgagacc ctctcctagt ttggcaa                                               27

SEQ ID NO: 26           moltype = DNA   length = 23
FEATURE                 Location/Qualifiers
misc_feature            1..23
                        note = source = /note="Description of Artificial Sequence:
                         Synthetic primer"
source                  1..23
                        mol_type = other DNA
                        organism = synthetic construct
SEQUENCE: 26
gaccacttat tgaggtaaat gag                                                   23

SEQ ID NO: 27           moltype = DNA   length = 28
FEATURE                 Location/Qualifiers
misc_feature            1..28
                        note = source = /note="Description of Artificial Sequence:
                         Synthetic primer"
source                  1..28
                        mol_type = other DNA
                        organism = synthetic construct
```

-continued

```
SEQUENCE: 27
caaaccagga tccaagctaa tacagcag                                              28

SEQ ID NO: 28             moltype = DNA  length = 42
FEATURE                   Location/Qualifiers
misc_feature              1..42
                          note = source = /note="Description of Artificial Sequence:
                           Synthetic oligonucleotide"
source                    1..42
                          mol_type = other DNA
                          organism = synthetic construct
SEQUENCE: 28
tcgaaacaac acagctctaa aactgtcctc ttcctcttta gc                              42

SEQ ID NO: 29             moltype = DNA  length = 21
FEATURE                   Location/Qualifiers
misc_feature              1..21
                          note = source = /note="Description of Artificial Sequence:
                           Synthetic primer"
source                    1..21
                          mol_type = other DNA
                          organism = synthetic construct
SEQUENCE: 29
ccgcatcagg cgccattcgc c                                                     21

SEQ ID NO: 30             moltype = DNA  length = 22
FEATURE                   Location/Qualifiers
misc_feature              1..22
                          note = source = /note="Description of Artificial Sequence:
                           Synthetic primer"
source                    1..22
                          mol_type = other DNA
                          organism = synthetic construct
SEQUENCE: 30
gcgaggaagc ggaagagcgc cc                                                    22

SEQ ID NO: 31             moltype = DNA  length = 55
FEATURE                   Location/Qualifiers
misc_feature              1..55
                          note = source = /note="Description of Artificial Sequence:
                           Synthetic oligonucleotide"
source                    1..55
                          mol_type = other DNA
                          organism = synthetic construct
SEQUENCE: 31
gctcgaattg aaattctaaa cgctaaagag gaagaggaca tggtgaattc gtaat               55

SEQ ID NO: 32             moltype = DNA  length = 50
FEATURE                   Location/Qualifiers
misc_feature              1..50
                          note = source = /note="Description of Artificial Sequence:
                           Synthetic oligonucleotide"
source                    1..50
                          mol_type = other DNA
                          organism = synthetic construct
SEQUENCE: 32
gctcgaattg aaattctaaa cgctaaagag gaagaggaca aattcgtaat                      50

SEQ ID NO: 33             moltype = DNA  length = 55
FEATURE                   Location/Qualifiers
misc_feature              1..55
                          note = source = /note="Description of Artificial Sequence:
                           Synthetic oligonucleotide"
source                    1..55
                          mol_type = other DNA
                          organism = synthetic construct
SEQUENCE: 33
gctcgaattg tactgctgta ttagcttggt tgttggtttg tggtgaattc gtaat               55

SEQ ID NO: 34             moltype = DNA  length = 55
FEATURE                   Location/Qualifiers
misc_feature              1..55
                          note = source = /note="Description of Artificial Sequence:
                           Synthetic oligonucleotide"
source                    1..55
                          mol_type = other DNA
                          organism = synthetic construct
SEQUENCE: 34
attacgaatt caccatgtcc tcttcctctt tagcgtttag aatttcaatt cgagc               55
```

-continued

```
SEQ ID NO: 35              moltype = DNA   length = 50
FEATURE                    Location/Qualifiers
misc_feature               1..50
                           note = source = /note="Description of Artificial Sequence:
                           Synthetic oligonucleotide"
source                     1..50
                           mol_type = other DNA
                           organism = synthetic construct
SEQUENCE: 35
attacgaatt tgtcctcttc ctctttagcg tttagaattt caattcgagc              50

SEQ ID NO: 36              moltype = DNA   length = 55
FEATURE                    Location/Qualifiers
misc_feature               1..55
                           note = source = /note="Description of Artificial Sequence:
                           Synthetic oligonucleotide"
source                     1..55
                           mol_type = other DNA
                           organism = synthetic construct
SEQUENCE: 36
attacgaatt caccacaaac caacaaccaa gctaatacag cagtacaatt cgagc        55

SEQ ID NO: 37              moltype = DNA   length = 55
FEATURE                    Location/Qualifiers
misc_feature               1..55
                           note = source = /note="Description of Artificial Sequence:
                           Synthetic oligonucleotide"
source                     1..55
                           mol_type = other DNA
                           organism = synthetic construct
SEQUENCE: 37
gctcgaattg aaattctaaa cgctaaagag gaagaggaca tggtgaattc gtaat        55

SEQ ID NO: 38              moltype = DNA   length = 45
FEATURE                    Location/Qualifiers
misc_feature               1..45
                           note = source = /note="Description of Artificial Sequence:
                           Synthetic oligonucleotide"
source                     1..45
                           mol_type = other DNA
                           organism = synthetic construct
SEQUENCE: 38
gctcgaattg cgctaaagag gaagaggaca tggtgaattc gtaat                   45

SEQ ID NO: 39              moltype = DNA   length = 55
FEATURE                    Location/Qualifiers
misc_feature               1..55
                           note = source = /note="Description of Artificial Sequence:
                           Synthetic oligonucleotide"
source                     1..55
                           mol_type = other DNA
                           organism = synthetic construct
SEQUENCE: 39
gctcgaattg ccacccagca aaattcggtt ttctggctga tggtgaattc gtaat        55

SEQ ID NO: 40              moltype = DNA   length = 41
FEATURE                    Location/Qualifiers
misc_feature               1..41
                           note = source = /note="Description of Artificial Sequence:
                           Synthetic primer"
source                     1..41
                           mol_type = other DNA
                           organism = synthetic construct
SEQUENCE: 40
taatacgact cactataggg tagaaaagat atcctacgag g                       41

SEQ ID NO: 41              moltype = DNA   length = 23
FEATURE                    Location/Qualifiers
misc_feature               1..23
                           note = source = /note="Description of Artificial Sequence:
                           Synthetic primer"
source                     1..23
                           mol_type = other DNA
                           organism = synthetic construct
SEQUENCE: 41
caacaaccaa gctaatacag cag                                           23

SEQ ID NO: 42              moltype = DNA   length = 22
```

-continued

```
FEATURE              Location/Qualifiers
misc_feature         1..22
                     note = source = /note="Description of Artificial Sequence:
                      Synthetic primer"
source               1..22
                     mol_type = other DNA
                     organism = synthetic construct
SEQUENCE: 42
aaaaacaccg aatcggtgcc ac                                           22

SEQ ID NO: 43        moltype = DNA  length = 48
FEATURE              Location/Qualifiers
misc_feature         1..48
                     note = source = /note="Description of Artificial Sequence:
                      Synthetic primer"
source               1..48
                     mol_type = other DNA
                     organism = synthetic construct
SEQUENCE: 43
taatacgact cactataggg taataataat tgtggtttga aaccattc               48

SEQ ID NO: 44        moltype = RNA  length = 73
FEATURE              Location/Qualifiers
source               1..73
                     mol_type = unassigned RNA
                     organism = Streptococcus thermophilus
SEQUENCE: 44
gggcgaaaca acacagcgag ttaaaataag gcttagtccg tactcaactt gaaaaggtgg  60
caccgattcg gtg                                                     73

SEQ ID NO: 45        moltype = RNA  length = 68
FEATURE              Location/Qualifiers
source               1..68
                     mol_type = unassigned RNA
                     organism = Streptococcus thermophilus
SEQUENCE: 45
gggcgaaaca acacagcgag ttaaaataag gcttagtccg tactcaactt gaaaaggtgg  60
caccgatt                                                           68

SEQ ID NO: 46        moltype = RNA  length = 63
FEATURE              Location/Qualifiers
source               1..63
                     mol_type = unassigned RNA
                     organism = Streptococcus thermophilus
SEQUENCE: 46
gggcgaaaca acacagcgag ttaaaataag gcttagtccg tactcaactt gaaaaggtgg  60
cac                                                                63

SEQ ID NO: 47        moltype = RNA  length = 58
FEATURE              Location/Qualifiers
source               1..58
                     mol_type = unassigned RNA
                     organism = Streptococcus thermophilus
SEQUENCE: 47
gggcgaaaca acacagcgag ttaaaataag gcttagtccg tactcaactt gaaaaggt    58

SEQ ID NO: 48        moltype = RNA  length = 53
FEATURE              Location/Qualifiers
source               1..53
                     mol_type = unassigned RNA
                     organism = Streptococcus thermophilus
SEQUENCE: 48
gggcgaaaca acacagcgag ttaaaataag gcttagtccg tactcaactt gaa         53

SEQ ID NO: 49        moltype = RNA  length = 48
FEATURE              Location/Qualifiers
source               1..48
                     mol_type = unassigned RNA
                     organism = Streptococcus thermophilus
SEQUENCE: 49
gggcgaaaca acacagcgag ttaaaataag gcttagtccg tactcaac              48

SEQ ID NO: 50        moltype = DNA  length = 36
FEATURE              Location/Qualifiers
source               1..36
                     mol_type = unassigned DNA
                     organism = Streptococcus thermophilus
SEQUENCE: 50
gttttagagc tgtgttgttt cgaatggttc caaaac                            36
```

-continued

```
SEQ ID NO: 51              moltype = DNA   length = 36
FEATURE                    Location/Qualifiers
source                     1..36
                           mol_type = unassigned DNA
                           organism = Streptococcus pyogenes
SEQUENCE: 51
gttttagagc tatgctgttt tgaatggtcc caaaac                             36

SEQ ID NO: 52              moltype = DNA   length = 36
FEATURE                    Location/Qualifiers
source                     1..36
                           mol_type = unassigned DNA
                           organism = Streptococcus thermophilus
SEQUENCE: 52
tttaactcgc tgtgttgttt cgaatggttt caaacc                             36

SEQ ID NO: 53              moltype = DNA   length = 36
FEATURE                    Location/Qualifiers
source                     1..36
                           mol_type = unassigned DNA
                           organism = Streptococcus pyogenes
SEQUENCE: 53
tttaacttgc tatgctgttt tgaatggttc caacaa                             36

SEQ ID NO: 54              moltype = RNA   length = 42
FEATURE                    Location/Qualifiers
source                     1..42
                           mol_type = unassigned RNA
                           organism = Streptococcus pyogenes
SEQUENCE: 54
gatttcttct tgcgcttttt gttttagagc tatgctgttt tg                      42

SEQ ID NO: 55              moltype = RNA   length = 42
FEATURE                    Location/Qualifiers
source                     1..42
                           mol_type = unassigned RNA
                           organism = Streptococcus thermophilus
SEQUENCE: 55
gttcactgta cgagtactta gttttagagc tgtgttgttt cg                      42

SEQ ID NO: 56              moltype = RNA   length = 42
FEATURE                    Location/Qualifiers
source                     1..42
                           mol_type = unassigned RNA
                           organism = Streptococcus thermophilus
SEQUENCE: 56
cgctaaagag gaagaggaca gttttagagc tgtgttgttt cg                      42

SEQ ID NO: 57              moltype = DNA   length = 35
FEATURE                    Location/Qualifiers
misc_feature               1..35
                           note = source = /note="Description of Artificial Sequence:
                           Synthetic oligonucleotide"
source                     1..35
                           mol_type = other DNA
                           organism = synthetic construct
SEQUENCE: 57
aaattctaaa cgctaaagag gaagaggaca tggtg                              35

SEQ ID NO: 58              moltype = DNA   length = 18
FEATURE                    Location/Qualifiers
misc_feature               1..18
                           note = source = /note="Description of Artificial Sequence:
                           Synthetic oligonucleotide"
source                     1..18
                           mol_type = other DNA
                           organism = synthetic construct
SEQUENCE: 58
aggaagagga catggtga                                                 18

SEQ ID NO: 59              moltype = DNA   length = 10
FEATURE                    Location/Qualifiers
misc_feature               1..10
                           note = source = /note="Description of Artificial Sequence:
                           Synthetic oligonucleotide"
source                     1..10
                           mol_type = other DNA
                           organism = synthetic construct
```

-continued

```
SEQUENCE: 59
aggaagagga                                                            10

SEQ ID NO: 60           moltype = DNA   length = 10
FEATURE                 Location/Qualifiers
misc_feature            1..10
                        note = source = /note="Description of Artificial Sequence:
                         Synthetic oligonucleotide"
source                  1..10
                        mol_type = other DNA
                        organism = synthetic construct
SEQUENCE: 60
tacatggtga                                                            10

SEQ ID NO: 61           moltype = DNA   length = 35
FEATURE                 Location/Qualifiers
misc_feature            1..35
                        note = source = /note="Description of Artificial Sequence:
                         Synthetic oligonucleotide"
source                  1..35
                        mol_type = other DNA
                        organism = synthetic construct
SEQUENCE: 61
caccatgtcc tcttcctctt tagcgtttag aattt                               35

SEQ ID NO: 62           moltype = DNA   length = 32
FEATURE                 Location/Qualifiers
misc_feature            1..32
                        note = source = /note="Description of Artificial Sequence:
                         Synthetic oligonucleotide"
source                  1..32
                        mol_type = other DNA
                        organism = synthetic construct
SEQUENCE: 62
caccatgtcc tcttcctctt tagcgtttag aa                                  32

SEQ ID NO: 63           moltype = DNA   length = 28
FEATURE                 Location/Qualifiers
misc_feature            1..28
                        note = source = /note="Description of Artificial Sequence:
                         Synthetic oligonucleotide"
source                  1..28
                        mol_type = other DNA
                        organism = synthetic construct
SEQUENCE: 63
caccatgtcc tcttcctctt tagcgttt                                       28

SEQ ID NO: 64           moltype = DNA   length = 24
FEATURE                 Location/Qualifiers
misc_feature            1..24
                        note = source = /note="Description of Artificial Sequence:
                         Synthetic oligonucleotide"
source                  1..24
                        mol_type = other DNA
                        organism = synthetic construct
SEQUENCE: 64
caccatgtcc tcttcctctt tagc                                           24

SEQ ID NO: 65           moltype = DNA   length = 20
FEATURE                 Location/Qualifiers
misc_feature            1..20
                        note = source = /note="Description of Artificial Sequence:
                         Synthetic oligonucleotide"
source                  1..20
                        mol_type = other DNA
                        organism = synthetic construct
SEQUENCE: 65
caccatgtcc tcttcctctt                                                20

SEQ ID NO: 66           moltype = DNA   length = 16
FEATURE                 Location/Qualifiers
misc_feature            1..16
                        note = source = /note="Description of Artificial Sequence:
                         Synthetic oligonucleotide"
source                  1..16
                        mol_type = other DNA
                        organism = synthetic construct
SEQUENCE: 66
caccatgtcc tcttcc                                                    16
```

-continued

```
SEQ ID NO: 67          moltype = DNA  length = 55
FEATURE                Location/Qualifiers
misc_feature           1..55
                       note = source = /note="Description of Artificial Sequence:
                       Synthetic oligonucleotide"
source                 1..55
                       mol_type = other DNA
                       organism = synthetic construct
SEQUENCE: 67
attacgaatt ctccttgtcc tcttcctctt tagcgtttag aatttcaatt cgagc        55

SEQ ID NO: 68          moltype = DNA  length = 55
FEATURE                Location/Qualifiers
misc_feature           1..55
                       note = source = /note="Description of Artificial Sequence:
                       Synthetic oligonucleotide"
source                 1..55
                       mol_type = other DNA
                       organism = synthetic construct
SEQUENCE: 68
attacgaatt gtggttgtcc tcttcctctt tagcgtttag aatttcaatt cgagc        55

SEQ ID NO: 69          moltype = RNA  length = 42
FEATURE                Location/Qualifiers
misc_feature           1..42
                       note = source = /note="Description of Artificial Sequence:
                       Synthetic oligonucleotide"
source                 1..42
                       mol_type = other RNA
                       organism = synthetic construct
SEQUENCE: 69
gctaaagagg aagaggacag ttttagagct gtgttgtttc ga                      42
```

RNA-DIRECTED DNA CLEAVAGE BY THE CAS9-CRRNA COMPLEX

This application is a continuation of U.S. application Ser. No. 14/743,764, filed on Jun. 18, 2015, which is a continuation of U.S. application Ser. No. 14/385,241, filed on Sep. 15, 2014, which is the national stage entry of PCT/LT2013/000006, filed on Mar. 15, 2013, which claims priority to U.S. Provisional Application No. 61/613,373, filed on Mar. 20, 2012, and U.S. Provisional Application No. 61/625,420, filed on Apr. 17, 2012, each of which is expressly incorporated by reference herein in its entirety.

This application contains a sequence listing, submitted electronically in XML format under the filename 00171-0002-06000.xml, which is incorporated by reference herein in its entirety. The XML copy of the sequence listing was created on Dec. 14, 2022, and is 95,106 bytes in size.

BACKGROUND

Clustered Regularly Interspaced Short Palindromic Repeats (CRISPR) together with cas (CRISPR-associated) genes comprise an adaptive immune system that provides acquired resistance against invading foreign nucleic acids in bacteria and archaea (Barrangou et al., 2007. Science 315: 1709-12). CRISPR consists of arrays of short conserved repeat sequences interspaced by unique variable DNA sequences of similar size called spacers, which often originate from phage or plasmid DNA (Barrangou et al., 2007. Science 315:1709-12; Bolotin et al., 2005. Microbiology 151:2551-61; Mojica et al., 2005. J Mol Evol 60:174-82). The CRISPR-Cas system functions by acquiring short pieces of foreign DNA (spacers) which are inserted into the CRISPR region and provide immunity against subsequent exposures to phages and plasmids that carry matching sequences (Barrangou et al., 2007. Science 315:1709-12; Brouns et al., 2008. Science 321: 960-4) The CRISPR-Cas immunity is generally carried out through three stages, referred to as i) adaptation/immunization/spacer acquisition, ii) CRISPR expression/crRNA biogenesis, iii) interference/immunity. (Horvath & Barrangou, 2010. Science 327:167-70; Deveau et al., 2010. Annu Rev Microbiol. 64:475-93; Marraffini & Sontheimer, 2010. Nat Rev Genet 11, 181-90; Bhaya et al., Annu Rev Genet 45:273-97; Wiedenheft et al., 2012. Nature 482:331-338). Here, we specifically focus on the interference/immunity step which enables crRNA-mediated silencing of foreign nucleic acids.

The highly diverse CRISPR-Cas systems are categorized into three major types, which are further subdivided into ten subtypes, based on core element content and sequences (Makarova et al., 2011. Nat Rev Microbiol 9:467-77). The structural organization and function of nucleoprotein complexes involved in crRNA-mediated silencing of foreign nucleic acids differ between distinct CRISPR/Cas types (Wiedenheft et al., 2012. Nature 482:331-338). In the Type I-E system, as exemplified by *Escherichia coli*, crRNAs are incorporated into a multisubunit effector complex called Cascade (CRISPR-associated complex for antiviral defence) (Brouns et al., 2008. Science 321: 960-4), which binds to the target DNA and triggers degradation by the signature Cas3 protein (Sinkunas et al., 2011. EMBO J 30:1335-42; Beloglazova et al., 2011. EMBO J 30:616-27). In Type III CRISPR/Cas systems of *Sulfolobus solfataricus* and *Pyrococcus furiosus*, Cas RAMP module (Cmr) and crRNA complex recognize and cleave synthetic RNA in vitro (Hale et al., 2012. Mol Cell 45:292-302; Zhang et al., 2012. Mol Cell, 45:303-13) while the CRISPR/Cas system of *Staphy-*

*lococcus epidermidis* targets DNA in vivo (Marraffini & Sontheimer, Science. 322:1843-5).

RNP complexes involved in DNA silencing by Type II CRISPR/Cas systems, more specifically in the CRISPR3/Cas system of *Streptococcus thermophilus* DGCC7710 (Horvath & Barrangou, 2010. Science 327:167-70), consists of four cas genes cas9, cas1, cas2, and csn2, that are located upstream of 12 repeat-spacer units (part (A) of FIG. 1). Cas9 (formerly named cas5 or csn1) is the signature gene for Type II systems (Makarova et al., 2011. Nat Rev Microbiol 9:467-77). In the closely related *S. thermophilus* CRISPR1/Cas system, disruption of cas9 abolishes crRNA-mediated DNA interference (Barrangou et al., 2007. Science 315:1709-12). We have shown recently that the *S. thermophilus* CRISPR3/Cas system can be transferred into *Escherichia coli*, and that this heterologous system provides protection against plasmid transformation and phage infection, de novo (Sapranauskas et al., 2011. Nucleic Acids Res 39:9275-82). The interference against phage and plasmid DNA provided by *S. thermophilus* CRISPR3 requires the presence, within the target DNA, of a proto-spacer sequence complementary to the spacer-derived crRNA, and a conserved PAM (Proto-spacer Adjacent Motif) sequence, NGGNG, located immediately downstream the proto-spacer (Deveau et al., 2008. J Bacteriol 190:1390-400; Horvath et al., 2008. J Bacteriol 190:1401-12; Mojica et al., 2009. Microbiology 155:733-40). Single point mutations in the PAM or defined proto-spacer positions allow the phages or plasmids to circumvent CRISPR-mediated immunity (Deveau et al., 2008. J Bacteriol 190:1390-400; Garneau et al., 2010. Nature 468:67-71; Sapranauskas et al., 2011. Nucleic Acids Res 39:9275-82). We have established that in the heterologous system, cas9 is the sole cas gene necessary for CRISPR-encoded interference (Sapranauskas et al., 2011. Nucleic Acids Res 39:9275-82), suggesting that this protein is involved in crRNA processing and/or crRNA-mediated silencing of invasive DNA. Cas9 of *S. thermophilus* CRISPR3/Cas system is a large multi-domain protein comprised of 1,409 aa residues (Sapranauskas et al., 2011. Nucleic Acids Res 39:9275-82). It contains two nuclease domains, a RuvC-like nuclease domain near the amino terminus, and a HNH-like nuclease domain in the middle of the protein. Mutational analysis has established that interference provided in vivo by Cas9 requires both the RuvC- and HNH-motifs (Sapranauskas et al., 2011. Nucleic Acids Res 39:9275-82).

Isolation of the Cas9-crRNA complex of the *S. thermophilus* CRISPR3/Cas system as well as complex assembly in vitro from separate components and demonstration that it cleaves both synthetic oligodeoxynucleotide and plasmid DNA bearing a nucleotide sequence complementary to the crRNA, in a PAM-dependent manner, is provided. Furthermore, we provide experimental evidence that the PAM is recognized in the context of double-stranded DNA and is critical for in vitro DNA binding and cleavage. Finally, we show that the Cas9 RuvC- and HNH-active sites are responsible for the cleavage of opposite DNA strands. Taken together, our data demonstrate that the Cas9-crRNA complex functions as an RNA-guided endonuclease which uses RNA for the target site recognition and Cas9 for DNA cleavage. The simple modular organization of the Cas9-crRNA complex, where specificity for DNA targets is encoded by a small crRNA and the cleavage machinery consists of a single, multidomain Cas protein, provides a versatile platform for the engineering of universal RNA-guided DNA endonucleases. Indeed, we provide evidence that by altering the RNA sequence within the Cas9-crRNA complex, programmable endonucleases can be designed both for in vitro and in vivo applications, and we provide a proof of concept for this novel application. These findings pave the way for the development of novel molecular tools for RNA-directed DNA surgery.

SUMMARY OF THE INVENTION

A method for the site-specific modification of a target DNA molecule through contacting under suitable conditions, a target polydeoxynucleotide molecule; and an RNA-guided DNA endonuclease comprising at least one RNA sequence and at least one of an RuvC active site motif and an HNH active site motif; to result in the target polydeoxynucleotide molecule modified in a region that is determined by the complimentary binding of the RNA sequence to the target DNA molecule is provided. The method includes incubating under suitable conditions a composition that includes a target double stranded polydeoxynucleotide or single stranded polydeoxynucleotide; wherein a double stranded polydeoxynucleotide contains a short proto-spacer adjacent motif (PAM), which is non-obligatory for a single stranded polydeoxynucleotide; and where PAM comprises a 5'-NGGNG-3' sequence; a polyribonucleotide (crRNA) comprising a 3' and 5' regions wherein the 3' region comprises at least 22 nt of the repeat present in a microbe containing CRISPR locus and 5'-region comprises of at least 20 nt of the spacer sequence immediately downstream of the repeat in the CRISPR locus, which is substantially complementary, optionally complementary, to a portion of the target polynucleotide, a polypeptide wherein the amino acid sequence of polypeptide and amino acid sequence of SEQ ID NO: 1 have at least 80% identity, isolated from *S. thermophilus*, or genetically modified microorganism, including a genetically modified *E. coli*, or wherein the polypeptide is produced by a method selected from recombinant DNA technology or chemical synthesis; a polyribonucleotide tracrRNA of nucleotide sequence SEQ ID NO: 5 (or have at least 80% identity) comprising a 5' and 3' regions wherein the 5' region is comprised of at least 22 nucleotides is complementary to the 22 nucleotides 3' region of crRNA, and 3' region. Wherein polyribonucleotides are produced by in vitro transcription or chemical synthesis. Wherein, suitable conditions means conditions in vitro or in vivo where reaction might occur.

A method for the conversion of Cas9 polypeptide into a nickase, cleaving only one strand of double-stranded DNA, by inactivating one of the active sites (RuvC or HNH) in the polypeptide by at least on point mutation, exemplified by D31A (SEQ ID NO: 2), N891A (SEQ ID NO: 3) and H868A (SEQ ID NO: 4) point mutations, is provided. RuvC motif mutant cleaves only bottom DNA strand in respect to 5'NGGNG-3' motif, while HNH motif mutant cleaves top strand.

Polypeptide-polyribonucleotides complex might be isolated from a genetically modified microbe (for example *Escherichia coli* or *Streptococcus thermophilus*), or assembled in vitro from separate components. In the genetically modified microbe components of the complex might be encoded on the one, two or three separate plasmids containing host promoters of the genetically modified microbe or promoters from a native host genome.

A method for assembly of active polypeptide-polyribonucleotides complex in vitro, comprising incubating the components of the complex under conditions suitable for complex assembly is provided. The complex might be assembled using three or four components. Method for three components assembly comprises incubating the Cas9 polypeptide, 78 nt tracrRNA polyribonucleotide (SEQ ID NO: 5), and 42 nt crRNA polyribonucleotide (5'-NNNNNNNNNNNNNNNNNNNNNGUUUUAGAGCU-GUGUUGUUUCG-3') (SEQ ID NO: 15) under conditions suitable for complex assembly. Method for four components assembly comprises incubating the Cas9 polypeptide; 102 nt tracrRNA polyribonucleotide (SEQ ID NO: 6); polyribonucleotide containing sequence 5'-NNNNNNNNNNNNNNNNNNNNNGUUUUAGAGCU-GUGUUGUUUCG-3' (SEQ ID NO: 15) and flanking regions and RNase III polypeptide, cleaving double stranded RNA polynucleotide. The examples for polyribonucleotide containing sequence 5'-NNNNNNNNNNNNNNNNNNNNNGUUUUAGAGCU-GUGUUGUUUCG-3' (SEQ ID NO: 15) are SEQ ID NO: 8, SEQ ID NO: 9, SEQ ID NO: 10, SEQ ID NO: 11 and SEQ ID NO: 12). Examples of source for suitable RNaseIII include *Escherichia coli* or *Streptococcus thermophilus*.

A method for re-programming of a Cas9-crRNA complex specificity by mixing separate components or using a cassette containing a single repeat-spacer-repeat unit is provided. Any sequence might be inserted between two repeats in the cassette using suitable restriction endonucleases. Cassette might be used to target sequences in vivo, or to produce RNA ribonucleotide suitable for complex assembly in vitro.

BRIEF DESCRIPTION OF THE FIGURES

FIG. 14 discloses SEQ ID NOS. 31 and 7, respectively, in order of appearance.

Figure 17:
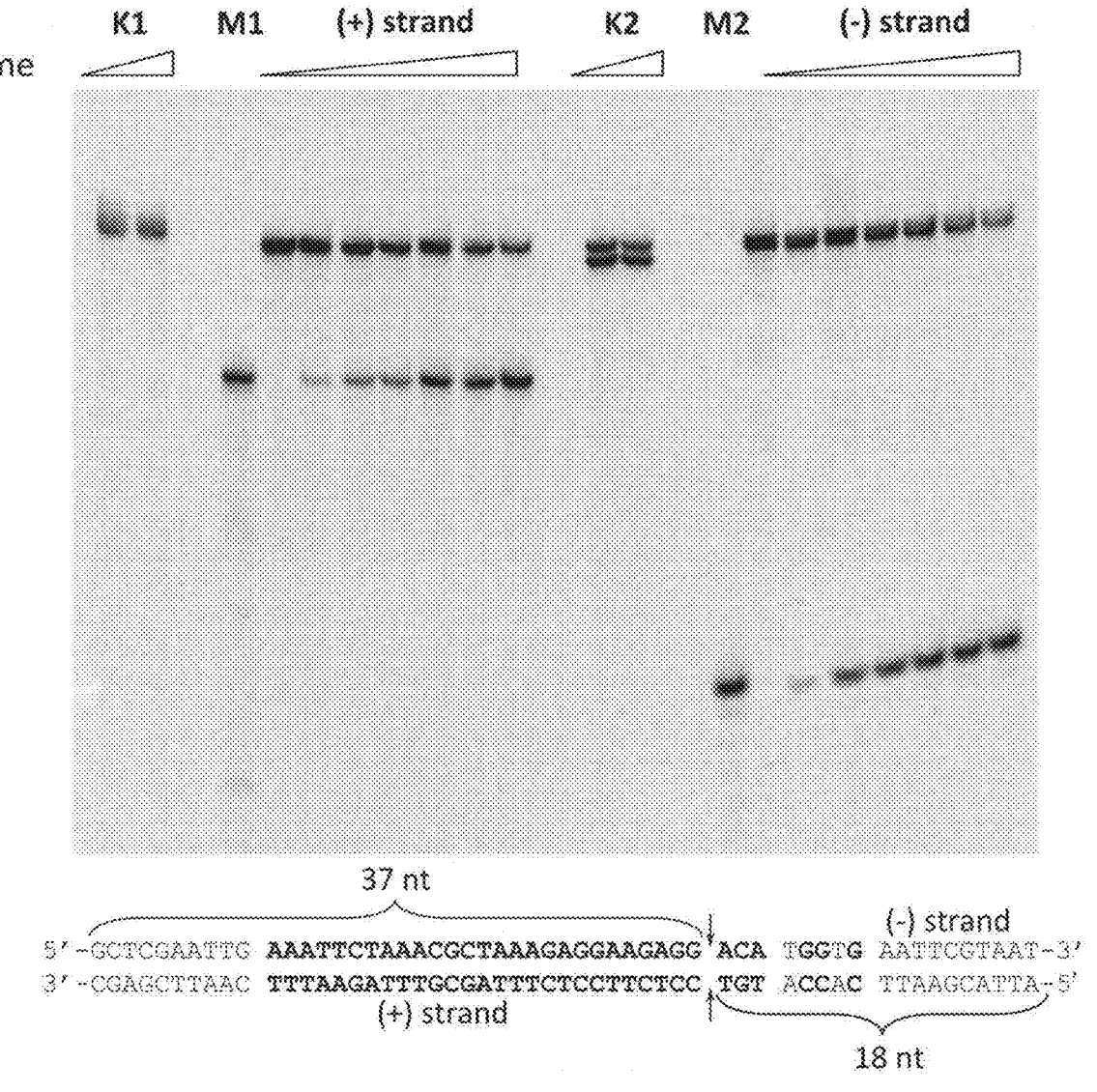

FIG. 17 shows DNA oligoduplex cleavage by Cas9-crRNA complex. The strand of oligoduplex which is complementary to crRNA is marked as (+) strand, while the other strand – (−) strand. To monitor cleavage reactions either (+) or (—) strand of the oligoduplex was P33-labeled at the 5'-terminus. M1 and M2 are synthetic oligonucleotide markers corresponding to the 37 nt of (−) strand and 18 nt of (+) strand which were used to determine the size of the cleavage products and map the cleavage position. Cas9 protein cleaves both strands of oligoduplex inside the proto-spacer, after the 37th nucleotide, 3 nt upstream of the PAM (5'-NGGNG-3') leaving blunt ends. Both strands of non-specific substrate (K1 and K2) are not cleaved when incubated with Cas9-crRNA complex for 30 min. FIG. 17 discloses SEQ ID NO: 31.

Figures 18, 19:
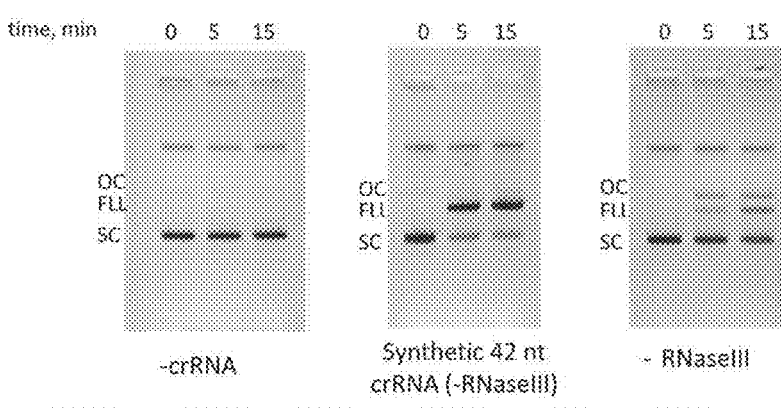

FIG. 18 shows plasmid DNA cleavage by Cas9-crRNA complex assembled in the absence of RNaseIII. Cas9-crRNA complex was incubated with pSP1 plasmid and reaction products analysed in the agarose gels. The pSP1 plasmid is resistant for cleavage in the presence of complex assembled without crRNA (left panel). The pSP1 plasmid is converted into linear form in the presence of complex assembled using synthetic 42 nt crRNA (no RNAseIII) (middle panel). The pSP1 plasmid is converted into a mixture of linear and circular DNA forms in the presence of complex assembled using CRISPR RNA transcript (no RNAseIII) (right panel).

FIG. 19 shows DNA oligoduplex cleavage by Cas9-crRNA complex. The strand of oligoduplex which is complementary to crRNA is marked as (+) strand, while the other strand – (−) strand. To monitor cleavage reaction either (+) or (—) strand of the oligoduplex was P33-labeled at the 5'-terminus. M1 and M2 are synthetic oligonucleotide markers corresponding to the 37 nt of (−) strand and 18 nt of (+) strand which were used to determine the size of the cleavage products and map the cleavage position. Cas9 protein cleaves both strands of oligoduplex inside the proto-spacer, after the 37th nucleotide form the 5'-end, 3 nt upstream of the PAM (5'-NGGNG-3') leaving blunt ends. Both strands of non-specific substrate (K1 and K2) are not cleaved when incubated with Cas9-crRNA complex for 30 min. FIG. 19 discloses SEQ ID NO: 31.

Figure 20:
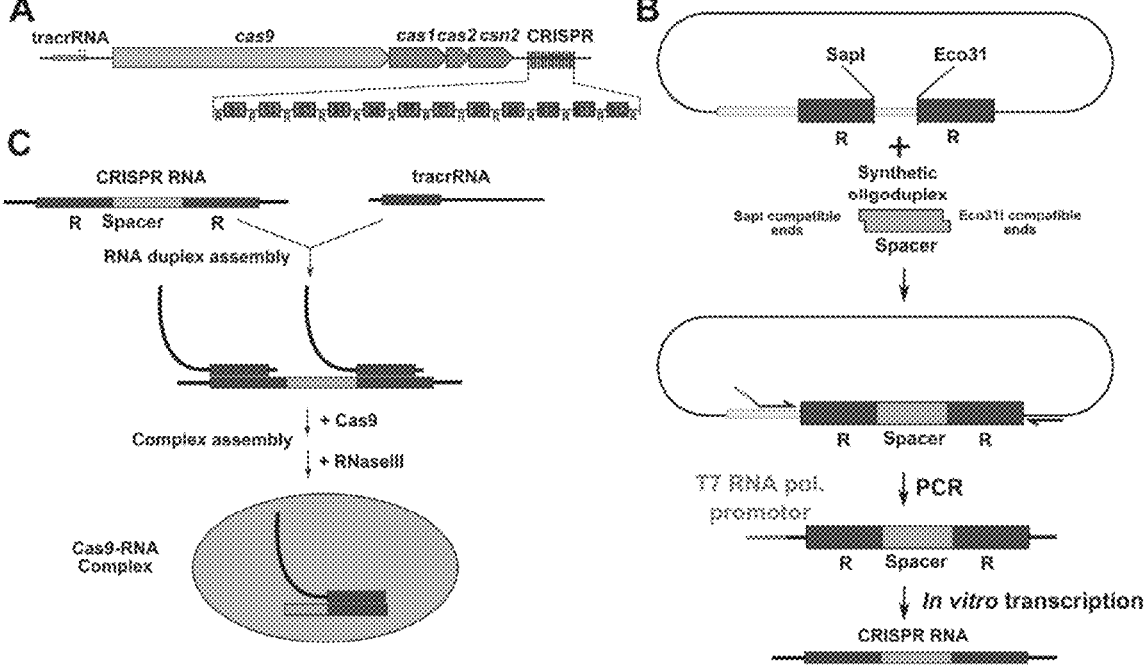

FIG. 20 shows (A) Schematic representation of the CRISPR3/Cas system of *S. thermophilus* DGCC7710. Four cas genes (cas9, cas1, cas2, csn2) are located upstream of the CRISPR repeat-spacer array, consisting of 13 repeat (R) sequences and 12 unique spacers (S1-S12). The tracrRNA, required for crRNA maturation in Type II CRISPR/Cas systems (Deltcheva et al., 2011. Nature 471, 602-7), is located upstream the cas9 gene and encoded on the opposite DNA strand (shown by an arrow) with respect to the other elements of this system. (B) The pathways for a new spacer insertion in to CRISPR region and CRISPR RNA synthesis. Synthetic oligoduplex encoding desired spacer sequence and containing SapI and Eco31I restriction compatible ends was inserted between two repeats. The CRISPR region was amplified using PCR. The new spacer encoding CRISPR RNA was obtained by In vitro transcription. (C) In vitro assembly of Cas9-RNA complex. The CRISPR RNA and tracrRNA transcripts were assembled in to duplex. The Cas9 protein was first pre-incubated with RNA duplex, followed by the subsequent incubation with RNAseIII to generate a catalytically competent Cas9-RNA complex.

Figure 21:
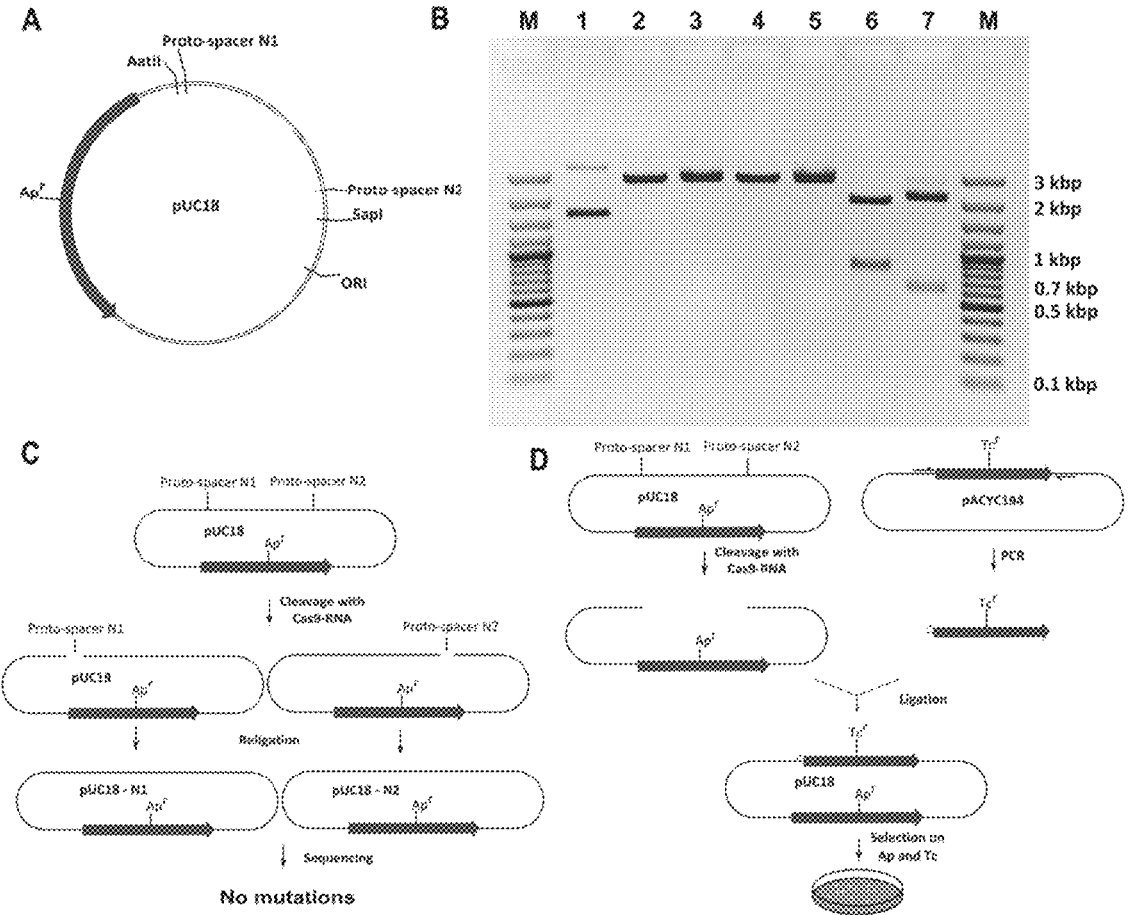

FIG. 21 shows A. Schematic representation of pUC18 plasmid. The distance between SapI and AatII restriction sites is 775 bp, while the distance between two spacers is 612 bp. B. pUC18 plasmid cleavage by re-programed Cas9-crRNA complexes. "1"—pUC18 plasmid; "2"—pUC18 cleaved with AatII; "3"—pUC18 cleaved with complex containing crRNA matching proto-spacer1; "4"—pUC18 cleaved with SapI; "5"—pUC18 cleaved with complex containing crRNA matching proto-spacer2; "6"—pUC18 cleaved with AatII and SapI; "7"—pUC18 cleaved with mix of the complexes used in the line 3 and 5.

Figure 22:
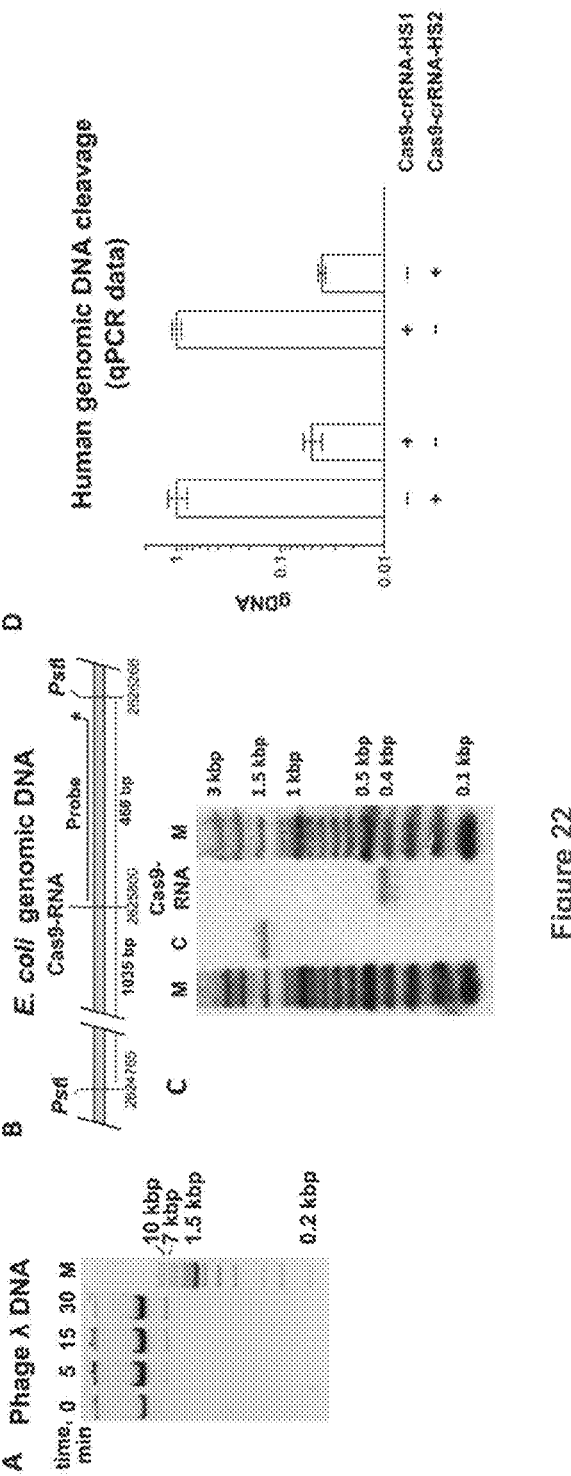

FIG. 22 shows genomic DNA cleavage with in vitro assembled Cas9-RNA complex. (A) Agarose gel analysis of linear A DNA cleavage products. Phage A DNA was incubated with Cas9-RNA complex in the reaction buffer for various time intervals. The target site for Cas9-RNA complex is located 8 kb away from the cos site. (B). Probe selection for Southern blot experiments. Genomic DNA was fragmented by treating with PstI enzyme. The proto-spacer is located between two PstI sites. If genomic DNA is cleaved with Cas9-RNA complex, 466 bp fragment should be detected. Otherwise the probe will hybridize with 1499 bp length fragment. (C) Southern blot analysis of genomic DNA fragments. C line—*E. coli* genomic DNA fragmented with PstI. Cas9-RNA—genomic DNA was incubated with Cas9-RNA complex before fragmentation. (D). Human genomic DNA cleavage by Cas9-crRNA complex. Relative amount of intact DNA DNA fragments were estimated by qPCR.

The following non-limiting examples further describe the methods, compositions, uses, and embodiments.

DETAILED DESCRIPTION OF ILLUSTRATIVE EMBODIMENTS

Example 1

In this example, we have isolated the Cas9-crRNA complex of *S. thermophilus* CRISPR3/Cas system and demonstrate that it cuts in a PAM dependent manner both synthetic oligodeoxynucleotide and plasmid DNA bearing a nucleotide sequence complementary to the crRNA. Furthermore, we provide experimental evidence that PAM is recognized in the context of double-stranded DNA and is critical for in vitro DNA binding and cleavage. Finally, we show that RuvC and HNH-motifs of Cas9 contribute to the cleavage of opposite DNA strands. Taken together, our data demonstrate that Cas9-crRNA complex functions as RNA-guided endonuclease which uses RNA module for the target site recognition and employs two separate active sites in the protein module for DNA cleavage. These findings pave the way for engineering of programmable Cas9-crRNA complexes as universal RNA-guided endonucleases.

Materials and Methods

DNA manipulations. Genomic DNA of *Streptococcus thermophilus* DGCC7710 strain was used as a template in PCR reactions to clone cas9. To generate a pASKIBA3-Cas9 plasmid which was used for the expression of the C-terminal Strep-tagged Cas9 protein variant, PCR fragment amplified with following primers: 5'-ACGTCTCAAATGTTGTT-TAATAAGTGTATAATAATTTC-3' (SEQ ID NO: 21) and 5'-ACGTCTCCGCGCTACCCTCTCCTAGTTTG-3' (SEQ ID NO: 22) was cloned into the pASK-IBA3 expression vector via Esp3I sites. To generate a pBAD-Cas9 plasmid which was used for the expression of the C-terminal 6×His-tagged Cas9 protein variant ("6×His" disclosed as SEQ ID NO: 23), PCR fragment amplified with the following primer pair: 5'-ACGTCTCACATGACTAAGCCATACTCAAT-TGGAC-3' (SEQ ID NO: 24) and 5'-ACTCGA-GACCCTCTCCTAGTTTGGCAA-3' (SEQ ID NO: 25) was cloned into the pBAD24-Chis expression vector via NcoI and XhoI sites. Full sequencing of cas9 gene in pASKIBA3-Cas9 and pBAD-Cas9 plasmids revealed no difference with the original cas9 sequence. To obtain plasmids pCas9(−)SP1 (part (B) of FIG. 1) and pCRISPR3-SP1 (part (A) of FIG. 2), bearing a single spacer1, PCR fragment amplified from pCRISPR3 plasmid with the following primer pair:5' GAC-CACTTATTGAGGTAAATGAG 3' (SEQ ID NO: 26)/5' CAAACCAGGATCCAAGCTAATACAGCAG-3' (SEQ ID NO: 27) ((BamHI (GGATCC) sites is underlined) was cloned into pCas9(−) and pCRISPR3 plasmids (Sapranaus-kas et al., 2011. Nucleic Acids Res 39:9275-82), respectively.

Expression and purification of Cas9 protein and Cas9-crRNA complex. 6×His-tagged ("6×His" disclosed as SEQ ID NO: 23) version of Cas9 protein was expressed and purified using a scheme described for the Cas3 protein from *S. thermophilus* CRISPR4/Cas system (Sinkunas et al., 2011. EMBO J 30:1335-42). For purification of the Cas9-crRNA complex, Strep-tagged version of the Cas9 protein was expressed in *E. coli* RR1 strain, bearing pCas9(−)SP1 plasmid (part (B) of FIG. 1). LB broth was supplemented with Ap (100 μg/ml) and Cm (10 μg/ml). *E. coli* cells for the Cas9-crRNA complex isolation were grown in two steps. First, 4 ml of cells culture were grown at 37° C. to OD600 of ~0.5, and expression induced by adding 0.2 μg/ml of anhydrotetracycline (AHT) (Sigma). After for 4 h, 1/400 of the pre-induced culture was inoculated into fresh LB medium supplemented with Ap (100 μg/ml), Cm (12 μg/ml) and AHT (0.2 μg/ml) and was grown at 37° C. overnight. Harvested cells were disrupted by sonication and cell debris removed by centrifugation. The supernatant was loaded onto the 1 ml StrepTrap HP column (GE Healthcare) and eluted with 2.5 mM of desthiobiotin. Approximately 1.5 μg of the Cas9 protein was obtained in a single run from 1 L of *E. coli* culture. The fractions containing Cas9 were stored at +4° C. for several days. The homogeneity of protein preparations was estimated by SDS-PAGE. Protein concentrations in the Cas9-crRNA complexes were determined by densitometric analysis of SDS-PAGE gels containing samples of Strep-Tactin purified Cas9 proteins along with known amounts of His-tagged Cas9 protein. The concentration of the Cas9-crRNA complexes is expressed as Cas9 protein concentration assuming that Cas9 is a monomer and binds crRNA in a complex with 1:1 stoichiometry.

Northern blot analysis. Cas9-bound RNA was isolated from Strep-Tactin purified Cas9, co-expressed with pCas9 (−)SP1 plasmid using the miRNeasy Mini kit (Qiagen). Northern blots were performed by running RNA on a 10% polyacrylamide gel with 7 M urea in 20 mM MOPS/NaOH pH 8 buffer. The RNA was transferred to a SensiBlot™ Plus Nylon Membrane (Fermentas) by semi-dry blotting using a Trans-blot SD (Bio-Rad). RNA was cross-linked to the membrane with 0.16 M I-ethyl-3-(3-dimethylaminopropyl) carbodiimide (EDC) (Pierce)/0.13 M 1-methylimidazole (Sigma) pH 8 at 60° C. for 1 h. The membrane was pre-hybridized with 2×SSC buffer containing 1% SDS and 0.1 mg/ml denatured DNA from fish testes (Ambion) for 1 h at 40° C. Blots were probed for 12 h with a $^{32}$P-5'-labelled 42 nt anti-crRNA DNA oligonucleotide containing 20 nt of spacer1 and 22 nt of the repeat sequence (5'-TCGAAACAACACAGCTCTAAAACTGTCCTCTTCCT-CTTTAGC-3' (SEQ ID NO: 28)). The blots were washed 3× for 15 min with 0.2×SSC buffer containing 0.2% SDS, and were visualized using phosphorimaging. A 42 nt synthetic oligoribonucleotide (5'-CGCUAAAGAG-GAAGAGGACAGUUUUAGAGCUGUGUUGUUUCG-3' (SEQ ID NO: 7)) and 84 nt DNA oligonucleotide.

Oligonucleotide substrates. All oligonucleotide substrates used in this study are given in Table 1. Oligodeoxyribo-nucleotides were purchased from Metabion (Martinsried, Germany). The 5'-ends of oligonucleotides were radiola-belled using PNK (Fermentas) and [γ-33P]ATP (Hartmann Analytic). Duplexes were made by annealing two oligo-nucleotides with complementary sequences (SP1, SP1-Δp, SP2). Radioactive label was introduced at the 5' end of individual DNA strand prior to the annealing with unlabelled strand.

Reactions with oligonucleotide substrates. Reactions were typically carried out by adding 2 nM of Cas9-crRNA complex to 1 nM labeled oligonucleotide in 10 mM Tris-HCl (pH 7.5 at 37° C.), 10 mM NaCl, 0.1 mg/ml BSA and 10 mM MgCl2 at 37° C. Aliquots were removed at timed intervals and quenched with loading dye (95% v/v forma-mide, 0.01% bromphenol blue, 25 mM EDTA, pH 9.0) and subjected to denaturing gel electrophoresis through 20% polyacrylamide followed by a FLA-5100 phosphorimager (Fujilm) detection.

Reactions with plasmid substrates. Reactions on pUC18 plasmid and its derivatives (Sapranauskas et al., 2011. Nucleic Acids Res 39:9275-82) were conducted at 37° C. in the buffer used for reactions on oligonucleotide substrates. Reaction mixtures typically contained 2.5 nM supercoiled plasmid and 2 nM of Cas9-crRNA complex. The reactions were initiated by adding protein to the mixture of the other components. Aliquots were removed at timed intervals and quenched with phenol/chloroform. The aqueous phase was mixed with loading dye solution (0.01% bromphenol blue and 75 mM EDTA in 50% v/v glycerol) and analyzed by electrophoresis through agarose.

Plasmid cleavage position determination. To achieve complete cleavage of plasmid substrate, 8 nM of Cas9-crRNA complex was incubated with 2.5 nM of supercoiled plasmid in the reaction buffer at 37° C. for 10 min. Reaction products were purified and concentrated using GeneJET PCR Purification Kit (Fermentas). Spacer1 surrounding region of Cas9 linearized and nicked plasmids were directly sequenced with the following primers: 5'-ccgcatcaggcgccat-tcgcc-3' (SEQ ID NO: 29) (sequencing of (+)strand) and 5'-gcgaggaagcggaagagcgccc-3' (SEQ ID NO: 30) (sequenc-ing of (−) strand).

Binding assay. Increasing amounts of protein-crRNA complex were mixed with 0.5 nM of 33P-labeled double-stranded and single-stranded DNA substrates (Table 1) in the binding buffer (40 mM Tris-acetate, pH 8.3 at 25 C, 0.1 EDTA, 0.1 mg/ml BSA, 10% v/v glycerol) and incubated for 15 min at room temperature. Free DNA and protein-DNA complexes were separated on the non-denaturing 8% poly-acrylamide gel (ratio of acrylamide/N,N'-methylenebisacry-lamide 29:1) using 40 mM Tris-acetate (pH 8.3) supple-mented with 0.1 mM EDTA as the running buffer. Electrophoresis was run at room temperature for 3 h at 6 V/cm.

Mutagenesis. The mutants D31A and N891A were obtained by the site-directed mutagenesis as previously described (Tamulaitis et al., 2007. Nucleic Acids Res 35:4792-9). Sequencing of the entire gene for each mutant confirmed that only the designed mutation had been intro-duced.

TABLE 1

```
Oligonucleotide substrates.
Proto-spacer sequence is underlined,
PAM is on bold.
```

| Oligo-nucle-otide | Sequence | Specifi-cation |
|---|---|---|
| SP1 (SEQ ID NO: 31) | 5'-GCTCGAATTGAAATTCTAAA CGCTAAAGAGGAAGAGGACATGG TGAATTCGTAAT-3' 3'-CGAGCTTAACTTTAAGATTTG CGATTTCTCCTTCTCCTGTACCAC TTAAGCATTA-5' | 55 bp oligoduplex substrate containing proto-spacer1 and PAM |
| SP1-pΔ (SEQ ID NO: 32) | 5'-GCTCGAATTGAAATTCTAAAC GCTAAAGAGGAAGAGGACAAATTC GTAAT-3' 3'-CGAGCTTAACTTTAAGATTTG CGATTTCTCCTTCTCCTGTTTAAG CATTA-5' | 50 bp oligoduplex substrate containing proto-spacer2 |
| SP2 (SEQ ID NO: 33) | 5'-GCTCGAATTGTACTGCTGTAT TAGCTTGGTTGTTGGTTTGTGGTG AATTCGTAAT-3' 3'-CGAGCTTAACATGACGACATA ATCGAACCAACAACCAAACACCAC TTAAGCATTA-5' | 55 bp oligoduplex substrate containing proto-spacer2 and PAM (oligodublex without proto-spacer1) |
| S(+) SP1 (SEQ ID NO: 34) | 5'-ATTACGAATTCACCATGTCCT CTTCCTCTTTAGCGTTTAGAATTT CAATTCGAGC-3' | 55 nt ssDNA oligonucleotide substrate (+) strand of SP1 oligoduplex |
| S(+) SP1-pΔ (SEQ ID NO: 35) | 5'-ATTACGAATTTGTCCTCTTCC TCTTTAGCGTTTAGAATTTCAATT CGAGC-3' | 50 nt ssDNA oligonucleotide substrate(+) strand of SP1-pA oligoduplex |
| S(+) SP2 (SEQ ID NO: 36) | 5'-ATTACGAATTCACCACAAACC AACAACCAAGCTAATACAGCAGTA CAATTCGAGC-3' | 55 nt ssDNA oligonucleotide substrate, (+) strand of SP2 oligoduplex |
| s(-) SP1 (SEQ ID NO: 37) | 5'-GCTCGAATTGAAATTCTAAAC GCTAAAGAGGAAGAGGACATGGTG AATTCGTAAT-3' | 55 nt ssDNA oligonucleotide substrate, (-) strand of SP1 oligoduplx |
| SP1-20 (SEQ ID NO: 38) | 5'-GCTCGAATTGCGCTAAAGAGG AAGAGGACATGGTGAATTCGTAA T-3' 3'-CGAGCTTAACGCGATTTCTCC TTCTCCTGTACCACTTAAGCATT A-5' | 45 nt oligoduplex substrate containing 20 nt of proto-spacer1 and PAM |
| SPN (SEQ ID NO: 39) | 5'-GCTCGAATTGCCACCCAGCAA AATTCGGTTTTCTGGCTGATGGTG AATTCGTAAT-3' 3'-CGAGCTTAACGGTGGGTCGTT TTAAGCCAAAAGACCGACTACCAC TTAAGCATTA-5' | 55 bp oligoduplex substrate containing proto-spacerN and PAM |

Results

Expression and purification of the Cas9-crRNA complex. The cas9 gene from the CRISR3 system of *S. thermophilus*

Figure 1:
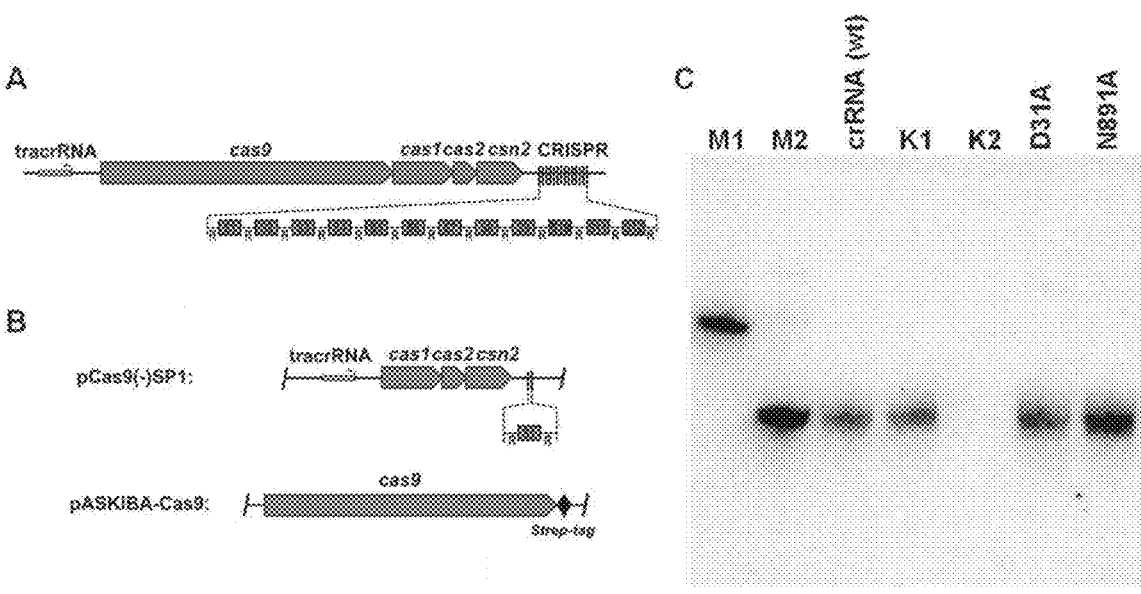
FIG. 1 shows Cas9 protein co-purifies with crRNA. (A) Schematic representation of CRISPR3/Cas system of *S. thermophilus*. Four cas genes (cas9, cas1, cas2, csn2) are located upstream of the CRISPR repeat-spacer array, consisting of 13 repeat (R) sequences and 12 unique spacers (S1-S12). The tracrRNA, required for crRNA maturation in Type II CRISPR systems (Deltcheva et al., 2011. Nature 471:602-7), is located upstream the cas9 gene and encoded on the opposite DNA strand (showed by an arrow) in respect to the other elements of CRISPR3/Cas system. (B) Schematic representation of heterologous loci in two plasmids used for the co-expression of the Cas9-crRNA complex. *E. coli* RR1 strain contained pCas9(–)1SP (encoding Cas1, Cas2, Csn2, SP1 and tracrRNA) and pASKIBA-Cas9 (encoding Strep-tagged version of Cas9) plasmids. (C) Northern analysis of Cas9-crRNA complexes using anti-crDNA oligonucleotide as a probe. M1—84 nt oligodeoxynucleotide corresponding to the spacer S1-repeat unit; M2—42 nt synthetic oligoribonucleotide corresponding to the predicted *S. thermophilus* CRISPR3 crRNA (See FIG. 4); crRNA (wt)—crRNA isolated from the wt Cas9 complex; K1—crRNA (wt) treated with Dnase I for 15 min; K2—crRNA (wt) treated with RNaseI for 15 min, D31A—crRNA purified from the Cas9 D31A mutant complex; N891A—crRNA purified from the Cas9 N891A mutant complex.
Figure 2:
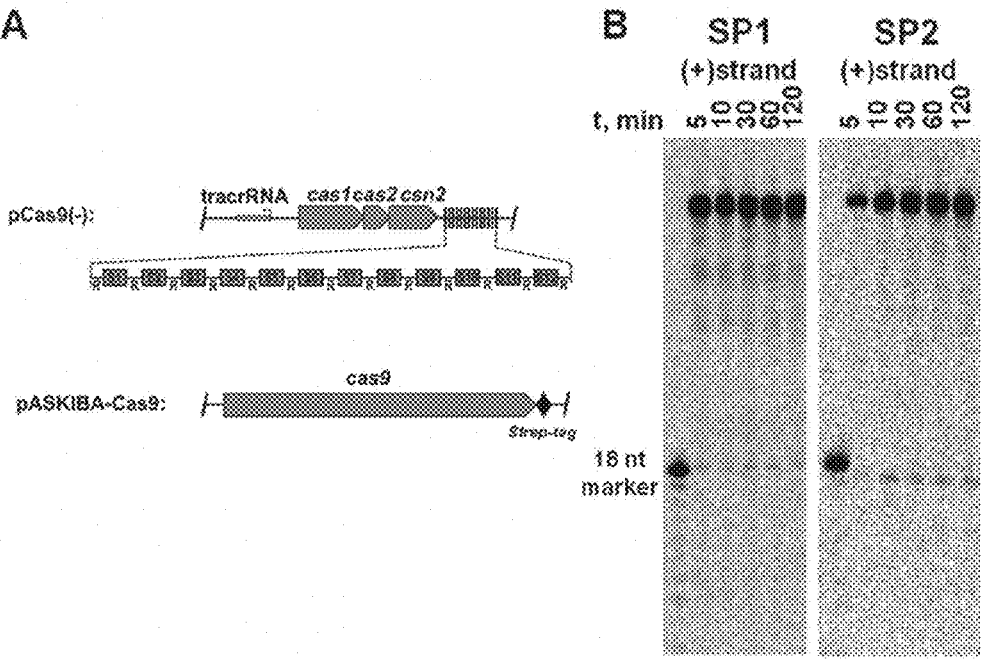
FIG. 2 shows DNA cleavage by Cas9-crRNA complexes obtained by Cas9 co-expression with full length CRISPR locus. (A) Schematic representation of CRISPR/Cas locus of recombinant pCas9(–) plasmid carrying indigenous 12 spacer-repeat array of SthCRISPR3/Cas system and xpASKIBA-Cas9 plasmid carrying cas9 gene with a Strep-tag at the C-terminus. (B) Oligoduplex cleavage assay. Both pCas9(–) and pASKIBA-Cas9 plasmids were co-expressed in *E. coli*, Cas9-crRNA complexes were purified and subjected to cleavage analysis using SP1 (first proto-spacer) and SP2 (second proto-spacer) oligoduplexes labeled with 33P at the 5'-end of the (+) strand. Reaction products were analysed on PAA gel.

DGCC7710 strain was cloned into the pASK-IBA3 vector to produce a construct encoding a Cas9 protein fusion containing a C-terminal Strep(II)-tag (part (B) of FIG. 1). Initially, we have tried to purify Cas9-crRNA complex from *E. coli* strain RR1 expressing Cas9 protein on the pASK-IBA3 vector and other Cas proteins (except Cas9) on pCas9(−) plasmid (Sapranauskas et al, 2011). pCas9(−) also contained a complete CRISPR3 array comprised of 12 spacer-repeat units (part (A) of FIG. 2). To achieve simultaneous transcription of all target genes we performed cas9 gene expression in two steps. First, we induced Cas9 expression in a small volume of *E. coli* culture and after 4 h transferred an aliquot of pre-induced culture into a larger volume of fresh LB media already containing inductor and incubated overnight. Cas9 protein complex was purified from the crude cell extract using Strep-Tactin®Sepharose®. We managed to isolate a small amount of the Cas9-crRNA complex which showed only traces of nucleolytic activity on the oligoduplex SP1 containing a proto-spacer1 and PAM. We assumed that low cleavage activity could be due to the intrinsic heterogeneity of Cas9-crRNA complexes resulting from the transcription of 12 spacer-repeat units. If all spacer-repeat units are uniformly transcribed into a mature crRNA, the concentration of the Cas9 complex containing crRNA against spacer-1 will make $1/12$th fraction of the total Cas9-crRNA concentration. The cleavage activity of the Cas9-crRNA preparation against the SP2 oligoduplex containing a proto-spacer-2 and PAM is consistent with the heterogeneity of Cas9-crRNA complexes (part (B) of FIG. 2). To increase the yield of the specific Cas9-crRNA complex we engineered a pCas9(−)SP1 plasmid which contains a single R-spacer1-R unit in the CRISPR array (part (B) of FIG. 1). Plasmid transformation interference assay confirmed that the CRISPR3/Cas system carrying a single spacer1 prevents plasmid pSP1 transformation in *E. coli* with the same efficiency as the CRISPR3/Cas system carrying a complete CRISPR region (part (B) of FIG. 3). We have isolated Cas9-crRNA complex following the procedure described above and analysed crRNA bound to Cas9 protein.

Figure 3:
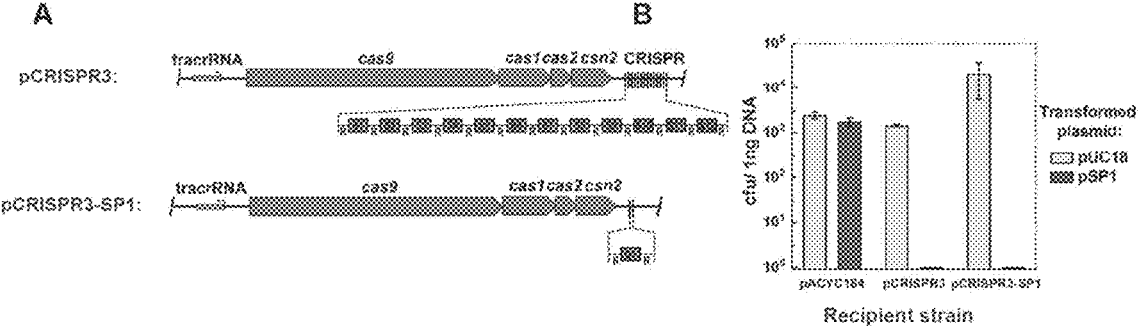
FIG. 3 shows immunity against plasmid transformation in *E. coli* cells provided by the SthCRISPR3/Cas system. (A) Schematic representation of CRISPR/Cas locus of recombinant plasmid pCRISPR3 carrying indigenous 12 spacer-repeat array of SthCRISPR3/Cas system and engineered pCRISPR3-SP1 plasmid carrying 1 spacer-repeat unit. (B) Interference of plasmid transformation by SthCRISPR3/Cas system in *E. coli* cells. *Escherichia coli* RR1 recipient strains carrying plasmids pACYC184, pCRISPR3 or pCRISPR3-SP1, were transformed with plasmid pSP1 carrying proto-spacers and PAM or pUC18 (1). Transformation efficiency is expressed as cfu per nanogram of plasmid DNA (mean±SD).
Figure 4:
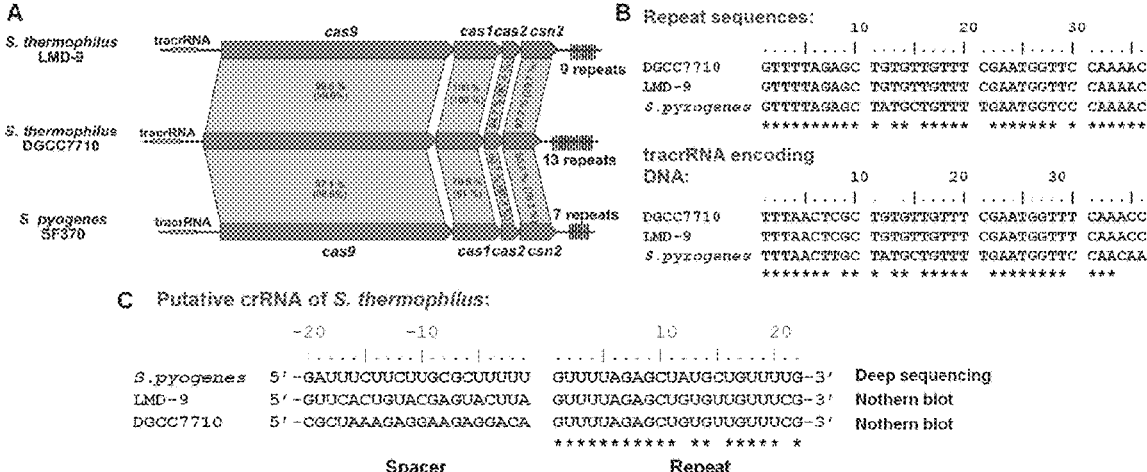
FIG. 4 shows comparison of Type IIA CRISPR/Cas systems from *S. thermophilus* DGCC7710, LMD-9 and *S. pyogenes* SF370 strains. (A) Schematic organization of the CRISPR/Cas systems. Nucleotide sequences corresponding to the tracrRNA required for the crRNA maturation in of *S. pyogenes* (2) are present in LMD-9 and DGCC7710. Percentage of identical and similar (in parenthesis) residues between corresponding protein sequences that are connected by dashed lines. (B). Alignment of the conserved repeat sequences and tracrRNA. Corresponding sequences from DGCC7710 and LMD-9 are identical. Nucleotide positions which are identical in all three strains are labeled with an asterisk below aligned sequences. Part (B) of FIG. 4 discloses SEQ ID NOS 50, 50-51, 52, and 52-53, respectively, in order of appearance. (C) Comparison of crRNA sequences. The sequence and length of *S. pyogenes* crRNA was determined by deep sequencing analysis (2). The approximate length of crRNA from *S. thermophilus* LMD-9 (2) and DGCC7710 (this work) strains were determined by the northern blot analysis. Part (C) of FIG. 4 discloses SEQ ID NOS 54-56, respectively, in order of appearance.

Cas9 protein co-purifies with crRNA. CRISPR3/Cas system of *S. thermophilus* belongs to the Type IIA subtype (former Nmeni or CASS4) of CRISPR/Cas systems (Makarova et al., 2011. Nat Rev Microbiol 9:467-77). It has been shown that in the Type IIA CRISPR/Cas system of *Streptococcus pyogenes* trans-encoded small RNA (tracrRNA) and bacterial RNaseIII are involved in the generation of crRNA (Deltcheva et al., 2011. Nature 471:602-7). *Streptococcus pyogenes* crRNA is only 42 nt in length and has no "5'-handle" which is conserved in crRNA's from Type I and III CRISPR systems (Hale et al., 2009. Cell 139:945-56; Jore et al., 2011. Nat Struct Mol Biol 18:529-36). According to the northern blot analysis crRNA of similar length is generated in the *S. thermophilus* LMD-9 CRISPR3/Cas system (Makarova et al., 2011. Nat Rev Microbiol 9:467-77), which is almost identical to the CRISPR3/Cas system of DGCC7710 strain (parts (A) and (B) of FIG. 4). We assumed that crRNA isolated from the Cas9-crRNA complex expressed in the heterologous *E. coli* strain (FIG. 1) may have the same length (FIG. 4). Therefore, to probe nucleic acids extracted from the Strep-Tactin purified Cas9 complex we used 42 nt anti-crRNA DNA oligonucleotide comprised of 22 nt region corresponding to the 3'-end of the repeat sequence and 20 nt at the 5'-end of SP1 fragment. Nucleic acid present in the Cas9 complex hybridized with anti-crRNA oligonucleotide, and was sensitive to RNAse but not DNAse treatment (part (C) of FIG. 1). The size of extracted crRNA was identical to the 42 nt synthetic oligoribonucleotide corresponding to the putative crRNA of the CRISPR3 system of *S. thermophilus* DGCC7710 strain (part (A) of FIG. 3, part (C) of FIG. 4). Taken together, these data confirm that Cas9 Strep-tag protein co-purifies with 42 nt crRNA, which is derived from CRISPR3 region.

Figure 5:
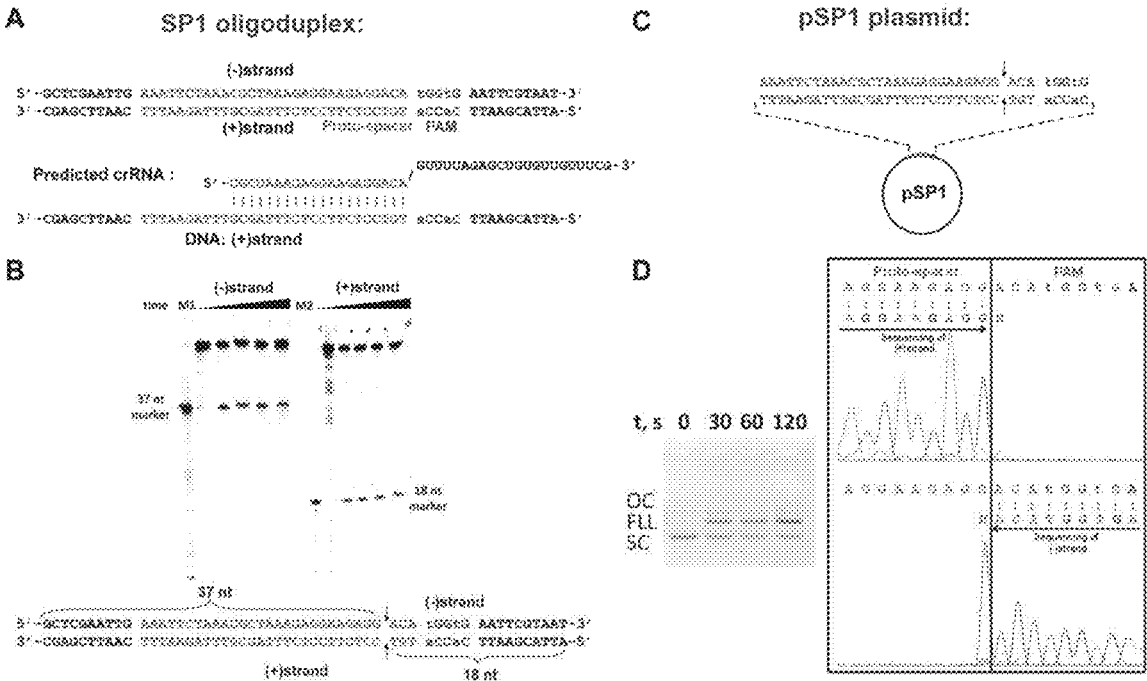
FIG. 5 shows Cas9-crRNA complex cleaves in vitro double-stranded DNA within a proto-spacer. (A) Oligoduplex substrate used in the cleavage assay. 55 nt oligoduplex SP1 contains the proto-spacer1 (red letters), PAM (blue letters) and 10 nt flanking sequences on both sides identical to those in pSP1 plasmid. In the SP1 oligoduplex DNA strand complimentary to the 5'-terminal fragment of crRNA (red letters) is named (+)strand, an opposite DNA strand is named (−)strand. Part (A) of FIG. 5 discloses SEQ ID NOS 31, 7, and 34, respectively, in order of appearance. (B) Oligoduplex SP1 cleavage. 2.5 nM of Cas9-crRNA complex and 1 nM SP1 oligoduplex labeled with 33P at the 5'-end of either (+) or (—)strand were incubated in the reaction buffer (10 mM Tris-HCl pH=7.5, 10 mM NaCl, 10 mM MgCl2, 0.1 mg/ml BSA) at 37° C. for varied time intervals (30 s to 10 min) and reaction products analysed in the 20% PAA gel. Lanes M1 and M2 contain chemically synthesized 5'-end 33P-labeled 37 nt and 18 nt oligodeoxynucleotides corresponding to the cleavage products of (−) and (+) DNA strands, respectively. Cleavage positions are designated by arrows. Part (B) of FIG. 5 discloses SEQ ID NO: 31. (C) Schematic representation of pSP1 plasmid (Sapranauskas et al., 2011. Nucleic Acids Res 39:9275-82) used in the plasmid cleavage assay. Part (C) of FIG. 5 discloses SEQ ID NO: 57. (D) pSP1 plasmid cleavage. Agarose gel analysis of pSP1 cleavage products (left panel). SC—super-coiled plasmid DNA, OC—open circular DNA nicked at one of the strands, FLL—full length linear DNA cut at both strands. Final reaction mixtures at 37° C. contained 2.5 nM of pSP1 plasmid and 2.5 nM of Cas9-crRNA complex in the reaction buffer (section B). Direct sequencing electropherograms (right panel) of (+) (upper part) and (—) (lower part) strands of pSP1 plasmid cleavage product. The non-templated addition of adenine (T in the reverse complement sequence shown here) at the extremity of sequence is a sequencing artefact caused by the polymerase. Part (D) of FIG. 5 discloses SEQ ID NOS 58, 59, 58, and 60, respectively, in order of appearance.
Figure 6:
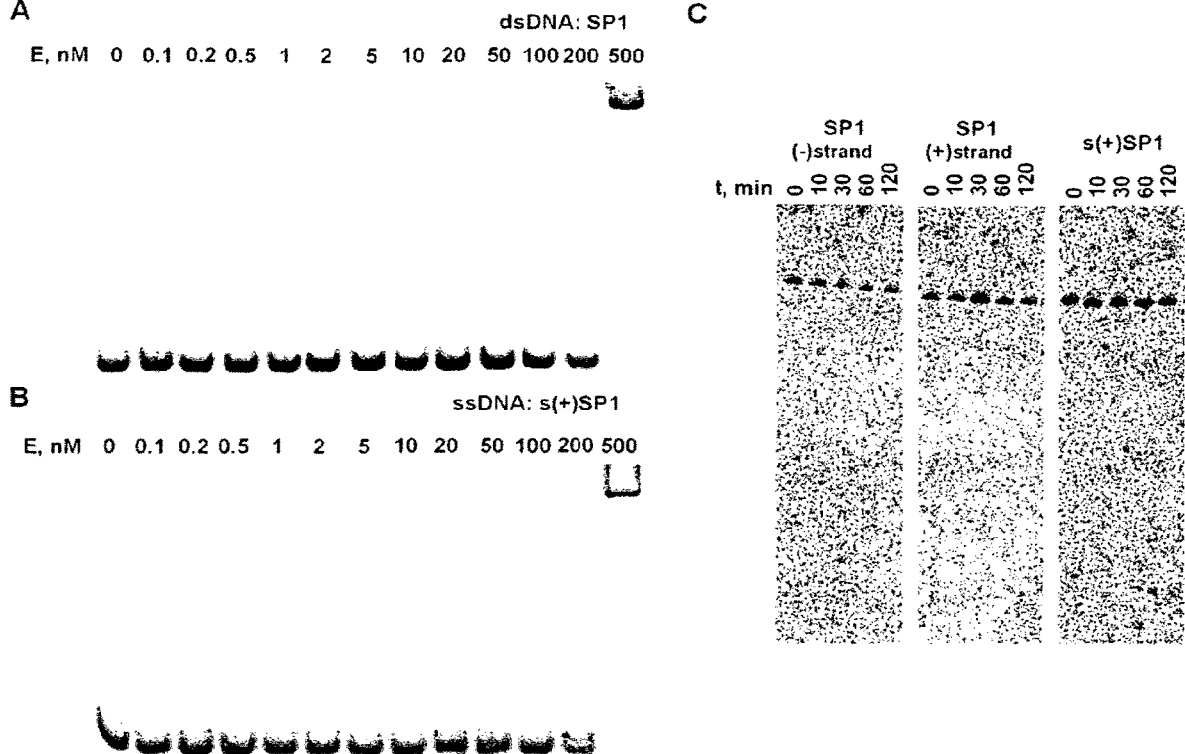
FIG. 6 shows DNA binding and cleavage analysis of Cas9-Chis protein lacking crRNA. Electrophoretic mobility shift analysis (EMSA) of Cas9-Chis protein binding to (A) the double stranded SP1 oligoduplex and (B) the single stranded s(+)SP1 oligonucleotide. Electrophoretic mobility shift experiments were performed in the binding buffer (40 mM Tris-acetate, pH 8.3 at 25 C, 0.1 EDTA, 0.1 mg/ml BSA, 10% v/v glycerol). The reactions contained 0.5 nM of the 33P-labelled oligoduplex, and the protein at concentrations as indicated above each lane. (C). Oligonucleotide cleavage assay. 5 nM of Cas9-Chis protein was incubated in the reaction buffer (10 mM Tris-HCl, pH=7.5, 10 mM NaCl, 10 mM MgCl2, 0.1 mg/ml BSA) at 37° C. with 1 nM oligonucleotide. SP1 oligoduplex was labeled with 33P at the 5'-end of the (+) or (—) strand. Single stranded oligonucleotide s(+)SP1 was labeled with 33P at the 5'-end.

Cas9 protein cleaves double-stranded DNA within a proto-spacer. To test in vitro activity of purified Cas9-crRNA complex we first used the SP1 oligoduplex (Table 1) containing the proto-spacer sequence identical to spacer SP1 in the CRISPR3 array, the PAM sequence 5'-TGGTG-3' downstream of the proto-spacer, and 10 nt flanking sequences from pSP1 plasmid (Sapranauskas et al., 2011. Nucleic Acids Res 39:9275-82) (part (A) of FIG. 5). The oligoduplex strand complementary to crRNA is named (+)strand, while the opposite duplex strand is called the ( ) strand. To monitor cleavage reaction either (+) or (—)strand of the SP1 oligoduplex was P33-labeled at the 5'-terminus. Data shown in part (B) of FIG. 5 demonstrate that the Cas9-crRNA complex cleaves both strands of oligoduplex at fixed position. Mapping of the cleavage position using synthetic oligonucleotides as size markers revealed that the Cas9-crRNA complex cuts both strands of the SP1 oligoduplex within the proto-spacer 3 nt upstream of the PAM (part (B) of FIG. 5) leaving blunt ends. It is worth to note, that no cleavage is observed after the 2 h incubation of the SP1 oligoduplex with the Cas9 protein lacking crRNA (part (C) of FIG. 6).

To test whether the Cas9-crRNA complex can locate the proto-spacer and cut DNA in vitro in long DNA substrates mimicking in vivo invading foreign DNA we analyzed cleavage of pSP1 plasmid (Sapranauskas et al., 2011. Nucleic Acids Res 39:9275-82) (part (C) of FIG. 5) carrying proto-spacer1 and PAM. In the presence of Cas9-crRNA complex supercoiled form of pSP1 plasmid was converted into a linear form (part (D) of FIG. 5), while pUC18 plasmid lacking proto-spacer1 was not cleaved. This means that both strands of the pSC1 plasmid were cleaved specifically within the proto-spacer region. We used direct sequencing to determine the ends of linear DNA form formed after the Cas9-crRNA cleavage. Sequencing results confirmed that cleavage of plasmid DNA occurred 3 nt away from 5'-NGGNG-3' PAM sequence similarly to the SP1 oligoduplex cleavage (part (D) of FIG. 5). The cleavage positions identified in the in vitro experiments (FIG. 4) for the CRISPR3/Cas system of *S. thermophilus* are identical to those determined in the in vivo cleavage experiments for the CRISPR1/Cas system in *S. thermophilus* (Garneau et al., 2010. Nature 468:67-71). To check if Cas9-crRNA induced cleavage occurs at the same position in other proto-spacer sequences, we analysed cleavage of the SP2 oligoduplex carrying a protospacer-2 and PAM sequences by the heterogeneous Cas9-crRNA complex isolated from the host carrying 12 spacer-repeat units. We have found that this heterogeneous Cas9-crRNA complex cuts (+)strand of SP2 oligoduplex exactly at the same position as in the SP1 oligoduplex.

Figure 7:
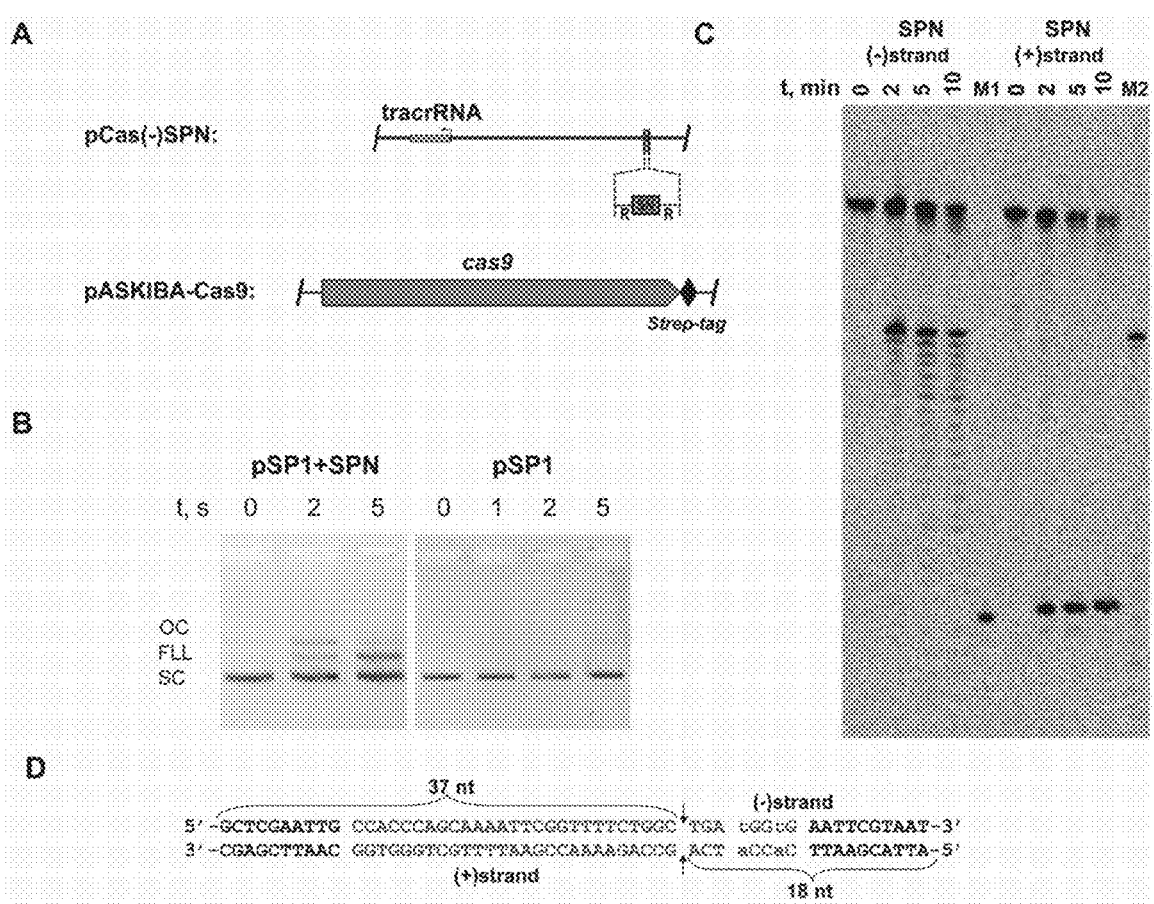
FIG. 7 shows reprograming of Cas9-crRNA complex. (A) Schematic representation of heterologous loci in two plasmids used for reprogramming of Cas9-crRNA complex. pCas(−)SPN were constructed from pCas9(−) plasmid (See part (A) of FIG. 2), by inserting new spacer sequence (SN) (5'-CC ACC CAG CAA AAT TCG GTT TTC TGG CTG-3' (SEQ ID NO: 16)) and inactivating Cas9 gene as described in (1). (B) Agarose gel analysis of plasmid DNA cleavage products. pSP1 and pSP1+SPN (pSP1 plasmid with inserted new proto-spacer and PAM over AatII site were incubated at 2.5 nM concentration with 2 nM of Cas9-crRNA complex in the reaction buffer (10 mM Tris-HCl pH=7.5, 10 mM NaCl, 10 mM MgCl2, 0.1 mg/ml BSA) at 37° C. for varied time intervals and reaction products analysed in the agarose gel. SC—super-coiled plasmid DNA, OC—open circular DNA nicked at one of DNA strands, FLL—full length linear DNA cut at both strands. (C) Oligoduplex SP1 cleavage. 2.5 nM of Cas9-crRNA complex and 1 nM SPN oligoduplex (Table S2) labeled with 33P at the 5'-end of either (+) or (—)strand were incubated in the reaction buffer (10 mM Tris-HCl pH=7.5, 10 mM NaCl, 10 mM MgCl2, 0.1 mg/ml BSA) at 37° C. M1—18 nt length marker Lanes M1 and M2 contain chemically synthesized 5'-end 33P-labeled 18 nt and 37 nt oligodeoxynucleotides corresponding to the cleavage products of (+) and (−) DNA strands, respectively. (D) Schematic representation of SPN oligoduplex substrate and cleavage products. SPN oligoduplex contains the new proto-spacer (red letters), PAM (blue letters). Cleavage positions are designated by arrows. Part (D) of FIG. 7 discloses SEQ ID NO: 39.

Cas9-crRNA cleavage specificity is directed by the crRNA sequence. To demonstrate directly that Cas9-crRNA complex specificity can be re-programmed by changing crRNA in the ribonucleoprotein complex we inserted a new spacer (SN) instead of spacer 51 in the CRISPR region generating pCas(−)SN plasmid containing only a minimal CRISPR region and tracrRNA encoding sequence (FIG. 7), co-expressed this plasmid together with pASKIBA-Cas9 and purified Cas9-crRNA complex. The cleavage specificity of Cas9-crRNA complex was analysed using plasmids pSP1+SPN and pSP1. pSP1+SPN plasmid containing the proto-spacer sequence matching the SN spacer in the CRISPR region, was linearized by the Cas9-crRNA complex, while pSP1 plasmid which lacks complimentary sequence remained intact (part (B) of FIG. 7). To determine the cleavage position within the SPN spacer sequence, we performed experiments with SPN oligoduplex, containing proto-spacer complementary to spacer SN and PAM (part (D) of FIG. 7). Oligoduplex cleavage assay confirmed (parts (C) and (D) of FIG. 7) that Cas9-crRNA complex with re-engineered specificity cleaves both DNA strands within the SN proto-spacer 3 nt upstream of the PAM identically to other Cas9-crRNA complexes.

The length of the spacer in the CRISPR3 region of *S. thermophilus* is 30 nt. According to the data provided in part (C) of FIG. 1, the mature crRNA copurified with the Cas9 protein is comprised of 42 nt. It means that only 20 nt of crRNA is complementary to the (+)strand of proto-spacer. To assess whether 5'-end of proto-spacer is important for the plasmid interference by the CRISPR3 system of *S. thermophilus* we engineered plasmids pSP1-27, pSP1-23, pSP1-19, pSP1-15, pSP1-11 with the 5'-truncated proto-spacer1 (the length of proto-spacer 27 bp, 23 bp, 19 bp, 15 bp, 11 bp, respectively), and analyzed transformation efficiency of the recipient strain containing pCRISPR3 (part (B) of FIG. 8). Plasmids containing 4 or 7 bp truncations at the 5' end of proto-spacer1, had no effect on the recipient strain ability to interfere with plasmid transformation. Shorter versions of proto-spacer (11, 15, 19 bp) abolished recipient strain ability to prevent plasmid transformation. These data shows that 5' end of the proto-spacer, which has no complementarity to mature crRNA is not important for CRISPR3/Cas function. In full support to the in vivo experiments, the SP1-20 oligoduplex containing only 20 nt of the protospacer-1 is efficiently cleaved by Cas9-crRNA (parts (D) and (E) of FIG. 8).

PAM is required for DNA binding and cleavage by Cas9-crRNA. Plasmids carrying a proto-spacer but not PAM (pSP1-pΔ) or multiple PAM's but no proto-spacer (pUC18) are resistant for Cas9-crRNA cleavage (part (A) of FIG. 8). Hence, in accordance with in vivo data both PAM and proto-spacer are required for double-stranded DNA cleavage by Cas9-crRNA complex (Sapranauskas et al., 2011. Nucleic Acids Res 39:9275-82). To find out, whether PAM is recognized in a context of a double-stranded or a single-stranded DNA, we analyzed Cas9-crRNA binding and cleavage of oligodeoxynucleotides i) SP1 (containing both proto-spacer and PAM), ii) SP1-Δp (contains only proto-spacer), and iii) SP2 (contains only PAM). The (+)strands of these oligodeoxynucleotides were used as single-stranded DNA substrates (s(+)SP1, s(+)SP1-Δp, s(+)SP2, accordingly) (Table 1).

Figure 9:
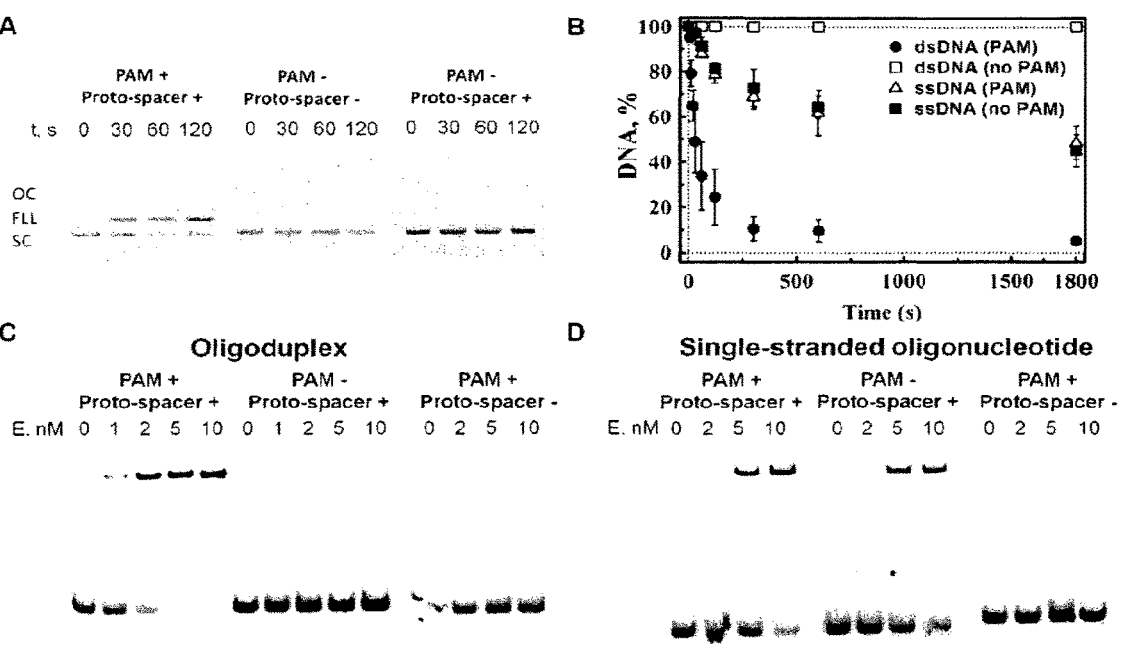
FIG. 9 shows PAM is required for in vitro DNA binding and cleavage by the Cas9-crRNA complex. (A) Agarose gel analysis of plasmid DNA cleavage products. Three different plasmids: PAM+Proto-spacer+ (pSP1 plasmid containing both the proto-spacer and PAM), PAM-Protospacer-(pUC18 plasmid containing multiple PAMs but no protospacer) and PAM-Protospacer+ (pSP1-pΔ (Sapranauskas et al., 2011. Nucleic Acids Res 39:9275-82) containing a proto-spacer without PAM) were incubated at 2.5 nM concentration with 2 nM of Cas9-crRNA complex in the reaction buffer (10 mM Tris-HCl pH=7.5, 10 mM NaCl, 10 mM MgCl2, 0.1 mg/ml BSA) at 37° C. for varied time intervals and reaction products analysed in the agarose gel. SC—super-coiled plasmid DNA, OC—open circular DNA nicked at one of DNA strands, FLL—full length linear DNA cut at both strands. (B) Time courses of (+)strand hydrolysis in the single-stranded and double-stranded oligodeoxynucleotides. Reactions containing 2 nM Cas9-crRNA and 1 nM of oligodeoxynucleotide were conducted at 37° C. in the reaction buffer (section A). SP1 (filled circles) and SP1-pΔ (open squares) oligoduplexes were used as dsDNA. s(+)SP1 (open triangles) and s(+) SP1-pΔ (filled squares) were used as ssDNA. (C) and (D) dsDNA and ssDNA (+)strand binding by Cas9-crRNA complex. The reactions contained 0.5 nM of the 33P-labelled ssDNA or dsDNA oligonucleotide, and the protein at concentrations as indicated above each lane. After 15 min at room temperature, the samples were subjected to PAGE for 2 h and analysed as described in 'Materials and Methods'

Consistent with the plasmid cleavage experiments, oligo-duplexes which have only proto-spacer, but not PAM are not cut by Cas9-crRNA (part (B) of FIG. 9). On the other hand, (+)strand in the single-stranded form is cut at the similar rate independently whether it has or has not PAM (part (B) of FIG. 9). These data clearly show that PAM is required only for a double-stranded but not for a single-stranded DNA cleavage.

To test if PAM is important for DNA binding by the Cas9-crRNA complex, electrophoretic mobility shift experiments were performed. To avoid cleavage, binding experiments were performed in the absence of Mg2+ ions which are necessary for cleavage. Cas9-crRNA showed different binding patterns for double-stranded and single-stranded oligonucleotides. In the case of the SP1 oligoduplex a low mobility complex is observed already at 1 nM concentration (part (C) of FIG. 9). On the other hand, no binding is observed under the same experimental conditions for oligo-duplexes without PAM (SP1-Δp) or without proto-spacer (SP2). Moreover, no low mobility complex is observed in the case of Cas9 protein without crRNA (part (A) of FIG. 6), confirming that crRNA is important for complex formation. Thus, taken together binding experiments clearly show that the Cas9 protein complex is unable to bind double-stranded DNA in the absence of PAM, even if it contains crRNA complementary to proto-spacer. To put it into other words, double-stranded DNA substrates lacking PAM are not cleaved because PAM is required for Cas9-crRNA binding.

On the other hand, single-stranded oligonucleotides ((+) strand) are bound by Cas9-crRNA with the same affinity independently of the PAM presence (part (D) of FIG. 9). Again, no binding was observed for single-stranded DNA oligonucleotide without proto-spacer (part (D) of FIG. 9), or for Cas9 protein lacking crRNA (part (C) of FIG. 6). Taken together these data indicate that Cas9-crRNA complex discriminates PAM only in the double-stranded but not a single-stranded DNA.

Figure 10:
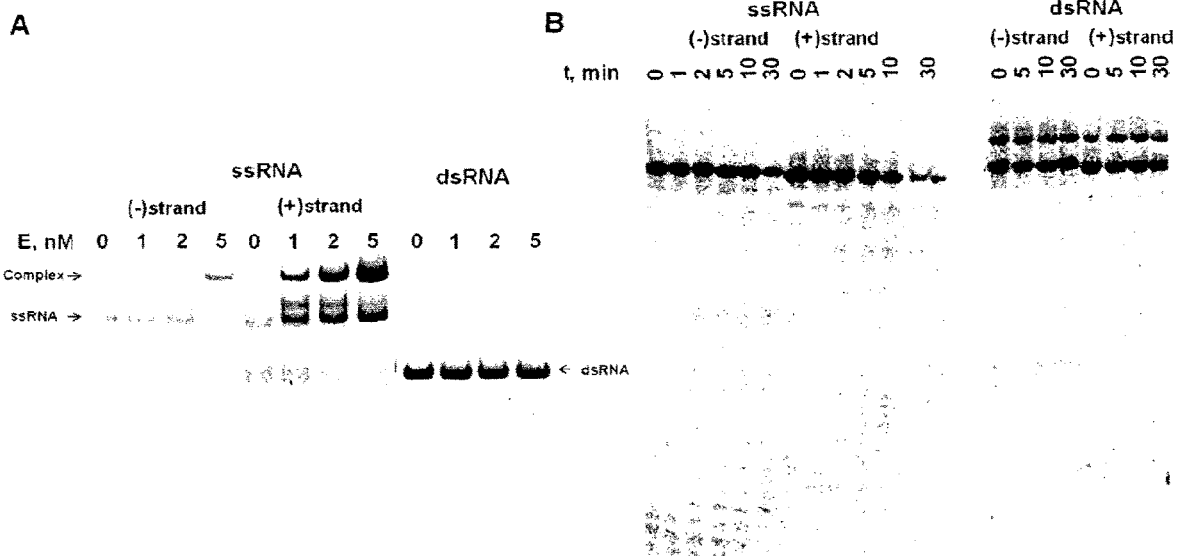
FIG. 10 shows RNA binding and cleavage analysis of Cas9-crRNA complex. (A) Electrophoretic mobility shift analysis (EMSA) of Cas9-crRNA complex binding to 84 nt RNA fragment containing proto-spacer-1, PAM and 24 nt flanking sequences on both sides. Left panel: RNA (—) strand; center panel: RNA (+) strand; right panel: double stranded RNA. RNA fragments used for analysis were generated by in vitro transcription (TranscriptAid™ T7 High Yield Transcription Kit, Fermentas) from PCR fragments with inserted T7 promoter at the front end of RNA coding sequence. PCR fragments coding (+) and (−) RNA strands were obtained from pSP1 plasmid (1) with following primer pairs accordingly: 5' taatacgactcactataGggtaccgagctcgaattg 3' (SEQ ID NO: 17)/5' GGGAAACAGCTATGACCAT-GATTACGAATTC-3' (SEQ ID NO: 18) and 5' gggtaccgagctcgaattgaaattcTAAACG 3' (SEQ ID NO: 19)/5' taatacgactcactataGggAAACAGCTATGACCATGATTACG 3' (SEQ ID NO: 20) (T7 RNA polymerase promoter underlined, transcription start on bold). The reactions contained 1 nM of the 33P-labelled RNA fragment, and the protein at concentrations as indicated above each lane. After 15 min at room temperature, the samples were subjected to PAGE for 2 h and analyzed as described in 'Materials and Methods'. (B) RNA cleavage assay. 2.5 nM of Cas9-crRNA complex was incubated in the reaction buffer (10 mM Tris-HCl pH=7.5, 10 mM NaCl, 10 mM MgCl2, 0.1 mg/ml BSA,) at 37° C. in the presence of 1 nM (+) and (−) RNA strands(left panel) or double stranded RNA labeled on (+) or (—) strand (right panel). Reaction products were analysed on denaturing PAA gel.

Since some Type III CRISPR systems provide RNA rather than DNA interference, we have studied RNA binding and cleavage by the Cas9-crRNA complex. The Cas9-crRNA did not cleave specifically either single-stranded RNA, or double-stranded RNA bearing a proto-spacer and PAM (part (B) of FIG. 10). This finding confirms confirms once more that DNA is a primary target for the CRISPR3/Cas system of *S. thermophilus*. Cas9-crRNA complex binds a comple-mentary RNA containing a proto-spacer, but this interaction is probably functionally not important, because single stranded RNA is not cleaved specifically by Cas9 within a proto-spacer.

Figure 11:
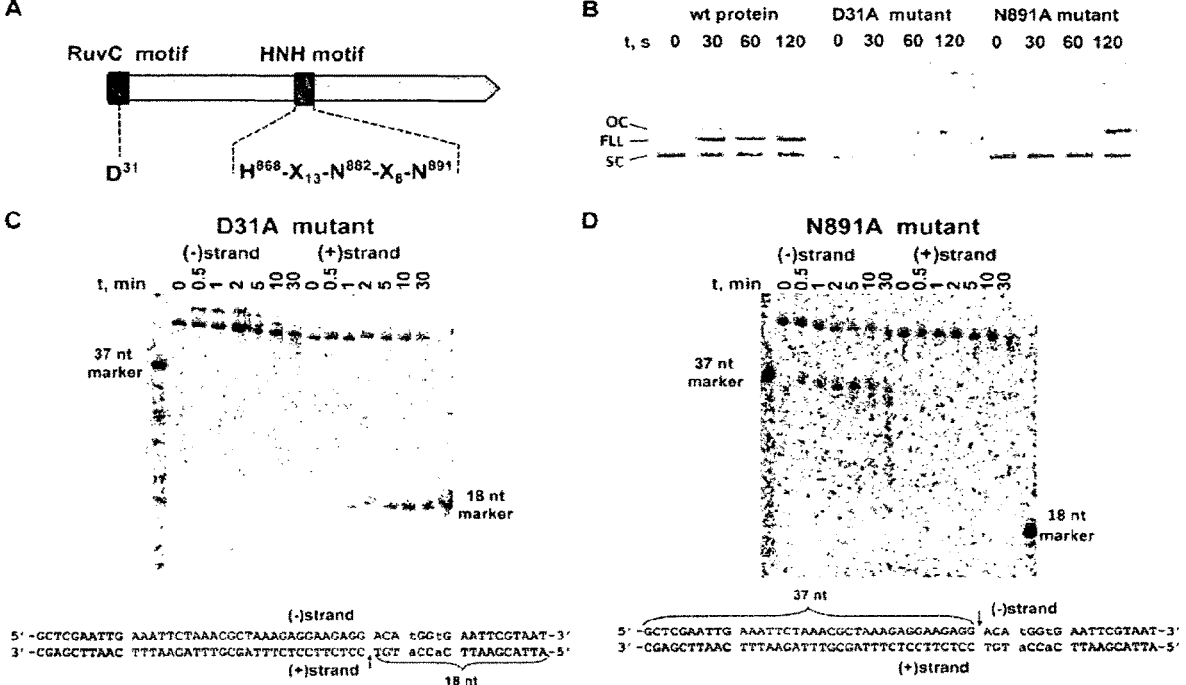
FIG. 11 shows RuvC and HNH active site motifs of Cas9 contribute to the cleavage of opposite DNA strands. (A) Localization of the conserved active site motifs within Cas9 protein. Amino acid residues identified as crucial for Cas9 in vivo activity (Sapranauskas et al., 2011. Nucleic Acids Res 39:9275-82) are indicated. (B). Agarose gel analysis of pSP1 plasmid cleavage by Cas9 and mutant proteins. Reactions were performed as described in and 'Materials and Methods' (C) Strand preference of D31A mutant. Reactions were performed as described in part (A) of FIG. 2 and 'Materials and Methods'. D31 mutant cleaves only (+)strand of SP1 oligoduplex. Part (C) of FIG. 11 discloses SEQ ID NOS 31. (D) Strand preference of N891A mutant. N891 mutant cleaves only (−) strand of SP1 oligoduplex. Cleavage positions are designated by arrows. Part (D) of FIG. 11 discloses SEQ ID NOS 31.

Mutagenesis of Cas9 protein RuvC and HNH motifs. Plasmid transformation experiments indicate that RuvC and HNH motifs (part (A) of FIG. 11) are important for Cas9 function (Sapranauskas et al., 2011. Nucleic Acids Res 39:9275-82). To test if these motifs are involved in the target DNA cleavage, we expressed and purified D31A and N891A mutants following procedure described for wt Cas9. Both mutants co-purified with crRNA identical to crRNA in the wt Cas9 complex (part (C) of FIG. 11). To test whether mutant proteins retained cleavage activity, we monitored pSP1 plasmid cleavage by mutant Cas9-crRNA complexes. Surprisingly, instead of linear reaction product observed for the wt Cas9 protein, both mutants produced nicked DNA form (part (B) of FIG. 11) indicating that both active sites mutants cleave only one DNA strand of plasmid substrate within a proto-spacer.

Figure 12:
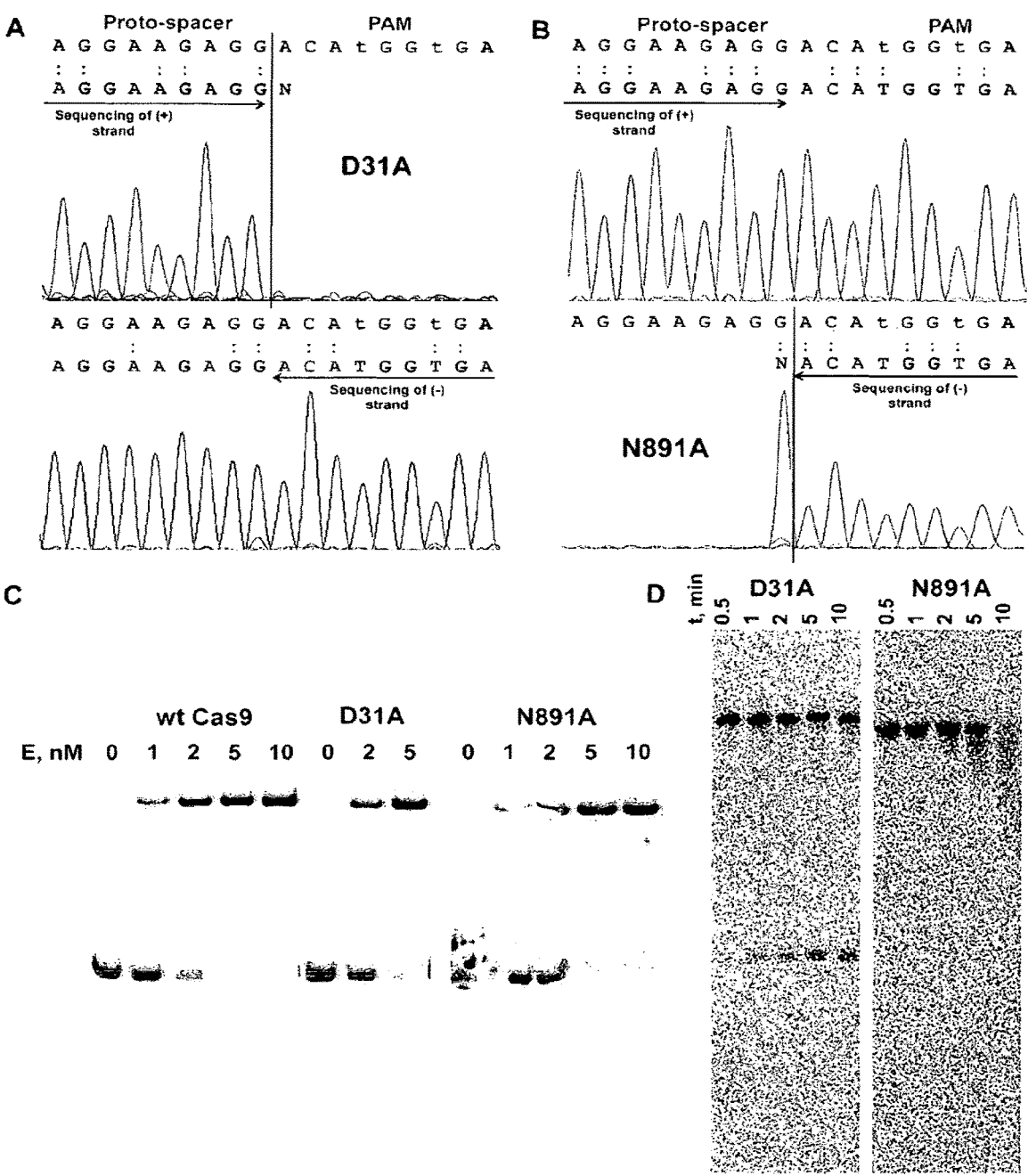
FIG. 12 shows properties of Cas9 active site mutant-crRNA complexes. (A) Direct sequencing of reaction products obtained with Cas9 mutant D31A (RuvC-like active site motif). Part (A) of FIG. 12 discloses SEQ ID NOS 58, 59, 58, and 58, respectively, in order of appearance. (B) Direct sequencing of reaction products obtained with Cas9 N891A mutant (HNH-like active site motif). Part (B) of FIG. 12 discloses SEQ ID NOS 58, 58, 58, and 60, respectively, in order of appearance. (C) SP1 oligoduplex binding by the wt Cas9-crRNA and active site mutant complexes. (D) Cleavage of (+)SP1 strand by Cas9-crRNA mutant complexes.

To determine whether mutant proteins exhibit a strand preference, we analysed D31A and N891A mutant cleavage of the SP1 oligoduplex. RuvC active site mutant (D31A) cut (+)strand of oligoduplex at the same position as wt Cas9-crRNA protein, while the (−)strand stayed intact (part (C) of FIG. 11). And vice versa, HNH active site mutant (N891A) cleaved only (−)strand, but not (+)strand of the SP1 oligo-duplex (part (D) of FIG. 11). Taken together these data indicate that RuvC and HNH active sites act on opposite DNA strands to generate a double strand break. To test, whether the same cleavage pattern is conserved during the plasmid DNA cleavage, we sequenced proto-spacer regions of nicked plasmids. Run-off sequence data confirmed that RuvC active site mutant cut only (+) DNA strand while HNH/McrA mutant − only (−)strand (parts (A) and (B) of FIG. 12). Furthermore, we found that RuvC mutant cleaved (+)strand of a single-stranded DNA but no such cleavage was detected for the HNH mutant (part (D) of FIG. 12).

Figure 13:
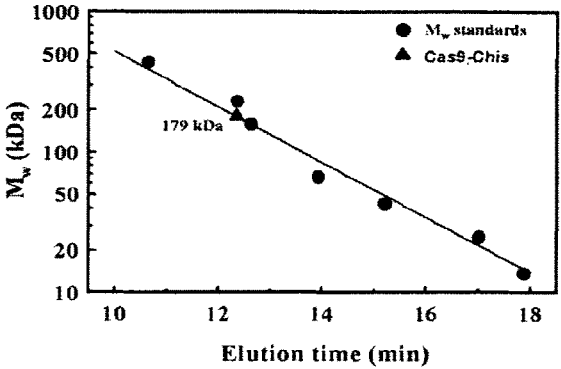
FIG. 13 shows molecular mass of the wt Cas9-Chis protein. Gel filtration experiments were carried out at room temperature using Superdex 200 10/300 GL column (GE healthcare) pre-equilibrated with 10 mM sodium phosphate (pH 7.4) buffer containing 500 mM sodium chloride. The apparent Mw of Cas9 (black triangle) were calculated by interpolation from the standard curve obtained using a set of proteins of known Mw (black circles) (Bio-Rad Gel Filtration Standards).

To test whether mutations altered DNA-binding affinity of mutant protein-crRNA complexes, DNA binding was stud-ied using the electrophoretic mobility shift assay. Both mutant protein-crRNA complexes bound oligoduplex SP1 with the same affinity as wild type protein (part (C) of FIG. 12). Thus, mutations in the putative active sites of Cas9 have no significant effect on double-stranded DNA-binding prop-erties of the Cas9-crRNA complex. Since 42 nt crRNA was present in the mutant protein complexes (part (C) of FIG. 12), we conclude that mutant Cas9-crRNA complexes lost ability to cut one of the target DNA strand due to active site mutation. Since Cas9-HisTag protein is a monomer in solu-tion (FIG. 13), it is likely that Cas9 protein is functional as a monomer and uses two active sites for the cleavage of opposite DNA strands. Similar strategy is exploited by some restriction endonucleases (Armalyte et al., 2005. J Biol Chem 280: 41584-94).

Discussion

Figure 8:
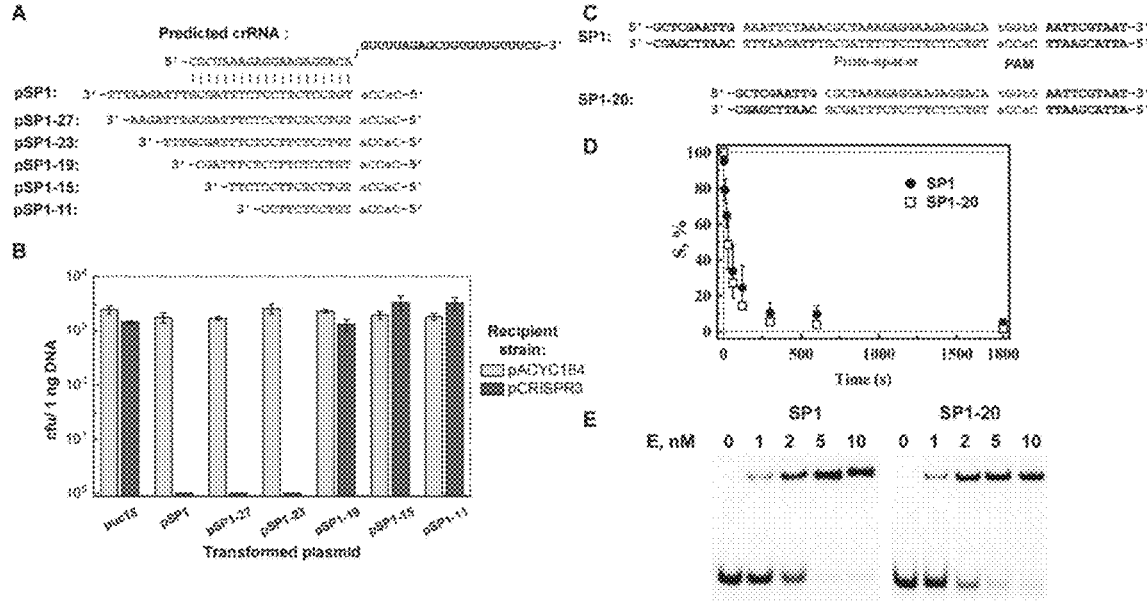
FIG. 8 shows impact of spacer length on CRISPR-encoded immunity. (A) Schematic representation of shortened versions of proto-spacers inserted in the transformed plasmids. Part (A) of FIG. 8 discloses SEQ ID NOS 7 and 61-66, respectively, in order of appearance. (B) Effect of proto-spacer length on the plasmid transformation efficiency. Transformation efficiency is expressed as cfu per nanogram of plasmid DNA (mean±SD). (C). Schematic representation of oligoduplexes used in the in vitro cleavage and binding experiments. Part (C) of FIG. 8 discloses SEQ ID NOS 31 and 38, respectively, in order of appearance. (D) Time courses of the 27 bp oligoduplex (full length proto-spacer SP1, filled circles) and the 20 bp oligoduplex (truncated protospacer SP1-20, square) cleavage by the Cas9-crRNA complex. (E) Electrophoretic mobility shift assay of SP1 and SP1-20 oligoduplex binding by the Cas9-crRNA complex.

Cas9-crRNA complex of CRISPR3/Cas system of *S. thermophilus* is crRNA-guided endonuclease. This work demonstrates that Cas9-crRNA complex of CRISPR3/Cas system of *S. thermophilus* is crRNA-directed endonuclease which cuts both DNA strands in the presence of Mg2+-ions within a protospacer 3 nt downstream of the PAM sequence to produce blunt end cleavage products. Sequence specific-ity of the Cas9-crRNA complex is dictated by the 42 nt crRNA which include ~20 nt fragment complementary to the proto-spacer sequence in the target DNA. In this respect the mature crRNA in the Cas9 complex of CRISPR3/Cas system of *S. thermophilus* is similar to crRNA of *Streptococcus pyogenes* which has a 3'-handle of repeat sequence but lacks part of the spacer sequence and 5'-handle corresponding to the repeat fragment (Deltcheva et al, 2011). Therefore, crRNA present in the Cas9-crRNA complex of CRISPR3/Cas system of *S. thermophilus* is complementary only to the part of the proto-spacer sequence distal to PAM. Not sur-prisingly, truncation of the 3'-end of the proto-spacer sequence by 10 nucleotides has no effect on Cas9-crRNA cleavage of synthetic oligoduplexes or plasmid DNA (FIG. 8).

The cleavage machinery of Cas9-crRNA complex resides in the Cas9 protein which provides two active sites for the phosphodiester bond cleavage. The RuvC- and HNH-like active sites of Cas9 protein are located on different domains and act independently on individual DNA strands. Alanine replacement of the active site residues in the RuvC- and HNH-motifs transforms Cas9-crRNA complex into a strand-specific nicking endonucleases similar to the nicking enzymes (Chan et al., 2011. Nucleic Acids Res 39:1-18). Consistent with in vivo studies, a functional activity of the Cas9-crRNA complex in vitro is absolutely dependent on the presence of the proto-spacer adjacent motif NGGNG upstream of the proto-spacer sequence. Data presented in the FIG. 3 show that PAM is required for Cas9-crRNA binding to the double-stranded DNA. If PAM sequence is missing in double-stranded DNA, the Cas9-crRNA complex does not bind such DNA even if it contains a complementary proto-spacer sequence. On the other hand, Cas9-crRNA does not display DNA binding if PAM (or multiple PAM's) is present but proto-spacer sequence is absent. Thus, in consistence with the in vivo data, both PAM and proto-spacer sequences are necessary prerequisite for double-stranded DNA binding and subsequent cleavage. Contrary to the Cas9-crRNA bind-ing to the double-stranded DNA, PAM sequence motif has no effect on the single-stranded DNA binding by: a single-stranded oligodeoxynucleotide containing proto-spacer with or without PAM sequence is bound equally well but with lower affinity than double-stranded DNA. In the presence of Mg2+ ions Cas9 cuts single-stranded DNA bound to the crRNA using its HNH-active site.

Figure 14:
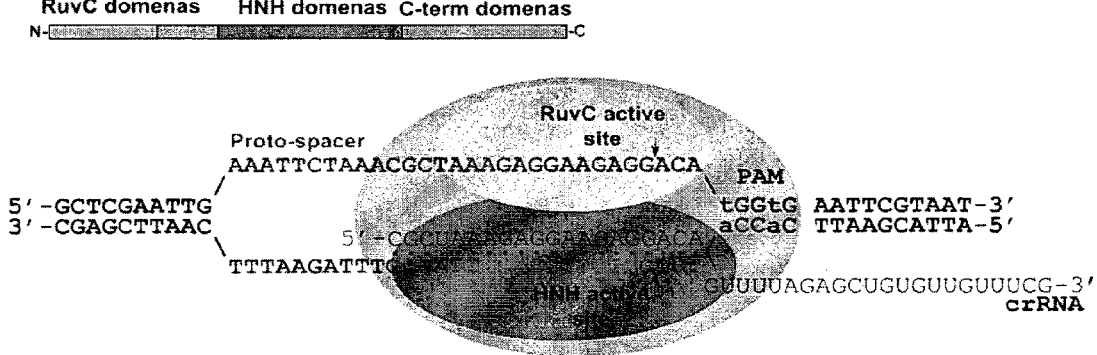
FIG. 14 shows schematic arrangement and mechanism of crRNA-directed DNA cleavage by the Cas9-crRNA complex. Domain architecture of Cas9 is shown schematically on the top. Cas9-crRNA complex binds to the dsDNA containing PAM. crRNA binds to the complementary (+)strand resulting in DNA strand separation and the R-loop formation. In the ternary complex RuvC active site of Cas9 is positioned at the scissile phosphate on the unpaired (−)strand, while HNH active site is located at the scissile phosphate on the DNA (+)strand bound to crRNA. Coordinated action of both active sites results in the double strand break 3 nt away from the 5'-NGGNG-5' PAM generating blunt end DNA.
Figure 15:
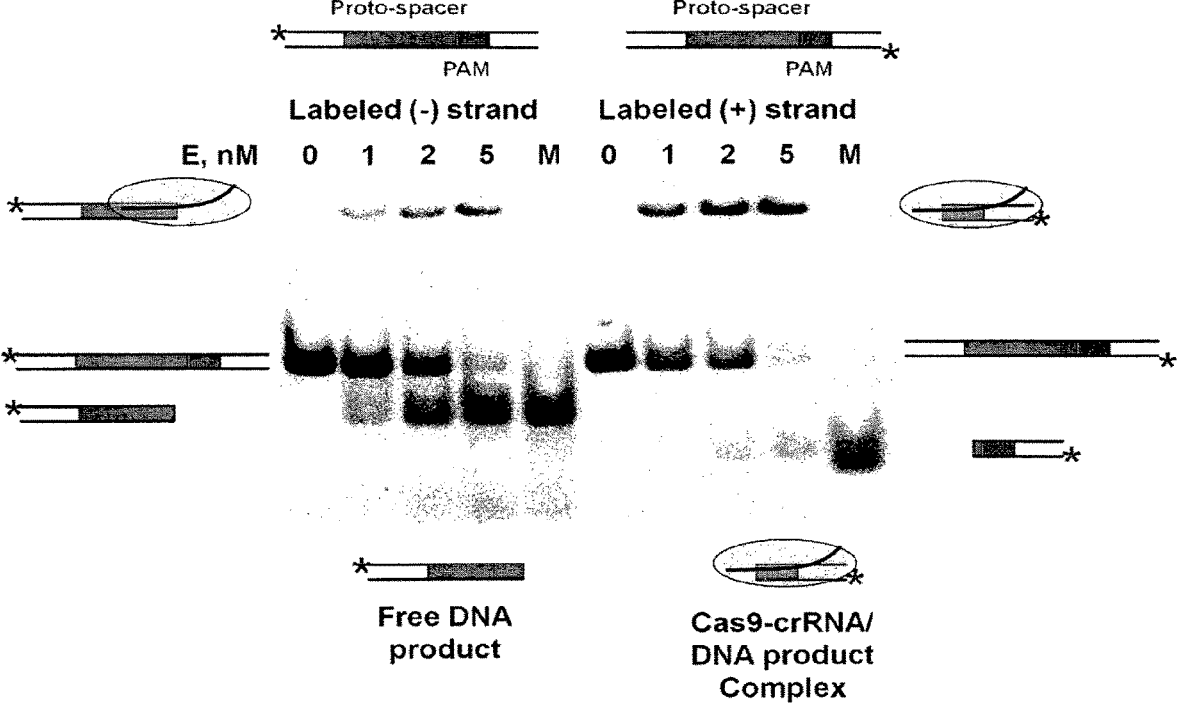
FIG. 15 shows native electrophoresis of Cas9-crRNA and cleavage products. The protein at concentrations as indicated above each lane, where incubated in the reaction buffer (10 mM Tris-HCl pH=7.5, 10 mM NaCl, 10 mM MgCl2, 0.1 mg/ml BSA) at 37° C. for 30 min in the presence of 0.5 nM SP1 oligoduplex. Samples was mixed with loading dye solution (0.01% bromphenol blue and 75 mM EDTA in 50% v/v glycerol) and analysed by non-denaturing PAGE. The gel lanes marked M—melted form of cleavage reactions products. The cartoons in each side of the gel illustrate protein-DNA complexes and DNA that correspond to each band, while cartoons below the gel illustrate major substrate form after reaction.

Mechanism of DNA interference in the Type II systems. Our results establish a simple model for the mechanism of double-stranded DNA cleavage by Cas9-crRNA complex in the *S. thermophilus* CRISPR3/Cas system (FIG. 14). Cas9-crRNA complexes using a mechanism that yet has to be defined locates and binds to a proto-spacer sequence within the double-stranded DNA in a PAM-dependent process. It is possible that PAM in the double-stranded DNA serves as an initiation site (signal) for the strand separation and promotes subsequent pairing of crRNA to the complementary (+)strand of DNA. It remains to be established whether a Cas9 protein module or Cas9-bound crRNA (for example, using nucleotides in the conserved the "3'-handle" of the conserved repeat sequence) recognizes the PAM sequence. Despite of the lack of these mechanistic details, our data clearly demonstrate that PAM is recognized by Cas9-crRNA in the context of double-stranded DNA. The Cas9-crRNA binding to the target sequence in the ds DNA presumably results in the R-loop structure where (–)strand is displaced and the complementary (+) DNA strand is paired to the crRNA. In the presence of Mg2+ ions phosphodiester bond cleavage occurs on both strands 3 nt 5'-upstream of the PAM sequence to generate blunt DNA ends. DNA cleavage analysis by the RuvC- or HNH-motif mutants demonstrate that RuvC- and HNH-like active sites of Cas9 protein act on the (–) and (+)strands, respectively. Therefore, in the catalytically competent the Cas9-crRNA complex, the N-terminal domain containing the catalytic D31A residue of the RuvC motif is positioned at the displaced (—) DNA strand, while the central part of Cas9 containing the HNH motif is located in the vicinity of the scissile phosphodiester bond of (+) DNA strand paired to crRNA. After DNA cleavage Cas9-crRNA remains bound to the reaction products (FIG. 15). Taken together data presented here suggest a first molecular mechanism for the DNA interference step by the CRISPR3/ Cas system of *S. thermophilus*. Since cas9 is a signature gene (Makarova et al., 2011. Nat Rev Microbiol 9:467-77) for Type IIA and Type IIB systems the cleavage mechanism proposed here is likely to be conserved in other Type IIA and Type IIB systems. Stand-alone versions of Cas9-like proteins which are not a part of the CRISPR system were identified by bioinformatics (Makarova et al., 2011. Biol Direct 6: 38). In the light of the data provided here we suggest that these proteins can provide interference against foreign DNA similarly to Cas9 if loaded with small crRNA molecules which may be generated through the pathway different from CRISPR.

Comparison to other RNA interference complexes. The mechanism proposed here for the double-stranded DNA cleavage by the Cas9-crRNA complex differs significantly from that for the Type I-E (former Ecoli or CASS2) system (Jore et al., 2011. Nat Struct Mol Biol 18:529-36). In the *E. coli* system crRNA and Cas proteins assemble into a large ribonucleoprotein complex named Cascade that facilitates target recognition by enhancing sequence-specific hybridization between the CRISPR RNA and complementary target sequences (Jore et al., 2011. Nat Struct Mol Biol 18:529-36). Target recognition is dependent on PAM and governed by the "seed" crRNA sequence located at the 5'-end of the spacer region (Semenova et al., 2011. Proc Natl Acad Sci USA 108:10098-103). However, while Cascade-crRNA complex alone is able to bind double-stranded DNA containing PAM and proto-spacer, it requires an accessory Cas3 protein for DNA cleavage. Cas3 is a single-stranded DNA nuclease and helicase which is able to cleave single-stranded DNA producing multiple cuts (Sinkunas et al., 2011. EMBO J 30:1335-42). The mechanistic details of the Cas3 action on a proper biological substrate (e.g., Cascade-crRNA bound to the double-stranded DNA in the R-loop like complex) have yet to be established. However, it has been demonstrated recently that Cas3 of M. jannaschii alone is able to cut both DNA strands in the synthetic substrate mimicking R-loop (Beloglazova et al., 2011. EMBO J 30:616-27). It is proposed that Cas3 may follow similar mechanism for DNA cleavage in the presence of Cascade-crRNA complex. Thus, current data clearly show that mechanistic details of the interference step for the Type I-E system differs from that of CRISPR3 system both by the catalytic machinery and mechanism and complexity.

In the III-B subtype CRISPR systems present in many archea and some bacteria, Cas module RAMP (Cmr) proteins and cRNA assemble into the effector complex that targets invading RNA (Hale et al., 2009. Cell 139:945-56; Hale et al., 2012. Mol Cell 45:292-302). In *Pyrococcus furiosus* RNA silencing complex comprised of six Cmr1-6 proteins and crRNA binds to the target RNA and cuts it at fixed distance in respect to 3'-end the psiRNA. The cleavage activity depends on Mg2+-ions however individual Cmr protein(-s) responsible for target RNA cleavage has yet to be identified. The effector complex of *Sulfolobus solfataricus* comprised of seven Cmr1-7 proteins and crRNA cuts invading RNA in an endonucleolytic reaction at UA dinucleotides (Zhang et al., 2012. Mol Cell 45: 303-13). Importantly, both Cmr-crRNA complexes perform RNA cleavage in a PAM independent manner.

The data provided here show that Cas9-crRNA complex of CRISPR3 system is so far the most simple DNA interference system comprised of a single Cas9 protein bound to the crRNA molecule. The simple modular organization of the Cas9-crRNA complex where specificity for DNA target is encoded by the crRNA and cleavage machinery is brought by the Cas protein provides a versatile platform for engineering of universal RNA-guided DNA endonucleases.

Example 2

In Vitro Assembly of Cas9-crRNA Complex from 4 Components

In this example we demonstrate that the catalytically active Cas9-crRNA complex can be assembled in vitro by mixing 4 individual components: the C-terminal 6×His-tagged variant of Cas9 protein ("6×His" disclosed as SEQ ID NO: 23), tracrRNA transcript (SEQ ID NO: 5), CRISPR RNA transcript (SEQ ID NO: 8) and *E. coli* RNAseIII (Abgene). Cas9 protein is first pre-incubated with tracrRNA and CRISPR RNA transcripts, followed by the subsequent incubation with RNAseIII to generate a catalytically competent Cas9-crRNA complex which is used for the site-specific DNA cleavage.

More specifically, RNA fragments required for complex assembly were produced by in vitro transcription (Transcrip-tAid™ T7 High Yield Transcription Kit, Fermentas) of PCR-generated fragment containing a T7 promoter at the proximal end of RNA coding sequence. PCR-generated DNA fragments encoding CRISPR RNA and tracrRNA were produced using pCas9(–)SP1 plasmid as a template with a following primer pair: 5'-taatacgactcactataGggtagaaaaga-tatcctacgagg-3' (SEQ ID NO: 40)/5'-CAACAAC-CAAGCTAATACAGCAG-3' (SEQ ID NO: 41) and 5'-aaaaacaccgaatcggtgccac-3' (SEQ ID NO: 42)/5'-taatacgactcactataGggTAATAATAATTGTGGTTTGAAAC- CATTC-3'(SEQ ID NO: 43) (T7 RNA polymerase promoter underlined, transcription start shown in bold). The 150 nt CRISPR RNA transcript is comprised of 102 nt Repeat-Spacer1-Repeat sequences flanked by the 23 nt upstream and 25 nt downstream regions required for primer annealing. The 105 nt transcript of tracrRNA is comprised of a 38 nt stretch partially complimentary to the *S. thermophilus* DCGG7710 CRISPR3 repeat sequence fragment (anti-repeat sequence), flanked by the 16 nt upstream and 51 nt downstream region. RNA fragments produced by in vitro transcription were purified using RNeasy MinElute Cleanup Kit (Qiagen).

For in vitro assembly of catalytically competent Cas9-crRNA complex, the 6×His-tagged Cas9 protein ("6×His" disclosed as SEQ ID NO: 23) was mixed with CRISPR RNA and tracrRNA transcripts at 1:0.5:1 molar ratio and pre-incubated in a buffer containing 10 mM Tris-HCl (pH 7.5 at 37° C.), 100 mM NaCl at 37° C. for 30 min followed by addition of RNAseIII (Ambion), MgCl2 and DTT and subsequent incubation for additional 30 min. The final concentrations of the components in the assembly mix were the following: 100 nM of 6×His-tagged Cas9 protein ("6×His" disclosed as SEQ ID NO: 23), 50 nM of CRISPR RNA, 100 nM of tracrRNA, 50 nM RNAseIII, 10 mM MgCl2 and 1 mM DTT.

Below we provide experimental evidences that in vitro assembled Cas9-crRNA complex guided by the crRNA sequence cleaves DNA at the specific site to generate blunt ends. In this respect Cas9-crRNA complex can be used an alternative for a restriction endonuclease or meganuclease for the site-specific DNA cleavage in vitro. The sequence specificity of the complex is dictated by the crRNA sequence which can be engineered to address a desirable DNA target.

Figure 16:
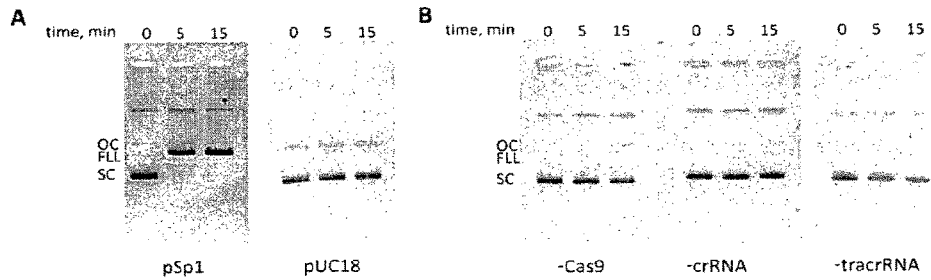
FIG. 16 shows plasmid DNA cleavage by Cas9-crRNA complex. (A) pSP1 and pUC18 plasmid DNA cleavage. Cas9-crRNA complex was incubated with pSP1 and pUC18 plasmids in a reaction buffer provided in the Example 1. pSP1 plasmid contained a proto-spacer1 sequence flanked by the the 5'-NGGNG-3' PAM sequence. Proto-spacer1 sequence was not present in pUC18. Reaction products were analysed in the agarose gel. Under these conditions pSP1 plasmid is converted into a linear form while pUC18 plasmid lacking proto-spacer1 sequence is resistant to cleavage. (B) pSP1 cleavage reactions in the absence of one of the components. In the reaction mixes lacking one of the components (Cas9, crRNA or tracrRNA, respectively) pSP1 plasmid is not cleaved. SC—super-coiled plasmid DNA, OC—open circular DNA nicked at one of DNA strands, FLL—full length linear DNA cut at both strands.

First, the DNA cleavage activity of the in vitro assembled Cas9-crRNA complex was assayed on the plasmid substrates pSP1 and pUC18. The pSP1 plasmid contained a proto-spacer1 sequence flanked by the 5'-NGGNG-3' PAM sequence. Proto-spacer1 sequence was not present in pUC18. Reactions on pUC18 and pSP1 plasmids (Sapranauskas et al., 2011. Nucleic Acids Res 39:9275-82) were conducted at 37° C. in the 10 mM Tris HCl (pH 7.5 at 37° C.), 50 mM NaCl, 0.05 mg/ml BSA, 0.5 mM DTT and 10 mM MgCl2. Reaction mixtures typically contained 3.0 nM of supercoiled plasmid DNA. The reactions were initiated by mixing 50 μl volumes of Cas9-crRNA complex and plasmid DNA (1:1 v/v ratio) in a reaction buffer. Aliquots were removed at timed intervals and quenched with phenol/chloroform. The aqueous phase was mixed with loading dye solution (0.01% bromphenol blue and 75 mM EDTA in 50% v/v glycerol) and reaction products analyzed by electrophoresis through agarose (FIG. 16). To check whether the pSP1 plasmid pre-cleaved by Cas9-crRNA complex can be re-ligated, we purified linear pSP1 cleavage product from agarose gel using GeneJET gel extraction Kit (Fermentas) and re-ligated using T4 DNA ligase (Fermentas). After transformation of *E. coli* cells by the ligation mix, five individual clones were selected from resulting transformants, plasmid DNA was purified and subjected to sequencing using the following primers: 5'-ccgcatcaggcgccattcgcc-3' (SEQ ID NO: 29) (sequencing of (+)strand) and 5'-gcgaggaagcggaagagcgccc-3' (SEQ ID NO: 30) (sequencing of (−)strand). Sequence analysis revealed that the DNA sequence of the pSP1 plasmid in the locus that was cleaved by Cas9-crRNA complex and re-ligated was identical to the sequence of the non-treated plasmid. *E. coli* transformation by the ligation mix in the absence of T4 DNA ligase did not produce transformants indicating that no traces of super-coiled plasmid are co-purified with the linear reaction product.

Next, the cleavage activity of the in vitro assembled Cas9-crRNA complex was assayed on a synthetic 55 bp oligodeoxynucleotide duplex SP1 containing a proto-spacer sequence matching to the spacer sequence of crRNA (FIG. 17). Reactions conditions were identical to those described above for the plasmid DNA cleavage, except that 1 nM of oligoduplex was used. Reaction product analysis revealed that in vitro assembled Cas9-crRNA complex cleaved both strands of the oligoduplex at fixed position, inside the proto-spacer, after the 37th nucleotide from the 5'-terminus, 3 nt upstream of the PAM sequence 5'-NGGNG-3' leaving blunt ends (FIG. 17).

Example 3

In Vitro Assembly of Cas9-crRNA Complex from 3 Components

In this example we demonstrate that active Cas9-crRNA complex can be assembled in vitro by mixing 3 individual components: the C-terminal 6×His-tagged variant of Cas9 protein ("6×His" disclosed as SEQ ID NO: 23), tracrRNA transcript provided in Example 1 (SEQ ID NO: 5 and SEQ ID NO: 6), and CRISPR RNA transcript (SEQ ID NO: 8) provided in Example 1 or synthetic crRNA (SEQ ID NO: 7) which corresponds to the putative crRNA of CRISPR3/Cas system of *S. thermophilus* DGCC7710 strain. Synthetic 42 nt oligoribonucleotide is comprised of 20 nt of identical to the spacer1 of CRISPR3 region at the 5' terminus and 22 nt of repeat sequence at the 3' end. More specifically, tracrRNA and CRISPR RNA transcripts were obtained as described in Example 1. To generate the Cas9-crRNA complex the 6×His-tagged Cas9 protein ("6×His" disclosed as SEQ ID NO: 23) was mixed with tracrRNA and CRISPR RNA transcript, or 42 nt synthetic crRNA, at 1:0.5:1 molar ratio and incubated in a buffer containing 10 mM Tris-HCl (pH 7.5 at 37° C.), 100 mM NaCl at 37° C. for 1 h. The final concentrations of the components in the assembly mix were the following: 100 nM of 6×His-tagged Cas9 protein ("6×His" disclosed as SEQ ID NO: 23), 50 nM of CRISPR RNA or 42 nt synthetic crRNA, 100 nM of tracrRNA.

Below we provide experimental evidences that in vitro assembled Cas9-crRNA complex guided by the crRNA sequence cleaves DNA at the specific site to generate blunt ends. In this respect Cas9-crRNA complex can be used an alternative for a restriction endonuclease or meganuclease for the site-specific DNA cleavage in vitro. The sequence specificity of the complex is dictated by the crRNA sequence which can be engineered to address a desirable DNA target.

First, the DNA cleavage activity of the in vitro assembled Cas9-crRNA complex was assayed on the plasmid substrates pSP1 and pUC18. The pSP1 plasmid contained a proto-spacer1 sequence flanked by the 5'-NGGNG-3' PAM sequence. Proto-spacer1 sequence was not present in pUC18. Reactions on plasmid substrates (Sapranauskas et al., 2011. Nucleic Acids Res 39:9275-82) were conducted at 37° C. in the 10 mM Tris-HCl (pH 7.5 at 37° C.), 50 mM NaCl, 0.05 mg/ml BSA, 0.5 mM of DTT and 10 mM MgCl2. Reaction mixtures typically contained 3.0 nM of supercoiled plasmid DNA. The reactions were initiated by mixing 50 μl volumes of Cas9-crRNA complex and plasmid DNA (1:1 v/v ratio) in a reaction buffer. Aliquots were removed at timed intervals and quenched with phenol/chloroform. The aqueous phase was mixed with loading dye solution (0.01% bromphenol blue and 75 mM EDTA in 50% v/v glycerol) and reaction products analyzed by electrophoresis through agarose (FIG. 18).

Next, the cleavage activity of the in vitro assembled Cas9-crRNA complex was assayed on a synthetic 55 bp oligodeoxynucleotide duplex SP1 containing a a proto-spacer sequence matching to the spacer sequence of crRNA (FIG. 19). Reactions conditions were identical to those described above for the plasmid DNA cleavage, except that 1 nM of oligoduplex was used. Reaction product analysis revealed that in vitro assembled Cas9-crRNA complex cleaved both strands of the oligoduplex at fixed position, inside the proto-spacer, after the 37th nucleotide form the 5'-end, 3 nt upstream of the PAM sequence 5'-NGGNG-3' leaving blunt ends (FIG. 19).

Example 4

Interchangeable Spacer Cassette for the Re-Programing of the Cas9-crRNA Complex Specificity.

In this example we describe an interchangeable spacer cassette which allows to produce crRNA carrying a nucleotide sequence against any desirable DNA target to be used for assembly of the Cas9-crRNA complex described in Examples 1 and 2 (part (B) of FIG. 20). The cassette caries a single repeat-spacer-repeat unit which allows insertion of the oligoduplex carrying the new spacer sequence required to generate a desired crRNA. To engineer a cassette, first we constructed a cassette containing a leader sequence, a repeat sequence and a unique SapI recognition site in the vicinity of the repeat sequence followed by BamHI site (part (C) of FIG. 20). To generate CRISPR region containing the unique desired spacer, we inserted a synthetic oligoduplex containing a unique spacer sequence and a repeat unit into the plasmid precleaved with SapI and BamHI restriction enzymes. Using this cassette we produced crRNA transcripts which contained nucleotide sequences complementary to the proto-spacers N1 and N2 present in pUC18 plasmid (see below).

As proof of the principle demonstration, we used an interchangeable spacer cassette to generate crRNA1 and crRNA2 which were engineered to target pUC18 plasmid at proto-spacer1 and proto-spacer2, respectively, incorporated crRNA1 and crRNA2 into Cas9 complex as described in the Example 1 and used these complexes for the cleavage of pUC18 plasmid. The proto-spacer N1 is located near the SapI restriction endonuclease site, while the proto-spacer N2 is in the vicinity of AatII site. The distance between SapI and AatII restriction sites is 775 bp, while the distance between the putative Cas9-crRNA complex cleavage sites located in the spacers N1 and N2 is 612 bp (part (A) of FIG. 21). The crRNA1 and crRNA2 PCR fragments containing T7 promoter at the proximal end were obtained from the corresponding interchangeable spacer cassette plasmids and used to produce by in vitro transcription CRISPR RNA transcripts carrying sequences matching spacer N1 or spacer N2 sequences. The catalytically active complexes of Cas9 with crRNA1 and crRNA2 were assembled for DNA cleavage as described in Example 1. In vitro assembled complexes containing either crRNA1 or crRNA2 linearized pUC18 plasmid (part (B) of FIG. 21). When both complexes were incubated with the pUC18plasmid, two DNA fragments (2074 and 612 bp) were obtained (part (B) of FIG. 21), indicating that plasmid cleavage occurred at sites targeted by the crRNA molecules present in the complexes.

Example 5

Cloning Procedure Using Cas9-crRNA Complex.

In this example we demonstrate that Cas9-crRNA complex may be used to prepare a vector for cloning procedure. First we demonstrated that cleavage products obtained by the Cas9-crRNA complex can be re-ligated by DNA ligase. We purified linear pSP1 cleavage product from agarose gel and re-ligated it using DNA ligase. After transformation of *E. coli* cells by the ligation mix, five individual clones were selected from resulting transformants, plasmid DNA was purified and subjected to sequencing. Sequence analysis revealed that the DNA sequence of the pSP1 plasmid in the locus that was cleaved by Cas9-RNA complex and re-ligated was identical to the sequence of the non-treated plasmid. *E. coli* transformation by the ligation mix in the absence of T4 DNA ligase did not produce transformants indicating that no traces of supercoiled plasmid are co-purified with the linear reaction product. This result illustrates, that the DNA ends generated by the Cas9 cleavage are substrates for T4 DNA ligase, and therefore must contain a phosphate at the 5' terminus and a free OH group at the 3' terminus (Lehman 1974. Science 186:790-7).

Next we analyzed cleavage of pUC18 plasmid with Cas9 complex loaded with crRNA1 and crRNA2 described in Example 5 (part (A) of FIG. 21). First, pUC18 was cleaved with one complex, purified and re-ligated. Sequencing of 10 clones in each case confirmed, that sequence of cleaved and re-ligated plasmid was identical to the sequence of the non-treated plasmid (part (C) of FIG. 21). This experiment suggests that additional mutations are not introduced after cleavage by Cas9-crRNA complex and ligation, and the Cas9-crRNA complex can be used for cloning experiments. When both complexes were incubated with the pUC18 plasmid, two DNA fragments (2074 and 612 bp) were obtained (part (B) of FIG. 21), indicating that plasmid cleavage occurred at sites targeted by the crRNA molecules present in the complexes. To demonstrate that the pUC18 plasmid cleaved with Cas9-RNA complexes is suitable for a genetic engineering we cloned PCR fragment containing a promoter and a tetracycline resistance gene from the pACYC184 plasmid to the pUC18 vector pre-cleaved with the Cas9 complex mix containing both crRNA1 or crRNA2. The clones were selected on the media enriched by tetracycline and ampicillin. Sequencing of 4 selected clones confirmed that the intact PCR fragment was inserted into a desired position (part (C) of FIG. 21).

More specifically, the 2 µg pUC18 was incubated with the mix of separately assembled Cas9-RNA complexes (250 nM each) containing different crRNAs for 1 hour at 37° C. in 100 µl reaction volume (10 mM Tris-HCl (pH 7.5 at 37° C.), 100 mM NaCl, 1 mM DTT and 10 mM MgCl₂). Obtained vector fragment was purified from agarose gel using Gene-JET gel extraction Kit (Thermo Fisher scientific) and divided in to two equal parts. One part of pre-cleaved vector was dephosphorylated with the FastAP alkaline phosphatase while another part was untreated. 1282 bp insert containing a promoter and a tetracycline resistance gene was obtained from the pACYC184 plasmid by PCR. After purification using the GeneJET PCR Purification Kit (Thermo Fisher scientific), a solution containing the PCR fragment was divided in to two parts. One part was phosphorylated with T4 polynucleotide kinase (Thermo Fisher scientific) while another part remained untreated. Untreated vector was ligated with the untreated PCR fragment, while a dephosphorylated vector was ligated with a phosphorylated fragment using the T4 DNA ligase (Thermo Fisher scientific).

Clones were selected on a media supplemented with 100 μg/ml of Ap and 25 μg/ml Tc.

Example 6

Cleavage of Long DNA Substrates by Cas9 crRNA Complex.

In this example we demonstrate that Cas9-crRNA may be addressed to cleave targets in long DNA molecules, including phage A, *E. coli* and human genomic DNAs.

More specifically, we addressed Cas9-RNA complex to cleave specific sites in A bacteriophage (48 kb), *E. coli* BL-21 strain (4.6 Mb) and human (3.2 Gb) genomic DNAs. Cas9-crRNA complex was assembled as described in Examples 2 and 3. We used 42 nt long synthetic crRNAs, 150 nt pre-crRNAs and tracrRNAs synthesized using in vitro transcription from templates generated as described in Example 4.

A DNA cleavage reactions were initiated by mixing A DNA (Thermo Fisher Scientific) with assembled Cas9-RNA complex (1:1 v/v ratio) and incubating at 37° C. Final reaction mixture contained 2 μg A DNA, 50 nM Cas9-RNA complex, 10 mM Tris-HCl (pH 7.5 at 37° C.), 100 mM NaCl, 1 mM DTT and 10 mM $MgCl_2$ in 100 μl reaction volume. Aliquots were removed at timed intervals and quenched with phenol/chloroform. The aqueous phase was mixed with 3× loading dye solution (0.01% bromphenol blue and 75 mM EDTA in 50% v/v glycerol) and reaction products analyzed by electrophoresis through agarose gels and ethidium bromide staining. The analysis of linear A phage genomic DNA cleavage products in agarose gel confirmed that −40 bp length DNA is efficiently cleaved at a single site (part (A) of FIG. 22).

DNA from *E. coli* BL21 (DE3) strain was isolated using the Genomic DNA purification kit (Thermo Fisher Scientific). For cleavage assay, *E. coli* genomic DNA was combined with assembled Cas9-RNA complex (1:1 v/v ratio) and incubated for 3 hours at 37° C. Final reaction mixture contained 30 μg genomic DNA, 1 μM Cas9-RNA complex, 10 mM Tris-HCl (pH 7.5 at 37° C.), 100 mM NaCl, 1 mM DTT and 10 mM $MgCl_2$ in 300 μl reaction volume. Following incubation, 30 μl of FastDigest PstI (Thermo Fisher Scientific) was added and the reaction mix was incubated for additional 16 hours at 37° C. The reaction was terminated by heating the reaction mixture for 30 min at 55° C. with Proteinase K (0.5 mg/ml; Thermo Fisher Scientific) and SDS (0.5%, w/v) followed by 30 min incubation at room temperature with RNase A (0.25 mg/ml; Thermo Fisher Scientific). After phenol/chloroform extraction, DNA was precipitated by isopropanol and dissolved in TE buffer (10 mM Tris-HCl, pH 8.0 and 1 mM EDTA). 10 μg of DNA was mixed with 3× loading dye solution (0.01% bromphenol blue and 75 mM EDTA in 50% v/v glycerol) and electrophoresed on 1% agarose gel.

To analyse Cas9-crRNA cleavage products of *E. coli* genomic DNA, we designed a probe against DNA fragment containing a Cas9-RNA complex target (a proto-spacer) (part (B) of FIG. 22) and performed Southern blot analysis. Southern blot analysis was performed as described in (Sambrook et al, 1989. Molecular Cloning: A Laboratory Manual) with the following modifications. Fractionated DNA was transferred from agarose gel onto SensiBlot Plus Nylon membrane (Thermo Fisher Scientific) via semi-dry transfer. DNA was denatured and fixed on the membrane by placing it on paper towel saturated with 0.4 M NaOH for 10 min, rinsed with 2×SSC and air dried. The membrane was pre-hybridized with 6×SSC buffer containing 0.5% SDS and 100 μg/ml denatured salmon sperm DNA (Amresco) for 1 h at 65° C. The hybridization probe was generated by PCR using the genomic *E. coli* BL21(DE3) DNA as a template yielding 397 bp product. 5'-ends were dephosphorylated with FastAP phosphatase (Thermo Fisher Scientific) and radiolabelled by incubating with [γ-$^{32}$P]ATP (Hartmann Analytic) and T4 PNK (Thermo Fisher Scientific). The labeled probe was purified using GeneJET PCR Purification Kit (Thermo Fisher Scientific), denatured by heating to 95° C. for 5 min, rapidly cooled on ice and added directly to the prehybridization solution. The membrane was probed for 16 hours at 65° C. and washed twice with 2×SSC, 0.5% SDS and twice with 2×SSC, 0.1% SDS at room temperature, air dried and visualized by phosphorimaging (FLA-5100; Fujifilm).

The probe was designed to target DNA fragment containing a target (a proto-spacer) for the Cas9-RNA complex (part (B) of FIG. 22). The distance between two PstI targets is ~1500 bp, while the distance between proto-spacer and left PstI target is 466 bp. After cleavage with Cas9 complex we detected only 466 bp DNA fragment (part (C) of FIG. 22), which means that all DNA targets were cleaved by Cas9 protein in the desired position. These data clearly demonstrates that Cas9 protein effectively finds targets in very long and complex molecules such as viral and bacterial DNA.

To analyze Cas9-crRNA cleavage products of human genomic DNA we used DNA extracted from human brain. Human genomic DNA was combined with assembled Cas9-crRNA complex (1:1 v/v ratio) and incubated for 30 min at 37° C. Final reaction mixture contained 1 μg genomic DNA, 100 nM Cas9, 10 mM Tris-HCl (pH 7.5 at 37° C.), 100 mM NaCl, 1 mM DTT and 10 mM $MgCl_2$ in 100 μl reaction volume. Cas9-crRNA-HS1 (SEQ ID NO: 13) and Cas9-crRNA-HS2 (SEQ ID NO: 14) complexes were assembled to target RASGEF1C or ARL15 loci, respectively. Cleavage products were analyzed using qPCR (part (D) of FIG. 22). After treatment with Cas9-crRNA complex, the amount of intact DNA targets decreased more than 25 times. The analysis of the results obtained from qPCR data revealed that Cas9-RNA complexes cleave human genomic DNA efficiently in the desired loci. These data clearly demonstrates that Cas9 protein effectively finds targets in very long and complex molecules such as viral, bacterial and mammal DNA.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

The invention claimed is:

1. A composition comprising:
at least one plasmid for preparing a recombinant Cas9-crRNA complex, the at least one plasmid comprising:
a polynucleotide sequence encoding a Cas9 protein containing a mutation in a RuvC nuclease domain or an HNH nuclease domain of the Cas9 protein, wherein the Cas9 protein comprises a fusion polypeptide comprising at least one additional amino acid sequence;
a polynucleotide sequence encoding a tracrRNA; and
a polynucleotide sequence encoding an engineered crRNA, wherein the sequence of the engineered crRNA is heterologous to the sequence of the Cas9 protein and reprogrammed to guide the recombinant Cas9-crRNA complex to a region comprising a site in a target DNA molecule; and
the target DNA molecule, wherein the region of the target DNA molecule comprises at least 20 nucleotides complementary to the engineered crRNA;
wherein the recombinant Cas9-crRNA complex is assembled in vitro; and
wherein the recombinant Cas9-crRNA complex is capable of cleaving the site of the target DNA molecule.

2. The composition of claim 1, wherein the target DNA molecule is a double-stranded DNA molecule.

3. The composition of claim 1, wherein the target DNA molecule is a plasmid DNA.

4. The composition of claim 1, wherein the mutation of the Cas9 protein is a point mutation in the RuvC nuclease domain corresponding to D31A of SEQ ID NO: 1.

5. The composition of claim 1, wherein the Cas9 protein contains a point mutation in the HNH nuclease domain of the Cas9 protein.

6. The composition of claim 1, wherein the mutation of the Cas9 protein is a point mutation in the HNH nuclease domain corresponding to N891A of SEQ ID NO: 1.

7. The composition of claim 1, wherein the sequence encoding the engineered crRNA and the sequence encoding the tracrRNA are produced by in vitro transcription or chemical synthesis, and the sequence encoding the Cas9 protein is produced by recombinant DNA technology or chemical synthesis.

8. The composition of claim 1, wherein the at least one plasmid is isolated from a genetically modified microorganism.

9. The composition of claim 1, wherein the recombinant Cas9-crRNA complex consists essentially of the Cas9 protein, the tracrRNA, and the engineered crRNA.

10. The composition of claim 1, wherein the composition does not comprise RNaseIII.

11. A composition comprising:
a first plasmid for preparing a recombinant Cas9-crRNA complex, the first plasmid comprising:
a polynucleotide sequence encoding a tracrRNA; and
a polynucleotide sequence consisting essentially of one spacer flanked on either side by a repeat, wherein the sequence encodes an engineered crRNA reprogrammed to guide the recombinant Cas9-crRNA complex to a region comprising a site in a target DNA molecule;
a second plasmid comprising a polynucleotide sequence encoding a Cas9 protein, wherein the Cas9 protein comprises a fusion polypeptide comprising at least one additional amino acid sequence; and
the target DNA molecule, wherein the region of the target DNA molecule comprises at least 20 nucleotides complementary to the engineered crRNA;
wherein the first plasmid does not encode a Cas9 protein wherein the recombinant Cas9-crRNA complex is assembled in vitro.

12. The composition of claim 11, wherein the first plasmid consists essentially of the sequence encoding the tracrRNA and the sequence encoding the engineered crRNA.

13. The composition of claim 11, wherein the target DNA molecule is a double-stranded DNA molecule.

14. The composition of claim 11, wherein the composition does not comprise RNaseIII.

15. A composition comprising:

a first plasmid for preparing a recombinant Cas9-crRNA complex, the first plasmid comprising:

a polynucleotide sequence encoding a tracrRNA; and a polynucleotide sequence consisting essentially of one spacer flanked on either side by a repeat, wherein the sequence encodes an engineered crRNA reprogrammed to guide the recombinant Cas9-crRNA complex to a region comprising a site in a target DNA molecule;

wherein the first plasmid does not encode a Cas9 protein;

a second plasmid for preparing the recombinant Cas9-crRNA complex, the second plasmid comprising a polynucleotide sequence encoding a Cas9 protein, wherein the Cas9 protein comprises a fusion polypeptide comprising at least one additional amino acid sequence; and the target DNA molecule, wherein the region of the target DNA molecule comprises at least 20 nucleotides complementary to the engineered crRNA;

wherein the recombinant Cas9-crRNA complex is assembled in vitro; and wherein the recombinant Cas9-crRNA complex is capable of cleaving the site of the target DNA molecule.

16. The composition of claim 15, wherein the target DNA molecule is a double-stranded DNA molecule.

17. The composition of claim 15, wherein the composition does not comprise RNaseIII.

\* \* \* \* \*